(12) United States Patent
Korlach et al.

(10) Patent No.: US 10,590,484 B2
(45) Date of Patent: Mar. 17, 2020

(54) METHODS AND COMPOSITIONS FOR SEQUENCING MODIFIED NUCLEIC ACIDS

(71) Applicant: Pacific Biosciences of California, Inc., Menlo Park, CA (US)

(72) Inventors: Jonas Korlach, Camas, WA (US); Stephen Turner, Eugene, OR (US); Tyson A. Clark, Menlo Park, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 226 days.

(21) Appl. No.: 15/875,652

(22) Filed: Jan. 19, 2018

(65) Prior Publication Data

US 2019/0024162 A1 Jan. 24, 2019

Related U.S. Application Data

(63) Continuation of application No. 14/873,580, filed on Oct. 2, 2015, now abandoned, which is a continuation of application No. 13/836,806, filed on Mar. 15, 2013, now Pat. No. 9,238,836.

(60) Provisional application No. 61/617,999, filed on Mar. 30, 2012.

(51) Int. Cl.
*C12Q 1/6874* (2018.01)
*C12Q 1/6827* (2018.01)

(52) U.S. Cl.
CPC ......... *C12Q 1/6874* (2013.01); *C12Q 1/6827* (2013.01)

(58) Field of Classification Search
None
See application file for complete search history.

(56) References Cited

U.S. PATENT DOCUMENTS

| 5,547,839 | A  | 8/1996 | Dower et al. |
| 6,210,896 | B1 | 4/2001 | Chan |
| 6,255,083 | B1 | 7/2001 | Williams |
| 6,258,540 | B1 | 7/2001 | Lo et al. |
| 6,555,311 | B1 | 4/2003 | Locarnini et al. |
| 6,787,308 | B2 | 9/2004 | Balasubramanian et al. |
| 6,917,726 | B2 | 7/2005 | Levene et al. |
| 7,013,054 | B2 | 3/2006 | Levene et al. |

(Continued)

FOREIGN PATENT DOCUMENTS

| WO | 9106678 A1 | 5/1991 |
| WO | 9627025 A1 | 9/1996 |

(Continued)

OTHER PUBLICATIONS

Vilkaitis et al. Processive Methylation of Hemimethylated CpG Sites by Mouse Dnmt1 DNA Methyltransferase. The Journal of Biological Chemistry 280(1):64-72. (Year: 2005).*

(Continued)

*Primary Examiner* — Samuel C Woolwine
(74) *Attorney, Agent, or Firm* — David C. Scherer

(57) ABSTRACT

Methods, compositions, and systems are provided for characterization of modified nucleic acids. In certain preferred embodiments, single molecule sequencing methods are provided for identification of modified nucleotides within nucleic acid sequences. Modifications detectable by the methods provided herein include chemically modified bases, enzymatically modified bases, abasic sites, non-natural bases, secondary structures, and agents bound to a template nucleic acid.

13 Claims, 3 Drawing Sheets

A.

B.

(56) References Cited

U.S. PATENT DOCUMENTS

| | | |
|---|---|---|
| 7,056,661 B2 | 6/2006 | Korlach et al. |
| 7,170,050 B2 | 1/2007 | Turner et al. |
| 7,315,019 B2 | 1/2008 | Turner et al. |
| 7,399,614 B2 | 7/2008 | Zon |
| 7,459,274 B2 | 12/2008 | Lakey et al. |
| 7,476,503 B2 | 1/2009 | Turner et al. |
| 7,486,865 B2 | 2/2009 | Foquet et al. |
| 7,611,869 B2 | 11/2009 | Fan |
| 7,901,889 B2 | 3/2011 | Christians et al. |
| 7,906,284 B2 | 3/2011 | Turner et al. |
| 7,907,800 B2 | 3/2011 | Foquet et al. |
| 8,003,330 B2 | 8/2011 | Heiner et al. |
| 8,153,375 B2 | 4/2012 | Travers et al. |
| 8,394,584 B2 * | 3/2013 | Timp .......... C12Q 1/6827 435/287.2 |
| 2001/0051341 A1 | 12/2001 | Lo et al. |
| 2002/0025530 A1 | 2/2002 | Affourtit et al. |
| 2002/0102577 A1 | 8/2002 | Raillard et al. |
| 2003/0077633 A1 | 4/2003 | Cox et al. |
| 2003/0096253 A1 | 5/2003 | Nelson et al. |
| 2003/0148273 A1 | 8/2003 | Dong et al. |
| 2003/0190647 A1 | 10/2003 | Odera |
| 2003/0215862 A1 | 11/2003 | Parce et al. |
| 2004/0048300 A1 | 3/2004 | Sood et al. |
| 2004/0152119 A1 | 8/2004 | Sood et al. |
| 2004/0224319 A1 | 11/2004 | Sood et al. |
| 2005/0053937 A1 | 3/2005 | Berlin |
| 2005/0196792 A1 | 9/2005 | Fodor et al. |
| 2005/0208538 A1 | 9/2005 | Kurn et al. |
| 2005/0214812 A1 | 9/2005 | Li et al. |
| 2006/0024676 A1 | 2/2006 | Uhlmann et al. |
| 2006/0063264 A1 | 3/2006 | Turner et al. |
| 2008/0207460 A1 | 8/2008 | Gormley |
| 2009/0012282 A1 | 1/2009 | Zon |
| 2009/0024331 A1 | 1/2009 | Tomaney et al. |
| 2009/0054919 A2 | 2/2009 | Winter-Hilt et al. |
| 2009/0118129 A1 | 5/2009 | Turner |
| 2009/0269771 A1 | 10/2009 | Schroeder |
| 2010/0041057 A1 | 2/2010 | Dong et al. |
| 2010/0121582 A1 | 5/2010 | Pan et al. |
| 2010/0190175 A1 | 7/2010 | Gerard et al. |
| 2010/0221716 A1 | 9/2010 | Flusberg et al. |
| 2010/0311061 A1 | 12/2010 | Korlach et al. |
| 2011/0033854 A1 | 2/2011 | Drmanac et al. |
| 2011/0104787 A1 | 5/2011 | Church et al. |
| 2011/0171634 A1 | 7/2011 | Xiao et al. |
| 2011/0183320 A1 | 7/2011 | Flusberg et al. |
| 2011/0201524 A1 | 8/2011 | Kester |
| 2011/0236894 A1 | 9/2011 | Rao et al. |
| 2011/0237444 A1 | 9/2011 | Clancy et al. |
| 2011/0244447 A1 | 10/2011 | Korlach |
| 2011/0256618 A1 | 10/2011 | Eid et al. |
| 2012/0196279 A1 | 8/2012 | Underwood et al. |
| 2012/0322666 A1 | 12/2012 | Pham et al. |
| 2012/0322692 A1 | 12/2012 | Pham et al. |
| 2013/0157870 A1 | 6/2013 | Pushkarev |
| 2013/0165328 A1 | 6/2013 | Previte et al. |
| 2013/0240359 A1 | 9/2013 | Turner et al. |
| 2014/0024537 A1 | 1/2014 | Rigatti et al. |
| 2014/0134610 A1 | 5/2014 | Pham et al. |
| 2014/0179564 A1 | 6/2014 | Korlach et al. |
| 2016/0168633 A1 | 6/2016 | Previte et al. |
| 2016/0281159 A1 | 9/2016 | Brown et al. |

FOREIGN PATENT DOCUMENTS

| | | |
|---|---|---|
| WO | 9905315 A2 | 2/1999 |
| WO | 2006005064 A2 | 1/2006 |
| WO | 2010068289 A2 | 6/2010 |
| WO | 2010003153 A2 | 7/2010 |
| WO | 2010083046 A2 | 7/2010 |
| WO | 2011057094 A1 | 5/2011 |
| WO | 2012019235 A1 | 2/2012 |

OTHER PUBLICATIONS

Reexamination Report dated Jun. 14, 2018 for related CN 201380028662.3.

Abbotts, J. et al. "Studies on the Mechanism of *Escherichia coli*DNA Polymerase I Large Fragment," Journal of Biological Chemistry (1988) 263:15094-15103.

Ahle, J.D. et al. "Sequence determination of nucleic acids containing 5-methylisocytosine and isoguanine: identification and insight into polymerase replication of the non-natural nucleobases" Nucl Acids Res (2005) 33(10):3176-3184.

Ananiev, G.E. et al. "Optical mapping discerns genome wide DNA methylation profiles" BMC Mol Biol (2008) 9:68.

Avvakumov, G.V. et al. "Structural bases for recognition of hemi-methylated DNA by the SRA domain of human UHRF1" Nature (2008) 455(7214):822-825.

Banerjee, A. et al. "Structure of a repair enzye interrogating undamaged DNA elucidates recognition of damaged DNA" Nature (2005) 434(7033:612-618.

Bareyt, S. et al. "Selective Detection of 5-Methylcytosine Sites in DNA" Angew Chem Int Ed Engl (2008) 47(1):181-184.

Bell, C.G et al. "Integrated Genetic and Epigenetic Analysis Identifies Haplotype-Specific Methylation in the FTO Type 2 Diabetes and Obesity Susceptibility Locus," PLoS One (2010) 5(11):e14040.

Berman, A.J. et al. "Structures of phi29 DNA polymerase complexed with substrate: the mechanism of translocation in B-family polymerases" EMBO J (2007) 26:3494-3505.

Blainey, P.C. et al. "A base-excision DNA-repair protein finds intrahelical leesion bases by fast sliding in contact with DNA" PNAS (2006) 103(15):5752-5757.

Braun, J.V. et al. "Statistical Methods for DNA Sequence Segmentation" Statist Sci (1998) 13(2):142-162.

Brewer, A.C. et al. "A simplified method for in vivo footprinting using DMS" Nucl Acids Res (1990) 18:5574.

Browning, S.R. et al. "Haplotype Phasing: Existing Methods and New Developments," Nat Rev Genet. (2011) 12 (10):703-14.

Brunner, A.L. et al. "Distinct DNA methylation patterns characterize differentiated human embryonic stem cells and developing human fetal liver" Genome Res (2009) 19:1044-1056.

Carrel, L. et al. "X-Inactivation Profile Reveals Extensive Variability in X-Linked Gene Expression in Females," Nature (2005) 434:400-404.

Cipriany, B.R. et al. "Real-Time Analysis and Selection of Methylated DNA by Fluorescence-Activated Single Molecule Sorting in a Nanofluidic Channel," Proc. Natl. Acad. Sci. USA (2012) doi/10.1073/pnas.1117549109.

Clarke, J. et al. "Continuous Base Identification for Single-Molecule Nanopore DNA Sequencing," Nature Nanotechnology (2009) 4:265-70. Published online Feb. 22, 2009.

Colasanti, et al., "Cytosine Methylated DNA Synthesized by Taq Polymerase Used to Assay Methylation Sensitivity of Restriction Endonuclease Hinfl," Nucleic Acids Research (1991) 19(2):391-394.

Cordonnier, A.M. et al. "Impaired translesion synthesis in Xeroderma Pigmentosum variant extracts" Mol Cell Biol (1999) 19(3):2206-2211.

Crews, D. et al., "Epigenetic Transgenerational Inheritance of Altered Stress Responses," Proc. Natl. Acad. Sci. USA (2012) doi/10.1073/pnas.1118514109.

Delanaeu, O. et al. "Haplotype Estimation Using Sequencing Reads," Am J Hum Genet. (2013) 93(4):687-96.

Drozdz, M. et al. "Novel Non-Specific DNA Adenine Methyltransferases," Nucleic Acids Research (2011) doi:10.1093/nar/gkr 1039.

Duncavage, E.J. et al. "Hybrid Capture and Next-Generation Sequencing Identify Viral Integration Sites form Formalin-Fixed, Paraffin-Embedded Tissue," J. Mol Diagn (2011) 13(3):325-33.

Easwaran, H. et al. "A DNA Hypermethylation Module for the Stem/Progenitor Cell Signature of Cancer," Genome Research (2012) 22:837-849.

Eid, J. et al. "Real-time DNA Sequencing from Single Polymerase Molecules" Science (2009) 323:133-138.

(56) References Cited

OTHER PUBLICATIONS

Erlich, Y. "Blood Ties: Chimerism Can Mask Twin Discordance in High Throughput Sequencing," Twin Research and Human Genetics (2011) 14(2):137-143.
Everts "RNA's Outfits" The nucleic acid has dozens of chemical costumes C&EN (2009) 87:36:65-68.
Fang, G. et al. "Genome-Wide Mapping of Methylated Adenine Residues in Pathogenic *Escherichia coli* Using Single-Molecule Real-Time Sequencing," Nature Biotechnology (2012) 30(12):1232-1238.
Fellers, J.P. "Genome Filtering Using Methylation-Sensitive Restriction Enzymes with Six Base Pair Recognition Sites" Plant Genome (2008) 1(2):146-152.
Finkel, T. et al. "Oxidants, oxidative stress and the biology of ageing" Nature (2000) 408(6809:239-247.
Flusberg, B.A. et al. "Direct detection of DNA Methylation and Mutagenic Damage Through Single-Molecule, Real-Time (SMRT) DNA Sequencing", 101st Annual Meeting of American Association for Cancer Research; Washington, D.C. USA; Apr. 17-21, 2010.
Flusberg, B.A. et al. "Direct detection of DNA methylation during single-molecule, real-time sequencing" Nat Meth (2010) 7(6):461-467.
Forsberg, L.A. et al. "Age-Related Somatic Structural Changes in the Nuclear Genome of Human Blood Cells," Am. J. Hum. Genet. (2012) 90:217-228.
Friedberg, E.C. "Suffering in Silence: The Tolerance of DNA Damage" Nat Rev Mol Cell Biol (2005) 6(12):943-953.
Fromme, J.C. et al. "Base Excision Repair" Adv Protein Chem (2004) 69:1-41.
Fuks, F. et al. "DNA Methylation and Histone Modifications: Teaming up to Silence Genes," Curr. Op. Genetics & Development (2005) 15:1-6.
Galas, D.J. et al. "DNAase Footprinting: A Simple Method for the Detection of Protein-DNA Binding Specificity," Nucleic Acids Research (1978) 5(9):3157-3170.
Gervin, K. et al. "DNA Methylation and Gene Expression Changes in Monozygotic Twins Discordant for Psoriasis: Identification of Epigenetically Dysregulated Genes," PLoS One (2012) 8(1):e1002454.
Gussin, H.A.E. et al. "Culture of Fetal Cells from Maternal Blood for Prenatal Diagnosis," Human Reproduction Update (2002) 8(6):523-527.
Hafner, M. et al. "Transcriptome-wide identification of RNA-binding protein and microRNA target sites by PAR-CLIP" Cell (2010) 141(1):129-141.
Hamm, M.L. et al. "Substrate Specificity of Fpg (MutM) and hOGG1, Two Repair Glycosylases" J Am Chem Soc. (2007) 129(25):7724-7725.
Hanes, J.W. et al. "Incorporation and replication of 8-oxo-deoxyguanosine by the human mitochrondrial DNA polymerase" J Biol Chem (2006) 281(47):36241-36248.
Hashimoto, H. et al. "The SRA domain of UHRF1 flips 5-methylcytosine out of the DNA helix" Nature (2008) 455 (7214):826-829.
Hayatsu, H. "The bisulfite genomic sequencing used in the analysis of epigenetic states, a technique in the emerging environmental genotoxicology research" Mutation Res (2008) 659(1-2):77-82.
Hendrich, B. et al. "Identification and Characterization of a Family of Mammalian Methyl-CpG Binding Proteins" Mol Cell Biol (1998) 18(11):6538-6547.
Herbert, K.M. et al. "Single-Molecule Studies of RNA Polymerase: Motoring Along" Ann Rev Biochem (2008) 77:149-176.
Herzenberg, L.A. et al. "Fetal Cells in the Blood of Pregnant Women: Detection and Enrichment by Fluorescence-Activated Cell Sorting,"Proc. Natl. Acad. Sci. USA (1979) 76(3):1453-1455.
Holmquist et al. "The bypass of DNA lesions by DNA and RNA polymerases" Mutat Res (2002) 510(1-2):1-7.
Horowitz, S. et al. "Mapping of N6-methyladenosine residues in bovine prolactin mRNA" PNAS (1984) 81(18):5667-5671.
Hsu, G.W. et al. "Error-prone replicatin of oxidatively damaged DNA by a high-fidelity DNA polymerase" Nature (2004) 431(7005:217-221.

Huang, T. H-M et al. "Identification of DNA Methylation Markers for Human Breast Carcinomas Using the Methylation-sensitive Restriction Fingerprinting Technique" Cancer Res (1997) 57:1030-1034.
Vidal, A.E. et al. "Mechanism of stimulation of the DNA glycosylase activity of hOGG1 by the major human AP endonuclease: bypass of the AP lyase activity step" Nucl Acids Res (2001) 29(6):1285-1292.
Viguera, E. et al. "Replication slippage involves DNA polymerase pausing and dissociation" EMBO J (2001) 20(10):2587-2595.
Vlassov, V.V. et al. "Extracellular Nucleic Acids" Bioessays (2207) 29(7):654-667.
Weber, J. et al. "Chromosome-wide and promoter-specific analyses identify sites of differential DNA methylation in normal and transformed human cells" Nat Genet (2005) 37:853-862.
Xiao, M. et al. "Determination of Haplotypes from Single DNA Molecules: A Method for Single-Molecule Barcoding," Human Mutation (2007) 28(9):913-921.
Yebra, M.J. et al. "A Cytosine Methyltransferase Converts 5-Methylcytosine in DNA to Thymine" Biochemistry (1995) 34(45):14752-14757.
Zhang, Y. et al. "Transcription Regulation by Histone Methylation: Interplay Between Different Covalent Modifications of the Core Histone Tails," Genes & Development (2001) 15:2343-2360.
Zheng, K-W. et al. "Molecular crowding creates an essential environment for the formation of stable G-quadruplexes in long double-stranded DNA" Nucl Acids Res (2010) 38(1):327-338.
Ziller, M.J. et al. "Genomic Distribution and Inter-Sample Variation of Non-CpG Methylation Across Human Cell Types," PLoS One (2011) 7(12):e14002389.
International Search Report and Written Opinion dated Jul. 9, 2013 for related PCT/US2013/032816.
International Preliminary Report on Patentability dated Oct. 4, 2014 for related PCT/US2013/032816.
EP Search Report dated Oct. 2, 2015 for related EP 13769322.2.
First Office Action dated Dec. 28, 2015 for related CN 201380028662.3.
Second Office Action dated Sep. 13, 2016 for related CN 201380028662.3.
First Exam Report dated Dec. 7, 2016 for related EP 13769322.2.
Decision on Rejection dated May 2, 2017 for related CN 201380028662.3.
First Exam Report dated Dec. 8, 2017 for related AU 2013240166.
Second Exam Report dated May 10, 2018 for related AU 2013240166.
Ingolia, N.T. et al. "Genome-Wide Analysis in Vivo of Translation with Nucleotide Resolution Using Ribosome Profiling" Science (2009) 324(5924):218-223.
Jones, P.A. et al. "Cancer epigenetics comes of age" Nat Genet (1999) 21(2):163-167.
Jorgensen, H.F. et al. "Engineering a high-affinity methyl-CpG-binding protein" Nucl Acids Res (2006) 34(13):e96.
Kannouche, P.L. et al. "Interaction of Human DNA Polymerase r with Monoubiquitinated PCNA: A Possible Mechanism for the Polymerase Switch in Response to DNA Damage" Mol Cell (2004) 14(4):491-500.
Kannouche, P.L. et al. Ubiquitination of PCNA and the Polymerase Switch in Human Cells Cell Cycle (2004) 3(8):1011-1013.
Kilgore, J.A. et al. "Single-molecule and population probing of chromatin structure using DNA methyltransferases" Methods (2007) 41:320-332.
Kitzman, J.O. et al. "Hapolotype-Resolved Genome Sequencing of a Gujarati Indian Individual," Nat Biotechnol (2011) 29(1):59-63. Epublished Dec. 19, 2010.
Klungland, A. et al. "Oxidative damage to purines in DNA: Role of Mammalian Ogg1" DNA Repair (AMST) (2007) 6(4):481-488.
Kriaucionis, S. et al. "The Nuclear DNA Base 5-Hydroxymethylcytosine is Present in Purkinje Neurons and the Brian" Science (2009) 324(5929) :929-930.
Krueger, A.T. et al. "Model Systems for Understanding DNA Base Pairing" Chem & Biol (2009) 16(3):242-248.
Krueger, A.T. et al. "Redesigning the Architecture of the Base Pair: Toward Biochemical and Biological Function of New Genetic Sets" Curr Opin Chem Biol (2007) 11(69):588-594.

(56) References Cited

OTHER PUBLICATIONS

Laird, P.W. "The power and the promise of DNA methylation markers" Nat Rev Cancer (2003) 3(4):253-266.
Lehmann, A.R. "Replication of damaged DNA in mammalian cells: new solutions to an old problem" Mutant Res (2002) 509(1-2):23-34.
Lehmann, A.R. "Translesion synthesis in mammalian cells" Exp Cell Res (2006) 312(14):2673-2676.
Lehmann, A.R. et al. "Translesion synthesis: Y-family polymerases and the polymerase switch" DNA Repair (Amst) (2007) 6(7):891-899.
Levene, M.J. et al. "Zero-mode Waveguides for Single-Molecule Analysis at High Concentrations" Science (2003) 299(5607):682-686.
Li, M. et al. "Widespread RNA and DNA Sequence Differences in the Human Transcriptome," Science (2011) 10.1126/science.1207018.
Lindahl, T. "Instability and decay of the primary structures of DNA" Nature (1993) 362(6422):709-715.
Lindsay, S.J. et al. "Shotgun Haplotyping: A Novel Method for Surveying Allelic Sequence Variation," Nucleic Acids Research (2005) 33(18):e152.
Lister, R. et al. "Finding the fifth base: Genome-wide sequencing of cytosine methylation" Genome Res (2009) 19:959-966.
Loakes, D. et al. "Polymerase engineering: towards the encoded synthesis of unnatural biopolymers" Chem Commun (2009) 31:4619-4631.
Ludlum, et al., "Ribonucleic Acid Polymerase Reactions with Methylated Polycytidylic Acid Templates," Journal of Biological Chemistry (1968) 243(10):2750-2753.
Masutani, C. et al. "The XPV (xeroderma pigmentosum variant" gene encodes human DNA polymease Nature (1999) 399(6737):700-704.
Matray, T.J. et al. "A specific partner for abasic damage in DNA" Nature (1999) 399:704-708.
McCullough, A.K et al. "Initiation of Base excision repair: glycosylase mechanisms and structures" Ann Rev Biochem (1999) 68-255-285.
Meissner, A. et al. "Genome-scale DNA methylation maps of pluripotents and differentiated cells" Nature (2008) 454:766-770 (+ supplementary information ).
Merino, E.J. et al. "RNA Structure Analysis at Single Nucleotide Resolution by Selective 2'-Hydroxyl Acylation and Extension (SHAPE)" J Am Chem Soc (2005) 127:4223-4231.
Morgan, H.D. et al. "Activation-induced cytidine deaminase deaminates 5-methylcytosine in DNA and is expressed in pluripotent tissues" J Biol Chem (2004) 279:52353-52360.
Morozova, O. et al. "Applications of next generation sequencing technologies in functional genomics" Genomics (2008) 92:255-264.
Narayan, P. et al. "Unequal Distribution of N6-Methyladenosine in Influenza Virus mRNAs" Mol Cell Biol (1987) 7(4):1572-1575.
Ohki, I et al. "Solution structures of the methyl-CpG-binding domain of the methylation-dependent transcriptional repressor MBD1" EMBO J (2000) 18(23):6653-6661.
Ohmori, "The Y-Family of DNA Polymerases" et al. Mol Cell (2001) 8(1):7-8.
Okamoto, A. "5-Methylcytosine-Selective Osmium Oxidation" Nucleosides, Nucleotides, Nucleic Acids (2007) 26(10-12):1601-1604.
Petrov, A.I. et al. "Spin-labeled polyribonucleotids" Nucl Acids Res (1980) 8(18):4221-4234.
Radicella, J.P. et al. "Cloning and characterization of hOGG1, a human homolog of the OGG1 gene of *Saccharomyces cerevisiae*" PNAS (1997) 94:8010-8015.
Rollins, R.A. et al. "Large-scale structure of genomic methylation patterns" Genome Res (2006) 16-157-163.
Sadri, R. et al. "Rapid analysis of DNA methylation using new restriction enzyme sites created by bisulfite modification" Nucl Acids Res (1996) 24(24):5058-5059.
Schadt, E. et al. "A Window Into Third-Generation Sequencing," Hum Mol Genet. (2010) 19(R2):R222-40. Epub Sep. 21, 2010.
Seo, Y.J. et al. "Optimization of an Unnatural Base Pair toward Natural-Like Replication" J Am Chem Soc (2009) 131-3246-3252.
Shoemaker, R. et al. "Allele-Specific Methylation is Prevalent and is Contributed by CpG-SNPs in the Human Genome," Genome Research (2010) 20:883-889.
Smith, S.S. et al. "Mechanism of human methyl-directed DNA methyltransferase and the fidelity of cytosine methylation" PNAS (1992) 89:4744-4748.
Smolina, I.V. et al. "Pausing of DNA Polymerases on Duplex DNA Templates due to Ligand Binding in Vitro" J Mol Biol (2003) 326:1113-1125.
Song, C. et al. "Sensitive and Specific Single-Moledule Sequencing of 5-Hydroxymethylcytosine," Nat Methods (2011) 9(1):75-7.
Tahiliani, M. et al. "Conversion of 5-Methylcytosine to 5-Hydroxymethylcytosine in Mammalian DNA by MLL Partner TET1" Science (2009) 324(5929):930-935.
Tahiliani, M. et al. "Supporting Online Material for Conversion of 5-Methylcytosine to 5-Hydroxymethylcytosine in Mammalian DNA by MLL Partner TET1" Science (2009) 324(5929):930-935.
Takasugi, M. et al. "DNA Methylation Status of Nuclear-Encoded Mitochondrial Genes Underlies the Tissue-Dependent Mitochondrial Functions," BMC Genomics (2010) 11:481.
Tanaka, K. et al. "Direct Labeling of 5-Methylcytosine and its Applications" J Am Chem Soc (2007) 129(17):5612-5620.
Thompson, J. et al. "The Properties and Applications of Single-Molecule DNA Sequencing," Genome Biology (2011) 12:217.
Tijerina, P. et al. "DMS Footprinting of Structured RNAs and RNA-Protein Complexes" Nature Protocols (2007) 2:2608-2623.
Tost, et al., "DNA Methylation Analysis by Pyrosequencing," Nature Protocols (2007) 2(9):2265-2275.

\* cited by examiner

METHODS AND COMPOSITIONS FOR SEQUENCING MODIFIED NUCLEIC ACIDS

CROSS-REFERENCE TO RELATED APPLICATIONS

This application is a continuation of U.S. patent application Ser. No. 14/873,580 filed Oct. 2, 2015, which is a continuation of U.S. patent application Ser. No. 13/836,806 filed Mar. 15, 2013, now U.S. Pat. No. 9,238,836, which claims the benefit of U.S. Provisional Application No. 61/617,999, filed Mar. 30, 2012, which is incorporated herein by reference. This application is further related to U.S. Provisional Application Nos. 61/721,206 and 61/721,339, both filed Nov. 1, 2012, U.S. Provisional Application No. 61/789,354 filed Mar. 15, 2013 and U.S. Provisional Application No. 61/799,237 filed Mar. 15, 2013, all of which are incorporated herein by reference in their entireties for all purposes.

STATEMENT REGARDING FEDERALLY SPONSORED RESEARCH

Not Applicable.

BACKGROUND OF THE INVENTION

Assays for analysis of biological processes are exploited for a variety of desired applications. For example, monitoring the activity of key biological pathways can lead to a better understanding of the functioning of those systems as well as those factors that might disrupt the proper functioning of those systems. In fact, various different disease states caused by operation or disruption of specific biological pathways are the focus of much medical research. By understanding these pathways, one can model approaches for affecting them to prevent the onset of the disease or mitigate its effects once manifested.

A stereotypical example of the exploitation of biological process monitoring is in the area of pharmaceutical research and development. In particular, therapeutically relevant biological pathways, or individual steps or subsets of individual steps in those pathways, are often reproduced or modeled in in vitro systems to facilitate analysis. By observing the progress of these steps or whole pathways in the presence and absence of potential therapeutic compositions, e.g., pharmaceutical compounds or other materials, one can identify the ability of those compositions to affect the in vitro system, and potentially beneficially affect an organism in which the pathway is functioning in a detrimental way. By way of specific example, reversible methylation of the 5' position of cytosine by methyltransferases is one of the most widely studied epigenetic modifications. In mammals, 5-methylcytosine (5-MeC) frequently occurs at CpG dinucleotides, which often cluster in regions called CpG islands that are at or near transcription start sites. Methylation of cytosine in CpG islands can interfere with transcription factor binding and is associated with transcription repression and gene regulation. In addition, DNA methylation is known to be essential for mammalian development and has been associated with cancer and other disease processes. Epigenetic enhancer patterns have been identified in colon cancer cell lines, and a 5-hydroxymethylcytosine epigenetic marker has been identified in certain cell types in the brain, suggesting that it plays a role in epigenetic control of neuronal function (Akhtar-Zaidi, et al. (2012) *Science* 336(6082):736-739; and S. Kriaucionis, et al., *Science* 2009, 324(5929): 929-30, incorporated herein by reference in their entireties for all purposes). Further information on cytosine methylation and its impact on gene regulation, development, and disease processes is provided in the art, e.g., in A. Bird, *Genes Dev* 2002, 16, 6; M. Gardiner-Garden, et al., *J Mol Biol* 1987, 196, 261; S. Saxonov, et al., *Proc Natl Acad Sci USA* 2006, 103, 1412; R. Jaenisch, et al., *Nat Genet* 2003, 33 Suppl, 245; E. Li, et al., *Cell* 1992, 69, 915; A. Razin, et al., *Hum Mol Genet* 1995, 4 Spec No, 1751; P. A. Jones, et al., *Nat Rev Genet* 2002, 3, 415; P. A. Jones, et al., *Nat Genet* 1999, 21, 163; and K. D. Robertson, *Nat Rev Genet* 2005, 6, 597, all of which are incorporated herein by reference in their entireties for all purposes. Further, a large number of other nucleotide modifications are known in the art that play biological roles in some capacity, and these include, without limitation, $N^6$-methyladenosine, $N^3$-methyladenosine, $N^7$-methylguanosine, pseudouridine, thiouridine, isoguanosine, isocytosine, dihydrouridine, queuosine, wyosine, inosine, triazole, diaminopurine, and 2'-O-methyl derivatives of adenosine, cytidine, guanosine, and uridine.

In contrast to determining a human genome, mapping of the human methylome is a more complex task because the methylation status differs between tissue types, changes with age, and is altered by environmental factors (P. A. Jones, et al., *Cancer Res* 2005, 65, 11241, incorporated herein by reference in its entirety for all purposes). Comprehensive, high-resolution determination of genome-wide methylation patterns from a given sample has been challenging due to the sample preparation demands and short read lengths characteristic of current DNA sequencing technologies (K. R. Pomraning, et al., *Methods* 2009, 47, 142, incorporated herein by reference in its entirety for all purposes).

Bisulfite sequencing is the current method of choice for single-nucleotide resolution methylation profiling (S. Beck, et al., *Trends Genet* 2008, 24, 231; and S. J. Cokus, et al., *Nature* 2008, 452, 215, the disclosures of which are incorporated herein by reference in their entireties for all purposes). Treatment of DNA with bisulfite converts unmethylated cytosine, but not 5-MeC, to uracil (M. Frommer, et al., *Proc Natl Acad Sci USA* 1992, 89, 1827, incorporated herein by reference in its entirety for all purposes). The DNA is then amplified (which converts all uracils into thymines) and subsequently analyzed with various methods, including microarray-based techniques (R. S. Gitan, et al., *Genome Res* 2002, 12, 158, incorporated herein by reference in its entirety for all purposes) or $2^{nd}$-generation sequencing (K. H. Taylor, et al., *Cancer Res* 2007, 67, 8511; and R. Lister, et al., *Cell* 2008, 133, 523, both incorporated herein by reference in their entireties for all purposes). While bisulfite-based techniques have greatly advanced the analysis of methylated DNA, they also have several drawbacks. First, bisulfite sequencing requires a significant amount of sample preparation time (K. R. Pomraning, et al., supra). Second, the harsh reaction conditions necessary for complete conversion of unmethylated cytosine to uracil lead to degradation of DNA (C. Grunau, et al., *Nucleic Acids Res* 2001, 29, E65, incorporated herein by reference in its entirety for all purposes), and thus necessitate large starting amounts of the sample, which can be problematic for some applications.

Furthermore, because bisulfite sequencing relies on either microarray or 2nd-generation DNA sequencing technologies for its readout of methylation status, it also suffers from the same limitations as do these methodologies. For array-based procedures, the reduction in sequence complexity caused by bisulfite conversion makes it difficult to design enough unique probes for genome-wide profiling (S. Beck, et al., supra). Most 2nd-generation DNA sequencing techniques employ short reads and thus have difficulties aligning to highly repetitive genomic regions (K. R. Pomraning, et al., supra). This is especially problematic, since many CpG islands reside in such regions. Given these limitations, bisulfite sequencing is also not well suited for de novo methylation profiling (S. Beck, et al., supra).

In another widely used technique, methylated DNA immunoprecipitation (MeDIP), an antibody against 5-MeC is used to enrich for methylated DNA sequences (M. Weber, et al., Nat Genet 2005, 37, 853, incorporated herein by reference in its entirety for all purposes). MeDIP has many advantageous attributes for genome-wide assessment of methylation status, but it does not offer as high base resolution as bisulfite treatment-based methods. In addition, it is also hampered by the same limitations of current microarray and 2nd-generation sequencing technologies.

Research efforts aimed at increasing our understanding of the human methylome would benefit greatly from the development of a new methylation profiling technology that does not suffer from the limitations described above. Further, additional modifications are known to occur in human genetic material that are not detectable by the methods described above, e.g., hydroxymethylcytosine bases. Accordingly, there exists a need for improved techniques for detection of modifications in nucleic acid sequences, and particularly nucleic acid methylation.

Further, DNA is under constant stress from both endogenous and exogenous sources and is vulnerable to chemical modifications through different types of damage, including oxidation, alkylation, radiation damage, and hydrolysis. DNA base modifications resulting from these types of DNA damage are wide-spread and play important roles in physiological pathways and disease phenotypes (see, e.g., Geacintov, et al. (2010) The Chemical Biology of DNA Damage, Wiley-VCH Verlag GmbH & Co. KGaA; Kelley, M R (2011) DNA Repair in Cancer Therapy: Molecular Targets and Clinical Applications, Elsevier Science; and Preston, et al. (2011) Semin. Cancer Biol. 20:281-293, the disclosures of which are incorporated herein by reference in their entireties for all purposes). Examples include 8-oxoguanine, 8-oxoadenine (oxidative damage; aging, Alzheimer's, Parkinson's), 1-methyladenine, 6-O-methylguanine (alkylation; gliomas and colorectal carcinomas), benzo[a]pyrene diol epoxide (BPDE), pyrimidine dimers (adduct formation; smoking, industrial chemical exposure, UV light exposure; lung and skin cancer), and 5-hydroxycytosine, 5-hydroxyuracil, 5-hydroxymethyluracil, and thymine glycol (ionizing radiation damage; chronic inflammatory diseases, prostate, breast and colorectal cancer). Currently, these and other products of DNA damage are detected using bulk measurements including chromatographic techniques, polymerase chain reaction assays, the Comet assay, mass spectrometry, electrochemistry, radioactive labeling and immunochemical methods (see, e.g., Kumari, et al. (2008) EXCLI J. 7:44-62, incorporated herein by reference in its entirety for all purposes). Sequencing individual DNA molecules would be beneficial for mapping base damage, which can occur at random DNA template positions.

Typically, modeled biological systems rely on bulk reactions that ascertain general trends of biological reactions and provide indications of how such bulk systems react to different effectors. While such systems are useful as models of bulk reactions in vivo, a substantial amount of information is lost in the averaging of these bulk reaction results. In particular, the activity of and effects on individual molecular complexes cannot generally be teased out of such bulk data collection strategies.

Single-molecule real-time analysis of nucleic acid synthesis has been shown to provide powerful advantages over nucleic acid synthesis monitoring that is commonly exploited in sequencing processes. In particular, by concurrently monitoring the synthesis process of nucleic acid polymerases as they work in replicating nucleic acids, one gains advantages of a system that has been perfected over millions of years of evolution. In particular, the natural DNA synthesis processes provide the ability to replicate whole genomes in extremely short periods of time, and do so with an extremely high level of fidelity to the underlying template being replicated.

BRIEF SUMMARY OF THE INVENTION

The present invention is generally directed to the combined analysis of epigenetic modifications and genomic sequences. In preferred embodiments, a single analytical reaction provides both base sequence data and modification data for a single nucleic acid template molecule. For example, a real time single molecule sequencing method can be used to detect modified nucleic acid sequences, e.g., methylated bases, within nucleic acid sequences. The present invention is expected to have a major impact on research aiming to illuminate the role of nucleic acid modifications, e.g., epigenetic modifications, in the study of genetics, genomics, and human health.

Allele calling in DNA sequencing is affected by binomial sampling statistics, which complicates the distinction between errors and heterozygote genotypes at low coverage. This challenge is even greater in polyploidy organisms. Methods herein facilitate identification of a chromosomal source of a sequence read based on characteristic base modifications. In certain aspects, the invention provides methods for identifying a chromosomal source of a sequencing read, and then grouping that data with other sequencing reads from the same source prior to further statistical analysis, e.g., consensus sequence determination. In certain embodiments, differential modification of homologous chromosomes is detected kinetically during a sequencing reaction, and the resulting differential modification data s used to identify the chromosomal source of the sequencing read corresponding to the kinetic data.

In certain aspects of the invention, a method of sequencing homologous chromosomes is provided that comprises: a) providing a pair of homologous chromosomes having a locus of interest, the pair comprising a first homolog and a second homolog, wherein the first homolog comprises a modified base at the locus of interest and the second homolog lacks the modified base at the locus of interest; b) sequencing the first homolog and the second homolog, wherein each nucleotide sequenced is subjected to an interrogation that provides both base composition data and kinetic data, thereby generating sequence reads for the locus of interest from both the first homolog and the second homolog, the sequence reads comprising both said base composition data and said kinetic data; c) analyzing the base composition data and the kinetic data for said locus of interest to identify a first subset of the sequence reads that comprise the modification, and assigning the first subset to the first homolog; and d) analyzing the base composition data and the modification data for said locus of interest to identify a second subset of the sequence reads that lack the modification, and assigning the second subset to the second homolog. In some embodiments, the modified base is a methylated base. In preferred embodiments, the locus of interest from either or both homologs is not bisulfite-converted, amplified, and/or cloned. Single-molecule sequencing is a preferred sequencing technology, e.g., sequencing-by-incorporation, tSMS sequencing, and nanopore sequencing, and both homologs can be sequenced in the same reaction mixture. In some applications of the method, the homologs are X chromosomes from an individual. The locus of interest is optionally within a highly repetitive region or an imprinted region. Alternatively or in addition, the locus of interest is at least one of a drug target, a locus associated with a genetic disorder, or a forensic marker.

In other aspects, the invention provides methods for identifying sequence differences between two nucleic acids from different sources. In some embodiments, such a method comprises: providing a first nucleic acid from a first sample; providing a second nucleic acid from a second sample; treating the first nucleic acid to produce a modified nucleic acid; denaturing the modified nucleic acid and the second nucleic acid; annealing the modified nucleic acid to the second nucleic acid, thereby producing hybrid nucleic acids that comprise a first modified strand from the first sample and a second unmodified strand from the second sample, and further wherein a portion of the hybrid nucleic acids comprise non-complementary regions of one or more base pairs where the first modified strand and the second unmodified strand are non-complementary; binding a non-complementary-region-specific binding agent to the portion of the hybrid nucleic acids, wherein the non-complementary-region-specific binding agent comprises a selectable tag; capturing the portion of the hybrid nucleic acids bound to the non-complementary-region-specific binding agent using the selectable tag; removing nucleic acids not bound to the non-complementary-region-specific binding agent; subjecting the portion of the hybrid nucleic acids to a single type of sequencing reaction in which both the first and second strands of the hybrid nucleic acids are sequenced and both sequence data and modification data are provided in a single sequence read; for each sequence read, analyzing the sequencing data to identify said single-stranded regions where the first modified strand and second unmodified strand are non-complementary; and for each sequence read, analyzing the modification data to determine which portion of said sequence read corresponds to the first modified strand and which portion corresponds to the second unmodified strand, thereby identifying sequence differences between the first nucleic acid from the first sample and the second nucleic acid from the second sample. Optionally, the treating introduces one or more modifications into the first nucleic acid that render it distinguishable from the second nucleic acid. The modifications typically, but not necessarily, comprise methylation, demethylation, hydroxymethylation, or glucosylation. In some preferred embodiments, the first sample is a tumor sample and the second sample is a non-tumor sample, and the sequence differences identified correspond to mutations that occurred during development of a tumor. In certain embodiments, the the non-complementary-region-specific agent is selected from a single-strand-specific binding agent and a mismatch-repair agent. In optional embodiments, subsequent to the annealing and prior to the subjecting the method comprises incorporating the hybrid nucleic acids into template molecules having at least one adapter that links the first modified strand to the second unmodified strand, and such incorporating preferably occurs prior to the capturing.

In yet further aspects, methods for identifying loci where two nucleic acids from two different sources are non-complementary. Such a method comprises, in certain embodiments, providing a first nucleic acid from a first sample; providing a second nucleic acid from a second sample; denaturing the first nucleic acid and the second nucleic acid; annealing the first nucleic acid to the second nucleic acid, thereby producing hybrid nucleic acids that comprise a first strand from the first sample and a second strand from the second sample, and further wherein a portion of the hybrid nucleic acids comprise non-complementary regions of one or more base pairs where the first strand and the second strand are non-complementary; performing mismatch repair on the hybrid nucleic acids using modified nucleotides comprising a selectable tag, thereby generating repaired hybrid nucleic acids; isolating the repaired hybrid nucleic acids using the selectable tag; subjecting the repaired hybrid nucleic acids to a single type of sequencing reaction in which both the first and second strands of the repaired hybrid nucleic acids are sequenced and both sequence data and modification data are provided in a single sequence read; and for each sequence read, analyzing the sequence data and modification data to determine which portion of said sequence read comprises the modified nucleotides, thereby identifying loci at which the first nucleic acid and second nucleic acid were non-complementary. In some embodiments, the modified nucleotides comprise one or more methylated nucleotides, hydroxymethylated nucleotides, or glucosylated nucleotides. In certain embodiments, the first sample is a tumor sample and the second sample is a non-tumor sample, and further wherein the loci at which the first nucleic acid and second nucleic acid were non-complementary correspond to mutations that occurred during development of a tumor. In optional embodiments, subsequent to the annealing and prior to the subjecting the method comprises incorporating the hybrid nucleic acids into template molecules having at least one adapter that links the first strand to the second strand, and such incorporating preferably occurs prior to the capturing.

In other aspects, the invention provides methods of identifying fetal sequence reads that comprise providing a mixture of maternal nucleic acids and fetal nucleic acids; sequencing individual nucleic acids from the mixture, thereby generating a set of sequence reads comprising sequence reads from the maternal nucleic acids and sequence reads from the fetal nucleic acids, wherein each of the sequence reads have both base sequence data and modification data; and analyzing the modification data to identify which of the set of sequence reads are fetal sequence reads.

Similarly, the invention provides methods of identifying tumor-derived sequence reads that comprise providing a mixture of non-tumor-derived nucleic acids and tumor-derived nucleic acids; sequencing individual nucleic acids from the mixture, thereby generating a set of sequence reads comprising sequence reads from the non-tumor-derived nucleic acids and sequence reads from the tumor-derived nucleic acids, wherein the sequence reads have both base sequence data and modification data; and analyzing the modification data to identify which of the set of sequence reads are tumor-derived sequence reads.

The invention also provides, in certain aspects, methods of identifying aberrant cells in a biological sample that comprise providing a biological sample comprising a mixture of cells; isolating nucleic acids from the mixture of cells; individually sequencing said nucleic acids from the mixture, thereby generating a set of sequence reads comprising both base sequence data and modification data; and analyzing the modification data to identify which of the set of sequence reads are native to the biological sample and which of the set of sequence reads are from aberrant cells in the biological sample. Optionally, the biological sample is a blood sample, sputum sample, urine sample, nasopharangeal sample, vaginal sample, biopsy, buccal sample, and colonic sample. In preferred embodiments, the aberrant cells are one or more of tumor cells, stem cells, pluripotent cells, bacterial cells, fungal cells, embryonic cells, or cells from a parasitic organism.

In certain aspects, methods are provided for identifying a pluripotent cell line that include providing a differentiated cell line, contacting the differentiated cell line with at least one reprogramming agent that contributes to reprogramming of said cell to a pluripotent state; maintaining said cell line under conditions appropriate for proliferation of said cell line and for activity of said at least one reprogramming agent for a period of time sufficient to begin reprogramming of said cell line; and periodically sequencing nucleic acids isolated from said cell line to provide both base sequence data and modification data in single sequence reads, wherein the prevalence of non-CpG methylation in the cell line is indicative that the differentiated cell line has been reprogrammed into a pluripotent cell line.

In other aspects, methods are provided for identifying pseudogene sequence reads that include providing a mixture of nucleic acids from a genome comprising both genes and pseudogenes; sequencing individual nucleic acids from the mixture, thereby generating a set of sequence reads comprising sequence reads from the genes and sequence reads from the pseudogenes, wherein each of the sequence reads have both base sequence data and methylation data; and analyzing the methylation data to identify which of the set of sequence reads are pseudogene sequence reads by virtue of the different methylation patterns in genes and pseudogenes.

In yet further aspects, methods are provided for diagnosing an environmental exposure that involve performing single-molecule sequencing on nucleic acids isolated from an individual, where the sequencing provides both genetic data and epigenetic data; and based on the genetic data and epigenetic data, diagnosing whether the individual experienced the environmental exposure. In some embodiments, the epigenetic data is indicative of (1) activation or inactivation of a gene known to be impacted by the environmental exposure, or (2) activation of a metabolic pathway specific for response to the environmental exposure. Optionally, the environmental exposure is one or more of radiation exposure, toxin exposure, pathogen exposure, and malnutrition. In some embodiments, the environmental exposure is indicated by an increase or decrease in methylation of certain genomic regions, an increase or decrease of histone binding to certain genomic regions, and/or an increase or decrease of transcription factor binding to certain genomic regions. In certain preferred embodiments, the nucleic acids are RNA molecules and a change in RNA expression, RNA splicing, RNA base modifications, and/or RNA secondary structure is indicative of the environmental exposure.

In certain aspects, method for identifying a strain of microorganism is provided. Such methods preferably comprise sequencing epigenetic markers isolated from the microorganism to determine an epigenetic genotype for the microorganism, and identifying the strain of microorganism based on the epigenetic genotype, wherein the sequencing generates a set of sequence reads comprising both base sequence data and modification data. The microorganism can optionally be a virus, bacteria, archaean, protozoan, or a fungus, and can be pathogenic or nonpathogenic.

Some aspects of the invention provide methods for determining expression profiles. In preferred embodiments, such a method comprises isolating DNA from an organism; sequencing the DNA to generate sequence reads comprising both sequence data and epigenetic modification data; identifying genes in the DNA based upon the sequence data; and determining which of the genes so identified are being expressed based upon the epigenetic modification data. The DNA is optionally derived from portions of a genome known to contain genes involved in a disease or metabolic pathway of interest, and the disease can be any disease that is affected by epigenetic modifications, e.g., cancer, diabetes, heart disease, or organ rejection. In certain preferred embodiments, the DNA is derived from multiple different tissues.

Methods of identifying mRNA expression are also provided in some aspects of the invention. For example, a method of identifying mRNA expression can comprise growing a cell culture in the presence of modified rNTPs; isolating mRNA molecules from the cell culture; sequencing the mRNA molecules to provide sequence reads comprising both sequence and modification data; and identifying which of the mRNA molecules have incorporated the modified rNTPs, thereby identifying mRNA expression in the cell culture.

Further, methods of distinguishing between a sequence read from a first source and a sequence read from a second source are also provided by certain aspects of the invention. In one such embodiment, the method comprises providing a single reaction mixture comprising both a first nucleic acid from a first source and a second nucleic acid from a second source; simultaneously subjecting the first nucleic acid and the second nucleic acid in the single reaction mixture to a single-molecule real time sequencing reaction that generates sequence reads comprising both base sequence data and modification sequence data; and analyzing the sequence reads, wherein a first subset of the sequence reads is determined to have both sequence data and modification data consistent with the first source, and a second subset of the sequence reads is determined to have both sequence data and modification data consistent with the second source, thereby distinguishing between sequence reads from the first source and sequence reads from the second source.

The invention also provides, in some aspects, methods for differentiating nucleic acids from different sources that comprise treating a first nucleic acid from a first source with a modifying agent to generate a treated nucleic acid; providing a single reaction mixture comprising the treated nucleic acid and a second nucleic acid from a second source; subjecting the single reaction mixture to a single analytical reaction, wherein the single analytical reaction provides both sequence data and modification data for both the treated nucleic acid and the second nucleic acid; analyzing the sequence data to determine a set of sequence reads; and analyzing the modification data to identify which of the set of sequence reads corresponds to the treated nucleic acid and which of the set of sequence reads corresponds to the second nucleic acid, thereby differentiating the first nucleic acid from the second nucleic acid.

In still further aspects, methods are provided for a generating a haplotype comprising both sequence data and base modification data. A preferred embodiment of such a method comprises fragmenting a genomic DNA sample to generate fragments at least 2 kb in length, wherein a product of the fragmenting is a fragment comprising a region of interest; subjecting the fragment to a single-molecule sequencing reaction to generate a single sequence read that extends the full length of the fragment comprising the region of interest, wherein the single sequence read comprises base sequence information and kinetic information that is indicative of modified bases within the fragment; and analyzing the base sequence information and the kinetic information in the single sequence read to determine a base sequence for the region of interest and an identification and location of modified bases within the region of interest, thereby generating a haplotype for the region of interest that comprises both sequence data and base modification data. In certain embodiments, a plurality of fragments comprising the region of interest are each subjected to a single-molecule sequencing reaction to generate a plurality of single sequence reads, and the analyzing further comprises generating a plurality of haplotypes for the region of interest, and further constructing a consensus haplotype sequence from the plurality of haplotypes. The genomic DNA sample optionally comprises one or a combination of human DNA, bacterial DNA, viral DNA, fungal DNA, a forensic DNA sample, a patient's DNA sample, a diagnostic DNA sample, a prognostic DNA sample, embryonic DNA, and DNA from a cancer cell, e.g., from a tumor or metastatic cell, e.g., in a blood sample.

In still further aspects, methods are provided for assembling sequence reads from different nucleic acid fragments to generate a single contig for an entire bacterial chromosome. Preferred embodiments of such methods comprise synchronizing bacterial cells that are actively growing, and titrating an amount of a modified base into the culture medium such that the amount of the modified base incorporated into newly replicated chromosomes is significantly different during different points during replication of the bacterial chromosome, thereby generating newly synthesized bacterial chromosomes having a significantly different amount of the modified base incorporated near the origin than near the ter sequence; fragmenting the newly synthesized bacterial chromosomes to generate chromosomal fragments; subjecting the chromosomal fragments to single-molecule sequencing reactions to generate a set of sequence reads comprising both sequence data and modification data for the chromosomal fragments; analyzing the sequence data to determine a nucleotide sequence for each chromosomal fragment; analyzing the modification data to determine an amount of modified bases in each chromosomal fragment; and based on the sequence data and modification data, assembling the set of sequence reads to generate a single contig for the entire bacterial chromosome.

DETAILED DESCRIPTION OF THE INVENTION

I. General

Figure 1:
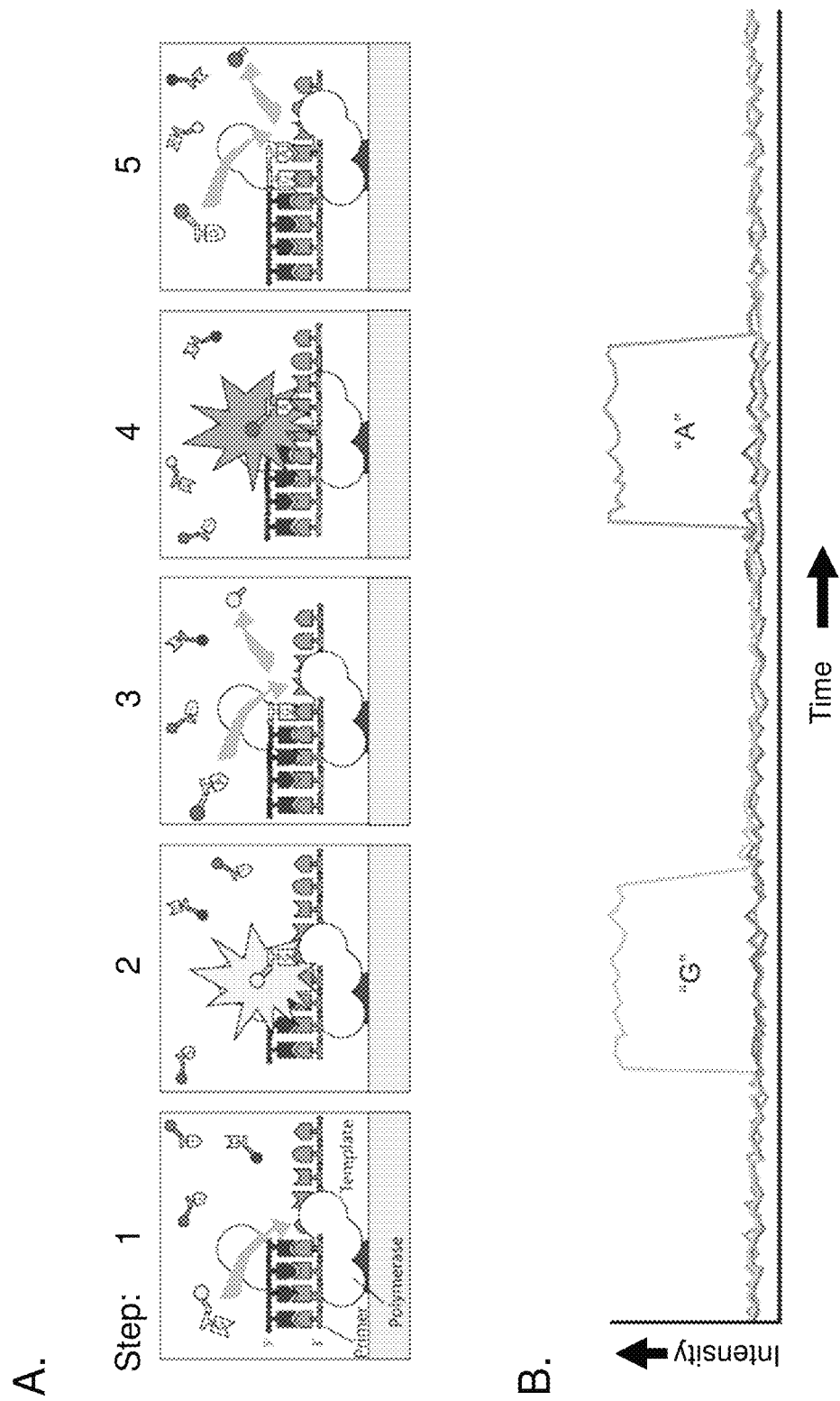
FIG. 1 provides an exemplary illustration of single-molecule, real-time (SMRT®) nucleic acid sequencing.
Figure 2:
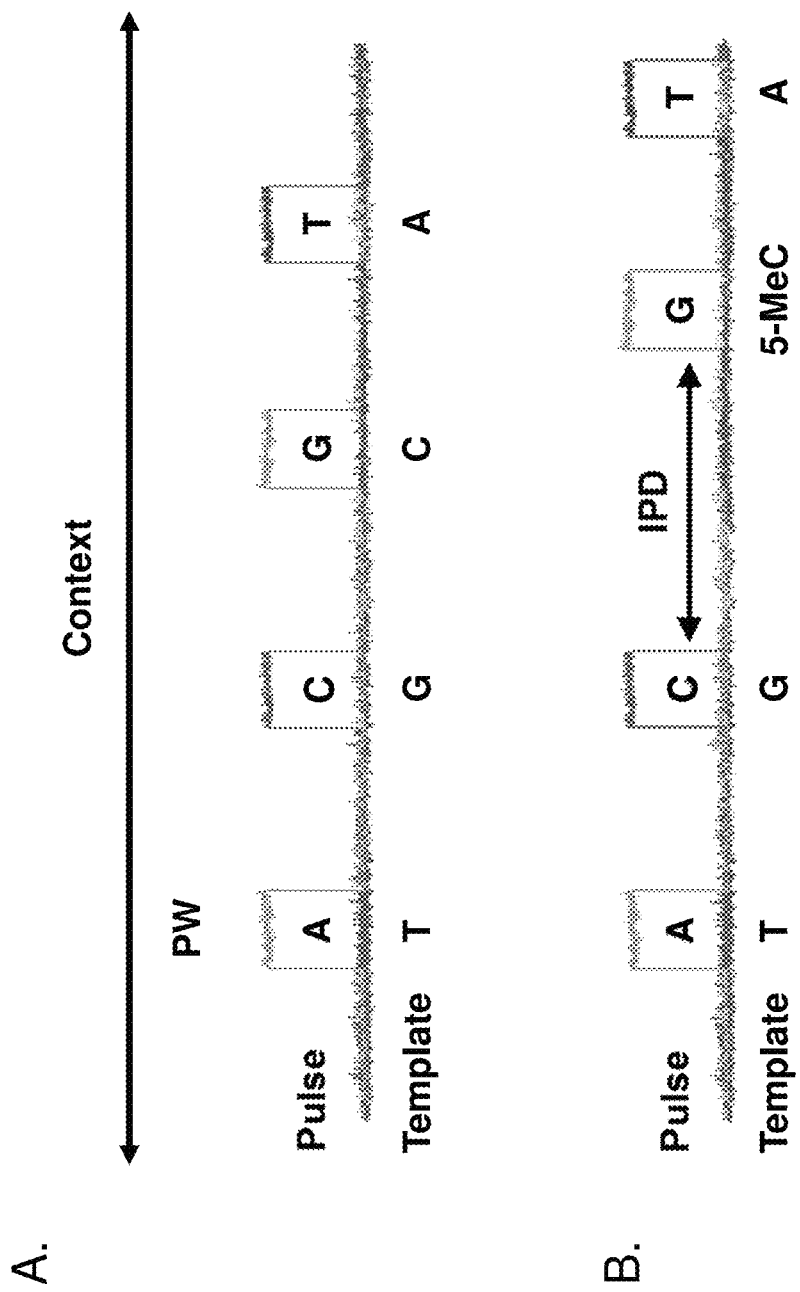
FIG. 2 provides illustrative examples of various types of reaction data in the context of a pulse trace.

The present invention is generally directed to methods and compositions useful in simultaneous detection of base sequences and modifications (e.g., epigenetic modifications, DNA damage, etc.) within nucleic acid sequences. In particularly preferred aspects, modified nucleotides within sequence templates are detected during nucleic acid sequencing reactions through the use of single molecule nucleic acid analysis such that the resulting sequence read(s) comprises both nucleotide base ("nucleobases") sequence data and base modification data. In preferred embodiments, kinetic information in the sequence data is indicative of not only the position of a modified base, but also the type of base modification, without the need to compare to other sequence reads where that have been treated to provide base sequence differences that are used to determine the presence of a modified base, e.g., in conventional bisulfite sequencing. As such, a single read from a single molecule, or a plurality of reads from the single molecule, is sufficient to provide both the base sequence, as well as location and identity of modified bases, for a single template nucleic acid. The ability to detect modifications within nucleic acid sequences is useful for mapping such modifications in various types and/or sets of nucleic acid sequences, e.g., across a set of mRNA transcripts, across a chromosomal region of interest, or across an entire genome. The modifications so mapped can then be related to transcriptional activity, secondary structure of the nucleic acid, siRNA activity, mRNA translation dynamics, kinetics and/or affinities of DNA- and RNA-binding proteins, and other aspects of nucleic acid (e.g., DNA and/or RNA) metabolism.

Further, modifications in genomic sequences can also be indicative of certain biologically important characteristics of the organism from which the genomic sequences were isolated. For example, patterns of modified bases can be used to a) identify a particular bacterial strain or isolate, b) distinguish between different cell types in a sample, e.g., biopsy, or c) inform on the health status of an organism. These examples are not meant to be limiting, and these and further examples are described in greater detail in the descriptions that follow.

In preferred embodiments, detection of modifications within nucleic acid molecules ("templates") does not require amplification or copying of the molecules prior to detection. In fact, in some cases amplification of nucleic acid molecules results in nucleic acid products of such amplification that are lacking the modification to be detected. In further preferred embodiments, detection of modifications within nucleic acid molecules as described herein does not require further modification to the nucleic acid molecules prior to detection. In particular, treatment with bisulfite is not typically required for detection of methylated bases. However, certain embodiments described herein do comprise amplification and/or nucleic acid modifying agents, so their use is not excluded from all embodiments of the methods of the instant invention.

Although certain embodiments of the invention are described in terms of detection of modified nucleotides or other modifications in a single-stranded DNA molecule (e.g., a single-stranded template DNA), various aspects of the invention are applicable to many different types of nucleic acids, including e.g., single- and double-stranded nucleic acids that may comprise DNA (e.g., genomic DNA, mitochondrial DNA, viral DNA, etc.), RNA (e.g., mRNA, siRNA, microRNA, rRNA, tRNA, snRNA, ribozymes, etc.), RNA-DNA hybrids, PNA, LNA, morpholino, and other RNA and/or DNA hybrids, analogs, mimetics, and derivatives thereof, and combinations of any of the foregoing. Nucleic acids for use with the methods, compositions, and systems provided herein may consist entirely of native nucleotides, or may comprise non-natural or non-cognate bases/nucleotides (e.g., synthetic and/or engineered) that may be paired with native nucleotides or may be paired with the same or a different non-natural or non-cognate base/nucleotide. In certain preferred embodiments, the nucleic acid comprises a combination of single-stranded and double-stranded regions, e.g., such as the templates described in U.S. Ser. Nos. 12/383,855 and 12/413,258, both filed on Mar. 27, 2009 and incorporated herein by reference in their entireties for all purposes. In particular, mRNA modifications are difficult to detect by technologies that require reverse transcriptase PCR amplification because such treatment does not maintain the modification in the amplicons. The present invention utilizes methods for analyzing modifications in RNA molecules that do not require such amplification. More generally, in certain embodiments, methods are provided that do not require amplification of a modification-containing nucleic acid.

Generally speaking, the methods of the invention involve monitoring of an analytical reaction to collect "reaction data," wherein the reaction data is indicative of the progress of the reaction. Reaction data includes data collected directly from the reaction, as well as the results of various manipulations of that directly collected data, any or a combination of which can serve as a signal for the presence of a modification in the template nucleic acid. Reaction data gathered during a reaction is analyzed to identify characteristics indicative of the presence of a modification, and typically such data comprises changes or perturbations relative to data generated in the absence of the modification. For example, certain types of reaction data are collected in real time during the course of the reaction, such as metrics related to reaction kinetics, affinity, rate, processivity, signal characteristics, error types and rates thereof, and the like. As used herein, "kinetics," "kinetic signature," "kinetic response," "activity," and "behavior" of a reaction component (e.g., an enzyme, binding agent, etc.) or the reaction as a whole generally refer to reaction data related to the progression of the reaction under investigation and are often used interchangeably herein. Signal characteristics vary depending on the type of analytical reaction being monitored. Signal characteristics can refer to detection of luminescent or fluorescent emissions, changes in current or resistance, fluctuations in pH in the reaction mixture, and the like. For example, some reactions use detectable labels to tag one or more reaction components, and signal characteristics for a detectable label include, but are not limited to, the type of signal (e.g., wavelength, charge, etc.) and the shape of the signal (e.g., height, width, curve, etc.). Other reactions use the magnitude of a change in current flowing through a biological and/or solid-state nano-scale hole ("nanopore") to detect passage of molecules (e.g., nucleotide bases, singly or within a polynucleotide molecule) thorough the hole. Different analytes cause different disruptions in current through the nanopore, and the characteristics of these disruptions can be used to detect passage of a particular analyte. Further, signal characteristics for multiple signals (e.g., temporally adjacent signals) can also be used, including, e.g., the distance between signals during a reaction, the number and/or kinetics of extra signals (e.g., that do not correspond to the progress of the reaction, such as cognate or non-cognate sampling during sequencing-by-synthesis), internal complementarity, and the local signal context (i.e., one or more signal that precede and/or follow a given signal). For example, template-directed sequencing reactions often combine signal data from multiple nucleotide incorporation events to generate a sequence read for a nascent strand synthesized, and this sequence read is used to derive, e.g., by complementarity, the sequence of the template strand. Other types of reaction data are generated from statistical analysis of real time reaction data, including, e.g., accuracy, precision, conformance, error rates, etc. In some embodiments, data from a source other than the reaction being monitored is also used. For example, a sequence read generated during a nucleic acid sequencing reaction can be compared to sequence reads generated in replicate experiments, or to known or derived reference sequences from the same or a related biological source. Alternatively or additionally, a portion of a template nucleic acid preparation can be amplified using unmodified nucleotides and subsequently sequenced to provide an experimental reference sequence to be compared to the sequence of the original template in the absence of amplification. Although certain specific embodiments of the use of particular types of reaction data to detect certain kinds of modifications are described at length herein, it is to be understood that the methods, compositions, and systems are not limited to these specific embodiments. Different types of reaction data can be combined to detect various kinds of modifications, and in certain embodiments more than one type of modification can be detected and identified during a single reaction on a single template. For example, some sequencing reactions involve use of an enzyme to control passage of a nucleic acid through a nanopore, and in such cases reaction data can include both kinetics and other behavior of the enzyme and fluctuations in current through the nanopore. For example, ratchet proteins, helicases, or motor proteins can be used to push or pull a nucleic acid molecule through a hole in a biological or synthetic membrane. The kinetics of these proteins can vary depending on the sequence context of a nucleic acid on which they are acting. For, example, they may slow down or pause at a modified base, and this behavior, captured as a part of the reaction data, is indicative of the presence of the modified base even where the modified base is not within the sensing portion of the nanopore. Such variations to the detailed embodiments of the invention will be clear to one of ordinary skill based upon the teachings provided herein.

In certain embodiments, redundant sequence information is generated and analyzed to detect one or more modifications in a template nucleic acid. Redundancy can be achieved in various ways, including carrying out multiple sequencing reactions using the same original template, e.g., in an array format, e.g., a ZMW array. In some embodiments in which a lesion is unlikely to occur in all the copies of a given template, reaction data (e.g., sequence reads, kinetics, signal characteristics, signal context, and/or results from further statistical analyses) generated for the multiple reactions can be combined and subjected to statistical analysis to determine a consensus sequence for the template. In this way, the reaction data from a region in a first copy of the template can be supplemented and/or corrected with reaction data from the same region in a second copy of the template. Similarly, a template can be amplified (e.g., via rolling circle amplification) to generate a concatemer comprising multiple copies of the template, and the concatemer can be subjected to sequencing, thereby generating a sequencing read that is internally redundant. As such, the sequence data from a first segment of the concatemer (corresponding to a first region of the template) can be supplemented and/or corrected with sequence data from a second segment of the concatemer also corresponding to the first region of the template. Alternatively or additionally, a template can be subjected to repeated sequencing reactions to generate redundant sequence information that can be analyzed to more thoroughly characterize the modification(s) present in the template. In certain embodiments, further benefits are realized by comparing sequence generated from nucleic acids having modifications to the same nucleic acids lacking the modifications. For example, where there is ambiguity in the sequence of a nucleic acid at a given locus, modification of that locus and resequencing of the nucleic acid will provide a further "call" at that locus that will supplement the data provided by the unmodified nucleic acid and allow determination of the true sequence at that locus. Likewise, a template having modifications can be sequenced and subsequently treated to remove the modifications prior to resequencing. Data from the modified and unmodified templates is used together to call the base in question. In both of these strategies, the kinetics of polymerization will change if the modification status of the base changes, and this difference (or lack thereof) is a key aspect of the additional data used to finally determine the sequence at a given position. Of course, these methods are not limited to using a single template molecule in both sequencing reactions, and aliquots of a given sample nucleic acid can be sequenced in parallel, one treated and one untreated, to attain the same type of data sets. Additional information on templates and methods for redundant sequencing of template molecules are described more fully in U.S. Pat. Nos. 7,476,503, 7,906,284, and 7,901,889; U.S. Patent Publication Nos. 20080161194, 20080161195, 20090280538, 20090298075, 20110212436, and 20110281768; and U.S. patent application Ser. No. 13/403,789, filed Feb. 23, 2012, all of which are incorporated herein in their entireties for all purposes.

The term "modification" as used herein is intended to refer not only to a chemical modification of a nucleic acids, but also to a variation in nucleic acid conformation or composition, interaction of an agent with a nucleic acid (e.g., bound to the nucleic acid), and other perturbations associated with the nucleic acid. As such, a location or position of a modification is a locus (e.g., a single nucleotide or multiple contiguous or noncontiguous nucleotides) at which such modification occurs within the nucleic acid. Of particular interest are modifications that have regulatory functions within a genome, e.g., epigenetic modifications. For example, hypermethylation is an epigenetic modification known to reduce or prevent gene expression. For a double-stranded template, a modification may occur in the strand complementary to a nascent strand synthesized by a polymerase processing the template, or may occur in the displaced strand. In some embodiments, a modification can even occur in a base incorporated into a nascent strand during a template-directed sequencing reaction. Although certain specific embodiments of the invention are described in terms of 5-methylcytosine detection, detection of other types of modified nucleotides (e.g., $N^6$-methyladenosine, $N^3$-methyladenosine, $N^7$-methylguanosine, 5-hydroxymethylcytosine, other methylated nucleotides, pseudouridine, thiouridine, isoguanosine, isocytosine, dihydrouridine, queuosine, wyosine, inosine, triazole, diaminopurine, β-D-glucopyranosyloxymethyluracil (a.k.a., 3-D-glucosyl-HOMedU, β-glucosyl-hydroxymethyluracil, "dJ," or "base J"), 8-oxoguanosine (a.k.a., "8-oxoG," 8-oxo-7,8-dihydroguanine, 8-oxoguanine, 7,8-dihydro-8-oxoguanine, and 8-hydroxyguanine), and 2'-O-methyl derivatives of adenosine, cytidine, guanosine, and uridine) are also contemplated. Further, although described primarily in terms of DNA templates, such modified bases can be modified RNA bases and can be detected in RNA (or primarily RNA) templates. These and other modifications are known to those of ordinary skill in the art and are further described, e.g., in Narayan P, et al. (1987) Mol Cell Biol 7(4):1572-5; Horowitz S, et al. (1984) Proc Natl Acad Sci U.S.A. 81(18):5667-71; "RNA's Outfits: The nucleic acid has dozens of chemical costumes," (2009) C&EN; 87(36):65-68; Kriaucionis et al. (2009) Science 324 (5929): 929-30; and Tahiliani, et al. (2009) Science 324 (5929): 930-35; Matray, et al. (1999) Nature 399(6737):704-8; Ooi, et al. (2008) Cell 133: 1145-8; Petersson, et al. (2005) J Am Chem Soc. 127(5):1424-30; Johnson, et al. (2004) 32(6):1937-41; Kimoto, et al. (2007) Nucleic Acids Res. 35(16):5360-9; Ahle, et al. (2005) Nucleic Acids Res 33(10):3176; Krueger, et al., Curr Opinions in Chem Biology 2007, 11(6):588); Krueger, et al. (2009) Chemistry & Biology 16(3):242; McCullough, et al. (1999) Annual Rev of Biochem 68:255; Liu, et al. (2003) Science 302(5646):868-71; Limbach, et al. (1994) Nucl. Acids Res. 22(12):2183-2196; Wyatt, et al. (1953) Biochem. J. 55:774-782; Josse, et al. (1962) J. Biol. Chem. 237:1968-1976; Lariviere, et al. (2004) J. Biol. Chem. 279:34715-34720; and in International Application Publication No. WO/2009/037473, the disclosures of which are incorporated herein by reference in their entireties for all purposes. Modifications further include the presence of non-natural (e.g., non-standard, non-cognate, synthetic, etc.) base pairs in the template nucleic acid, including but not limited to hydroxypyridone and pyridopurine homo- and hetero-base pairs, pyridine-2,6-dicarboxylate and pyridine metallo-base pairs, pyridine-2,6-dicarboxamide and a pyridine metallo-base pairs, metal-mediated pyrimidine base pairs T-Hg(II)-T and C—Ag(I)—C, and metallo-homo-basepairs of 2,6-bis (ethylthiomethyl)pyridine nucleobases Spy, 6-amino-5-nitro-3-(1'-β-D-2'-deoxyribofuranosyl)-2(1H)-pyridone (dZ), 2-amino-8-(1'-β-D-2'-deoxyribofuranosyl)-imidazo[1,2-a]-1,3,5-triazin-4(8H)-one (dP), and alkyne-, enamine-, alcohol-, imidazole-, guanidine-, and pyridyl-substitutions to the purine or pyridimine base (Wettig, et al. (2003) J Inorg Biochem 94:94-99; Clever, et al. (2005) Angew Chem Int Ed 117:7370-7374; Schlegel, et al. (2009) Org Biomol Chem 7(3):476-82; Zimmerman, et al. (2004) Bioorg Chem 32(1): 13-25; Yanagida, et al. (2007) Nucleic Acids Symp Ser (Oxf) 51:179-80; Zimmerman (2002) J Am Chem Soc 124(46): 13684-5; Buncel, et al. (1985) Inorg Biochem 25:61-73; Ono, et al. (2004) Angew Chem 43:4300-4302; Lee, et al. (1993) Biochem Cell Biol 71:162-168; Loakes, et al. (2009), Chem Commun 4619-4631; Yang, et al. (2007) Nucleic Acids Res. 35(13):4238-4249; Yang, et al. (2006) Nucleic Acids Res. 34(21):6095-6101; Geyer, et al. (2003) Structure 11: 1485-1498; and Seo, et al. (2009) J Am Chem Soc 131:3246-3252, all incorporated herein by reference in their entireties for all purposes). Other types of modifications include, e.g, a nick, a missing base (e.g., apurinic or apyridinic sites), a ribonucleoside (or modified ribonucleoside) within a deoxyribonucleoside-based nucleic acid, a deoxyribonucleoside (or modified deoxyribonucleoside) within a ribonucleoside-based nucleic acid, dUTP, rTTP, a pyrimidine dimer (e.g., thymine dimer or cyclobutane pyrimidine dimer), a cis-platin crosslinking, oxidation damage, hydrolysis damage, other methylated bases, bulky DNA or RNA base adducts, photochemistry reaction products, interstrand crosslinking products, mismatched bases, and other types of "damage" to the nucleic acid. As such, certain embodiments described herein refer to "damage" and such damage is also considered a modification of the nucleic acid in accordance with the present invention. Modified nucleotides can be caused by exposure of the DNA to radiation (e.g., UV), carcinogenic chemicals, crosslinking agents (e.g., formaldehyde), certain enzymes (e.g., nickases, glycosylases, exonucleases, methylases/methyltransferases (e.g., m4C methyltransferase, DAM, etc.), other nucleases, glucosyltransferases, etc.), viruses, toxins and other chemicals, thermal disruptions, and the like. Modified nucleotides can be found in native nucleic acids, can be added by treatment in vitro, or cells can be engineered to introduce such modifications in vivo, e.g., by transformation with an appropriate modification-introducing agent, such as the enzymes listed above.

A preferred enzyme for use with certain methods described herein is a non-specific adenine methyltransferase described in U.S. Provisional Patent Application No. 61/599,230, filed Feb. 15, 2012, and incorporated herein by reference in their entireties for all purposes. Various methods can be used to identify such a methyltransferase, such as those described in Fang, et al. (2012) Nature Biotechnology 30(12):1232-1239, which is incorporated herein by reference in its entirety for all purposes. Methyltransferases having specific recognition sequences or "motifs" have been used for chromatin mapping. A chromatin sample is treated with such an enzyme, which introduces methyl groups on exposed or accessible portions of the chromatin. Subsequent detection of methyl groups provides data on which regions of the nucleic acid within the chromatin were accessible to the methyltransferase, but only where those portions comprise a sequence motif that is recognized by the particular methyltransferase being used. As such, exposed portions lacking the sequence motif would not be detectable by this method. In contrast, by using a nonspecific methyltransferase rather than a sequence-specific methyltransferase, the "methyl labeling" of the nucleic acid component of the chromatin would not be dependent upon a recognition sequence in the exposed nucleic acids, thereby allowing detection of accessible regions without a particular recognition sequence, as long as a "methylatable nucleoside" (e.g., C or A) is present. In certain preferred embodiments, the enzyme is a 6-mA methyltransferase, in other embodiments it is a 4-mC methylatransferase, in further embodiments it is a phosphorothioate modification enzyme, and in still further embodiments a combination of such modification enzymes is used to identify accessible nucleic acid regions within a chromatin molecule.

In vivo, DNA damage is a major source of mutations leading to various diseases including cancer, cardiovascular disease, and nervous system diseases (see, e.g., Lindahl, T. (1993) Nature 362(6422): 709-15, which is incorporated herein by reference in its entirety for all purposes). The methods and systems provided herein can also be used to detect various conformations of DNA, in particular, secondary structure forms such as hairpin loops, stem-loops, internal loops, bulges, pseudoknots, base-triples, supercoiling, internal hybridization, and the like; and are also useful for detection of agents interacting with the nucleic acid, e.g., bound proteins such as chromatin components (e.g., histones, RNAs, etc.), transcription factors, regulatory proteins or RNAs, replication factors, or other moieties.

Further, nucleic acids known to have or suspected of having one or more modifications of interest can be targeted, e.g., using antibodies or other binding agents specific to the one or more modifications, and the nucleic acids containing the one or more modifications can be selected or "captured" by various methods known in the art, e.g., immunoprecipitation, column chromatography, bead separations, etc. Once the nucleic acids that do not contain the one or more modifications are removed, e.g., by washing, buffer exchange, etc., the selected nucleic acids can be subjected to template-directed or other sequencing to identify and/or map the one or more modifications. For example, affinity purification can be utilized to isolate nucleic acids comprising a modification of interest. Affinity purification makes use of specific binding interactions between molecules. In certain preferred methods, a particular ligand is chemically immobilized or coupled to a solid support (e.g., column) so that when a complex mixture is passed over the support those molecules having specific binding affinity to the ligand become bound. After other components of the mixture are washed away, the bound molecule is stripped from the support, resulting in its purification from the original complex mixture. It is within the skill of the ordinary artisan to determine a ligand that has a specific binding affinity for a modification of interest, and such ligands can include, without limitation, antibodies, enzymes, nucleic acids, nucleic acid binding agents, fusion proteins, and the like. Further, prior to affinity purification, the modification of interest may be subjected to a treatment that adds a tag to facilitate purification, e.g., an antigen, binding partner, protein tag, etc. Affinity purification methods, tags, and supports are well known, widely used, and commercially available for use by those of ordinary skill in the art.

In certain aspects, the described methods and compositions involve detection of modifications within a single template molecule during sequencing, as well as determination of their location (i.e. "mapping") within the template molecule. In certain preferred embodiments, high-throughput, real-time, single-molecule, template-directed sequencing assays are used to detect the presence of such modified sites and to determine their location on the DNA template, e.g., by monitoring the progress and/or kinetics of a polymerase enzyme processing the template. For example, when a polymerase enzyme encounters certain types of damage or other modifications in a DNA template, the progress of the polymerase can be temporarily or permanently blocked, e.g., resulting in a paused or dissociated polymerase. As such, the detection of a pause in or termination of nascent strand synthesis is indicative of the presence of such damage or lesion. Similarly, certain types of modifications cause other perturbations in the activity of the polymerase, such as changes in the kinetics of nascent strand synthesis, e.g., changes in pulse width or interpulse duration. Yet further, some modifications cause changes in the enzyme activity that are detectable as changes in the error metrics of the enzyme during template-directed polymerization. By analysis of the sequence reads produced prior to the change or perturbation in activity of the polymerase, and alternatively or additionally after reinitiation of synthesis, one can map the site of the damage or lesion on the template. Since different types of lesions can have different effects on the progress of the polymerase on the substrate, in certain cases the behavior of the polymerase on the template not only informs as to where the lesion occurs, but also what type of lesion is present. Preferred sequencing methods for detection of modified bases during real-time sequencing are described at length in U.S. Patent Publication No. 20110183320; PCT Patent Application No. PCT/US2011/060338 (WO 2012065043); Clark, et al. (2013) BMC Biology 11:4 doi:10.1186/1741-7007-11-4; Lluch-Senar, et al. (2013) PLoS Genet 9(1): e1003191. doi:10.1371/journal.pgen.1003191; Fang, et al. (2012) Nature Biotechnology 30:1232-1239; Ynull, et al. (2012) Genome Biology 13:175; Schadt, et al. (2012) Genome Research doi:10.1101/gr.136739.111; Murray, et al. (2012) Nucl. Acids Res. doi: 10.1093/nar/gks891; Clark, et al. (2011) Genome Integrity 2:10 doi:10.1186/2041-9414-2-10; Clark, et al. (2011) Nucl. Acids Res. doi: 10.1093/nar/gkr1146; Song, et al. (2011) Nature Methods doi:10.1038/nmeth.1779; and Flusberg, et al. (2010) Nature Methods doi:10.1038/nmeth.1459, the disclosures of which are incorporated herein by reference in their entireties for all purposes.

While certain compositions and method provided herein are described in terms of sequencing reactions that utilize single-molecule, real-time, polymerase-mediated, template-directed nascent strand synthesis, the present invention is not limited to use of these sequencing reactions and other sequencing technologies capable of providing reaction data indicative of a modification within a template are also contemplated. For example, in certain preferred embodiments, real-time, single-molecule, electrical-detection-based sequencing assays are used to detect the presence of such modified sites and to determine their location on the DNA template, e.g., by monitoring the progress and/or kinetics of the passage of a nucleic acid template through a constriction through which a current flows. The presence of the template within the passage (e.g., nanopore or other nano-scale hole, e.g., pore protein or synthetically-engineered nanohole) perturbs the current flow in a sequence-specific manner to provide a signal for identifying which nucleotide base is in a "detection region" within the hole. The speed at which the template passes through the hole depends on various factors, including the force used to push or pull the template through the hole, the relative size of the hole, and the sequence of bases within the template strand. For example, a base comprising a bulky modification, e.g., methyl groups, sugar moieties, and the like, is expected to perturb the current to a greater degree than a non-modified base, providing a relatively greater signal than that of the non-modified base, based at least on steric hindrance caused by the larger size of the modified base. Yet further, the mechanism by which the template is pushed or pulled through the hole is clearly a major factor in the kinetics of passage, and that mechanism can be affected by the presence of modified bases. For example, in certain embodiments a helicase is used to unwind a double-stranded nucleic acid and send one of the two strands into the hole to be detected. Where modifications present in the duplex molecule inhibit unwinding by the helicase, the kinetics of passage will slow and a longer transition from one base to the next will be detectable within the nanohole. Likewise, and as described for the sequencing-by-synthesis reactions above, the kinetics of a polymerase enzyme that is processing a template is affected by base modifications. As such, the kinetics of nanohole sequencing reactions that use a secondary "driving" mechanism, e.g., an enzyme (polymerase, helicase, etc.), motor protein, ratchet protein, and the like) to drive a template strand through the nanohole will be impacted by the effect of modifications on the driving mechanism or "driver." Further, since the kinetic changes at the driver are uncoupled from the subsequent detection of the modified bases themselves as they pass through the nanopore, analysis of the kinetics of such a sequencing strategy will need to account for not only the current and kinetic effects within the nanopore, but also factor in kinetic effects at the driver. As such, single-molecule, real-time sequencing technologies include not only polymerase-mediated sequencing-by-synthesis reactions, but also nanopore-based sequencing technologies, and preferred methods are those that are able to detect modifications (e.g., within a template molecule) during a sequencing reaction in which the base identities are also determined. By analysis of the base and modification data within the sequence reads, one can map the site of the damage or lesion on the template. These and other aspects of the invention are described in greater detail in the description and examples that follow.

II. Single Molecule Sequencing

In certain aspects of the invention, single molecule real time sequencing systems are applied to the detection of modified nucleic acid templates through analysis of the reaction data (e.g., sequence and/or kinetic data) derived from such systems. In particular, modifications in a template nucleic acid strand can cause unique and identifiable alterations in an analytical reaction that allow the modifications to be identified. For example, in certain embodiments, modifications in a template nucleic acid strand alter the enzymatic activity of a nucleic acid polymerase in various ways, e.g., by increasing the time for a bound nucleobase to be incorporated and/or increasing the time between incorporation events. The alteration in enzymatic activity can optionally be detected using a nucleic acid sequencing technology that detects incorporation of nucleotides (e.g., comprising a detectable label) into a nascent strand in real time. Such methods are described in detail in International Patent Application No. PCT/US2011/060338, filed Nov. 11, 2011, and incorporated herein by reference in its entirety for all purposes. In other embodiments, modifications in a template change the way in which the current through a nanopore is perturbed during passage of the template. In preferred embodiments, such modifications are detected using a single molecule nucleic acid sequencing technology, where a sequence read generated corresponds to a single molecule of a nucleic acid template. In preferred embodiments, a single molecule nucleic acid sequencing technology is capable of real-time detection of individual nucleotides, e.g. during nucleotide incorporation or passage through a nanohole. Such sequencing technologies are known in the art and include, e.g., the SMRT® sequencing and nanopore sequencing technologies. For more information on nanopore sequencing, see, e.g., U.S. Pat. No. 5,795,782; Kasianowicz, et al. (1996) Proc Natl Acad Sci USA 93(24):13770-3; Ashkenas, et al. (2005) Angew Chem Int Ed Engl 44(9): 1401-4; Howorka, et al. (2001) Nat Biotechnology 19(7): 636-9; Astier, et al. (2006) J Am Chem Soc 128(5):1705-10; U.S. Ser. No. 13/083,320, filed Apr. 8, 2011; and Zhao, et al. (2007) Nano Letters 7(6):1680-1685, all of which are incorporated herein by reference in their entireties for all purposes.

With regards to nucleic acid sequencing, the term "template" refers to a nucleic acid molecule subjected to a sequencing reaction. For example, in a sequencing-by-synthesis reaction a template is the molecule used by a polymerase to direct synthesis of the nascent strand; e.g., it is complementary to the nascent strand being produced. In a nanopore-based sequencing method, the template is the nucleic acid passed through the nanopore, whether intact or after nucleolytic degradation. A template may comprise, e.g., DNA, RNA, or analogs, mimetics, derivatives, or combinations thereof, as described elsewhere herein. Further, a template may be single-stranded, double-stranded, or may comprise both single- and double-stranded regions. For sequencing technologies that interrogate a single strand of a double-stranded template, the "template strand" is the strand that is interrogated, e.g., passed through a nanopore, used to synthesize a nascent strand, or hybridized to sequence-specific probes (as in SOLiD® sequencing). A modification in a double-stranded template may be in the strand subjected to interrogation, or in the complementary strand. For example, the modification may be present in a strand used by a polymerase to generate a complementary strand, or may be in a complementary strand that is displaced by the polymerase. Yet further, the modification may be in a strand passed through a nanopore, or in a complementary strand that is displaced from the strand passed through the nanopore, such as where the modification affect the kinetics of displacement, e.g., by a ratchet protein, helicase, polymerase, etc. In such a case, the modification can be detected without having been passed through the hole. Simply put, a modification being detected may occur in a template strand or a complement thereof.

Certain direct modification sequencing methods can be performed using single-molecule real-time sequencing systems, e.g., that illuminate and observe individual reaction complexes continuously over time, such as those developed for SMRT® sequencing (see, e.g., P. M. Lundquist, et al., Optics Letters 2008, 33, 1026, which is incorporated herein by reference in its entirety for all purposes). The foregoing SMRT® sequencing instrument generally detects fluorescence signals from an array of thousands of ZMWs simultaneously, resulting in highly parallel operation. Each ZMW, separated from others by distances of a few micrometers, represents an isolated sequencing chamber for a single polymerase acting upon a single template nucleic acid molecule. Other single-molecule, real-time sequencing methods and systems are also applicable to the methods herein, including without limitation those described in U.S. Ser. No. 13/083,320, filed Apr. 8, 2011; and U.S. Patent Publication No. 20120014832, the disclosures of which are incorporated herein by reference in their entireties for all purposes.

Detection of single molecules or molecular complexes in real time, e.g., during the course of an analytical reaction, generally involves direct or indirect disposal of the analytical reaction such that each molecule or molecular complex to be detected is individually resolvable. In this way, each analytical reaction can be monitored individually, even where multiple such reactions are immobilized on a single support, e.g., substrate, membrane, or other surface. Individually resolvable configurations of analytical reactions can be accomplished through a number of mechanisms, and typically involve immobilization of at least one component of a reaction at a reaction site, e.g, a ZMW or nanopore (which can be considered both a component of the reaction and the reaction site itself). Various methods of providing individually resolvable configurations are known in the art, e.g., see European Patent No. 1105529 to Balasubramanian, et al.; and Published International Patent Application No. WO 2007/041394, the full disclosures of which are incorporated herein by reference in their entireties for all purposes. A reaction site on a substrate is generally a location on the substrate at which a single analytical reaction (e.g., comprising a single template molecule) is performed and monitored, preferably in real time. A reaction site may be on a planar surface of the substrate, or may be in an aperture in the surface of the substrate, e.g., a well, nanohole, or other aperture. In preferred embodiments, such apertures are "nanoholes," which are nanometer-scale holes or wells that provide structural confinement of analytic materials of interest within a nanometer-scale diameter, e.g., ~1-300 nm. In some embodiments, such apertures comprise optical confinement characteristics, such as zero-mode waveguides, which are also nanometer-scale apertures and are further described elsewhere herein. Typically, the observation volume (i.e., the volume within which detection of the reaction takes place) of such an aperture is at the attoliter ($10^{-18}$ L) to zeptoliter ($10^{-21}$ L) scale, a volume suitable for detection and analysis of single molecules and single molecular complexes.

The immobilization of a component of an analytical reaction can be engineered in various ways. For example, an enzyme (e.g., polymerase, reverse transcriptase, kinase, etc.) may be attached to the substrate at a reaction site, e.g., within an optical confinement or other nanometer-scale aperture. In other embodiments, a substrate in an analytical reaction (for example, a nucleic acid template, e.g., DNA, RNA, or hybrids, analogs, derivatives, and mimetics thereof, or a target molecule for a kinase) may be attached to the substrate at a reaction site. Certain embodiments of template immobilization are provided, e.g., in U.S. patent application Ser. No. 12/562,690, filed Sep. 18, 2009 and incorporated herein by reference in its entirety for all purposes. One skilled in the art will appreciate that there are many ways of immobilizing nucleic acids and proteins into an optical confinement, whether covalently or non-covalently, via a linker moiety, or tethering them to an immobilized moiety. These methods are well known in the field of solid phase synthesis and micro-arrays (Beier et al., Nucleic Acids Res. 27:1970-1-977 (1999)). Non-limiting exemplary binding moieties for attaching either nucleic acids or polymerases to a solid support include streptavidin or avidin/biotin linkages, carbamate linkages, ester linkages, amide, thiolester, (N)-functionalized thiourea, functionalized maleimide, amino, disulfide, amide, hydrazone linkages, among others. Antibodies that specifically bind to one or more reaction components can also be employed as the binding moieties. In addition, a silyl moiety can be attached to a nucleic acid directly to a substrate such as glass using methods known in the art. In yet further embodiments, a reaction is localized to a given position by virtue of the presence of a hole (e.g., nanopore) through with a template molecule passes during an analytical reaction.

In some embodiments, a nucleic acid template is immobilized onto a reaction site (e.g., within an optical confinement) by attaching a primer comprising a complementary region at the reaction site that is capable of hybridizing with the template, thereby immobilizing it in a position suitable for monitoring. In certain embodiments, an enzyme complex is assembled in an optical confinement, e.g., by first immobilizing an enzyme component. In other embodiments, an enzyme complex is assembled in solution prior to immobilization. Where desired, an enzyme or other protein reaction component to be immobilized may be modified to contain one or more epitopes for which specific antibodies are commercially available. In addition, proteins can be modified to contain heterologous domains such as glutathione S-transferase (GST), maltose-binding protein (MBP), specific binding peptide regions (see e.g., U.S. Pat. Nos. 5,723,584, 5,874,239 and 5,932,433), or the Fc portion of an immunoglobulin. The respective binding agents for these domains, namely glutathione, maltose, and antibodies directed to the Fc portion of an immunoglobulin, are available and can be used to coat the surface of an optical confinement of the present invention. The binding moieties or agents of the reaction components they immobilize can be applied to a support by conventional chemical techniques which are well known in the art. In general, these procedures can involve standard chemical surface modifications of a support, incubation of the support at different temperature levels in different media comprising the binding moieties or agents, and possible subsequent steps of washing and cleaning. In yet further embodiments, a template can be immobilized at a reaction site by binding to an enzyme or other protein (e.g., polymerase, motor protein, helicase, etc.) that serves only to deliver the template to a sequence detector, e.g., a nanopore sensor.

In some embodiments, a substrate comprising an array of reaction sites is used to monitor multiple biological reactions, each taking place at a single one of the reaction sites. Various means of loading multiple biological reactions onto an arrayed substrate are known to those of ordinary skill in the art and are described further, e.g., in U.S. Ser. No. 61/072,641, incorporated herein by reference in its entirety for all purposes. For example, basic approaches include: creating a single binding site for a reaction component at the reaction site; removing excess binding sites at the reaction site via catalytic or secondary binding methods; adjusting the size or charge of the reaction component to be immobilized; packaging or binding the reaction component within (or on) a particle (e.g., within a viral capsid), where a single such particle fits into the relevant reaction site (due to size or charge of the particle and/or observation volume); using non-diffusion-limited loading; controllably loading the reaction component (e.g., using microfluidic or optical or electrical control); sizing or selecting charges in the reaction sites/observation volumes (e.g., the sizes of optical confinements in an array) to control which reaction components will fit (spatially or electrostatically) into which reaction sites/observation volumes; iterative loading of reaction components, e.g., by masking active sites between loading cycles; enriching the activity of the reaction components that are loaded; using self-assembling nucleic acids to sterically control loading; adjusting the size of the reaction site/observation volume; and many others. Such methods and compositions provide for the possibility of completely loading single-molecule array reaction sites (instead of about 30% of such sites as occurs in "Poisson limited" loading methods) with single reaction components (e.g., molecular complexes).

In embodiments utilizing nano-scale holes and current-based detection, such as nanopore methods, it is beneficial to ensure that each detection area on a substrate contains only a single nano-scale aperture. Otherwise, two different templates may be passing through two different holes simultaneously, and the resulting overlapping signals would be difficult if not impossible to resolve. The surface of solid-state nanopores can be treated in order to either improve their sequencing performance or to enable the creation of an hybrid protein/solid-state nanopore. In such a hybrid, the solid-state pore acts a substrate with a hole for the protein nanopore, which would be positioned as a plug within the hole. The protein nanopore would perform the sensing of DNA molecules. This hybrid can the advantages of both types of nanopores: the possibility for batch fabrication, stability, compatibility with micro-electronics, and a population of identical sensing subunits. Unlike methods where a lipid layer much larger than the width of a protein nanopore is used, the hybrid nanopores are generally constructed such that the dimensions of the solid state pore are close to the dimensions of the protein nanopore. The solid state pore into which the protein nanopore is disposed is generally from about 20% larger to about three times larger than the diameter of the protein nanopore. In preferred embodiments the solid state pore is sized such that only one protein nanopore will associate with the solid state pore. An array of hybrid nanopores is generally constructed by first producing an array of solid state pores in a substrate, selectively functionalizing the nanopores for attachment of the protein nanopore, then coupling or conjugating the nanopore to the walls of the solid state pore using liker/spacer chemistry. Techniques and materials for constructing such hybrid nanopores, as well as ensuring a high portion of pores having only one nanopore per solid state pore, are further described in U.S. Ser. No. 13/083,320, filed Apr. 8, 2011, and incorporated herein by reference in its entirety for all purposes.

In preferred aspects, the methods, compositions, and systems provided herein utilize optical confinements to facilitate single molecule resolution of analytical reactions. In preferred embodiments, such optical confinements are configured to provide tight optical confinement so only a small volume of the reaction mixture is observable. Some such optical confinements and methods of manufacture and use thereof are described at length in, e.g., U.S. Pat. Nos. 7,302,146. 7,476,503, 7,313,308, 7,315,019, 7,170,050, 6,917,726, 7,013,054, 7,181,122, and 7,292,742; U.S. Patent Publication Nos. 20080128627, 20080152281, and 200801552280; and U.S. Ser. Nos. 11/981,740 and 12/560, 308, all of which are incorporated herein by reference in their entireties for all purposes.

Where reaction sites are located in optical confinements, the optical confinements can be further tailored in various ways for optimal confinement of an analytical reaction of interest. In particular, the size, shape, and composition of the optical confinement can be specifically designed for containment of a given enzyme complex and for the particular label and illumination scheme used.

In certain preferred embodiments of the invention, single-molecule, real-time sequencing systems already developed are applied to the detection of modified nucleic acid templates through analysis of the sequence and kinetic data derived from such systems. For example, methylated cytosine and other modifications in a template nucleic acid will alter the enzymatic activity of a polymerase processing the template nucleic acid. Other real-time sequencing technologies sensitive to modifications within a template nucleic acid can also be used to detect such modifications, e.g., nanopore sensor sequencing methods. In certain embodiments, polymerase kinetics in addition to sequence read data are detected using a single-molecule nucleic acid sequencing technology, e.g., the SMRT® sequencing technology developed by Pacific Biosciences. This technique is capable of long sequencing reads and can be used to provide high-throughput methylation profiling even in highly repetitive genomic regions, facilitating de novo sequencing of modifications such as methylated bases. SMRT® sequencing systems typically utilize state-of-the-art single-molecule detection instruments, production-line nanofabrication chip manufacturing, organic chemistry, protein mutagenesis, selection and production facilities, and software and data analysis infrastructures. Additional details on single-molecule, real-time microscopy, including sequencing applications, are provided, e.g., in U.S. Pat. Nos. 7,056,661, 7,476, 503, 8,143,030, 7,901,889, and 6,917,726; Eid, J. et al. (2009) *Science* 323, 133; J. Korlach, et al. (2008) *Nucleos. Nucleot. Nucleic Acids* 27, 1072; Lundquist, et al. (2008) *Optics Letters* 33(9): 1026; and Levene, et al. (2003) *Science* 299: 682, all of which are incorporated herein by reference in their entireties for all purposes.

Certain preferred methods of the invention employ real-time sequencing of single DNA molecules (Eid, et al., supra), with intrinsic sequencing rates of multiple bases per second and average read lengths in the 1000 to 10,000 base-pair range. In such sequencing, sequential base additions catalyzed by DNA polymerase into the growing complementary nucleic acid strand are detected with fluorescently labeled nucleotides. The kinetics of base additions and polymerase translocation are sensitive to the structure of the DNA double-helix, which is impacted by the presence of base modifications, e.g, 5-MeC, 5-hmC, base J, etc., and other modifications (secondary structure, bound agents, etc.) in the template. By monitoring the activity of DNA polymerase during sequencing, sequence read information and base modifications can be simultaneously detected. Long, continuous sequence reads that are readily achievable using SMRT® sequencing facilitate modification (e.g., modification) profiling in low complexity regions that are inaccessible to some technologies, such as certain short-read sequencing technologies. Carried out in a highly parallel manner, epigenomes can be sequenced directly, with single base-pair resolution and high throughput.

In preferred embodiments, optical confinements within which a single sequencing reaction takes place are ZMW nanostructures, preferably in an arrayed format. Typically, ZMWs arrays comprise dense arrays of holes, ~100 nm in diameter, fabricated in a ~100 nm thick metal film deposited on a transparent substrate (e.g., silicon dioxide). These structures are further described in the art, e.g., in M. J. Levene, et al., Science 2003, 299, 682; and M. Foquet, et al., J. Appl. Phys. 2008, 103, 034301, the disclosures of which are incorporated herein by reference in their entireties for all purposes. Each ZMW becomes a nanophotonic visualization chamber for recording an individual polymerization reaction, providing a detection volume of just 100 zeptoliters (10-21 liters). This volume represents a ~1000-fold improvement over diffraction-limited confocal microscopy, facilitating observation of single incorporation events against the background created by the relatively high concentration of fluorescently labeled nucleotides. Polyphosphonate and silane-based surface coatings mediate enzyme immobilization to the transparent floor of the ZMW while blocking non-specific attachments to the metal top and side wall surfaces (Eid, et al., supra; and J. Korlach, et al., *Proc Natl Acad Sci USA* 2008, 105, 1176, the disclosures of which are incorporated herein by reference in their entireties for all purposes). While certain methods described herein involve the use of ZMW confinements, it will be readily understood by those of ordinary skill in the art upon review of the teachings herein that these methods may also be practiced using other reaction formats, e.g., on planar substrates or in nanometer-scale apertures other than zero-mode waveguides. (See, e.g., U.S. Ser. No. 12/560,308, filed Sep. 15, 2009; and U.S. Patent Publication No. 20080128627, incorporated herein supra.)

Certain preferred embodiments of a sequencing-by-synthesis reaction to be used with the methods described herein include phospholinked nucleotides comprising a detectable label (e.g., comprising a fluorescent dye) attached to a phosphate group that is removed upon incorporation of the constituent nucleobases into a nascent strand. For example, typically a detectable label is linked to the terminal phosphate, but the label can also be attached to another phosphate group that is not the alpha phosphate, which is incorporated into the sugar-phosphate backbone of the nascent strand. (See, e.g., J. Korlach, et al., Nucleos. Nucleot. Nucleic Acids 2008, 27, 1072, which is incorporated herein by reference in its entirety for all purposes.) Even with 100% replacement of unmodified nucleotides by phospholinked nucleotides, the enzyme cleaves away the label as part of the incorporation process, leaving behind a completely natural, double-stranded nucleic acid product. Each of the four different standard nucleobases (e.g., dATP, dTTP, dCTP, and dGTP, or analogs thereof) is labeled with a distinct detectable label to discriminate base identities during incorporation events, thus enabling sequence determination of the complementary DNA template. During incorporation, the enzyme holds the labeled nucleotide in the ZMW's detection volume for tens of milliseconds, orders of magnitude longer than the average diffusing nucleotide is present. Signal (e.g., fluorescence) is emitted continuously from the detectable label during the duration of incorporation, causing a detectable pulse of increased fluorescence in the corresponding color channel. The pulse is terminated naturally by the polymerase releasing the pyrophosphate-linker-label group. Preferably, the removal of the linker and label during incorporation is complete such that the nucleotide incorporated has no remnants of the linker or label remaining. The polymerase then translocates to the next base, and the process repeats.

The principle of SMRT® sequencing is illustrated in FIG. 1. Briefly, as shown in FIG. 1A, single DNA polymerase molecules with bound DNA template are attached to a substrate, e.g., at the bottom of each zero-mode waveguide. Polymerization of the complementary DNA strand is observed in real time by detecting fluorescently labeled nucleotides. At step 1, the DNA template/primer/polymerase complex is surrounded by diffusing fluorescently labeled nucleotides which probe the active site. A labeled nucleotide makes a cognate binding interaction with the next base in the DNA template that lasts for tens of milliseconds at step 2, during which fluorescence is emitted continuously. At step 3, the polymerase incorporates the nucleotide (nucleobases, alpha phosphate, and sugar group) into the growing nucleic acid chain, thereby cleaving the α-β phosphodiester bond and releasing a labeled polyphosphate. The process repeats for each nucleotide incorporated into the nascent strand at steps 4 and 5, and monitoring the fluorescent signals emitted during the binding and incorporation of a nucleotide into the growing nascent strand provides a sequence of nucleotide incorporations that can be used to derive the sequence of the template nucleic acid. A prophetic trace is shown in FIG. 1B that comprises each step shown in 1A. At steps 2 and 4, a fluorescent signal is emitted during binding and incorporation of a nucleotide into the growing nucleic acid chain, and monitoring of these fluorescent signals provides a sequence of nucleotide incorporations that can be used to derive the sequence of the template nucleic acid. For example, a 5'-G-A-3' sequence in the growing chain indicates a 5'-T-C-3' sequence in the complementary template strand. The detected series of nucleotide incorporations is sometimes called a "sequence read."

As described above, reaction data is indicative of the progress of a reaction and can serve as a signal for the presence of a modification in the template nucleic acid. Reaction data in single molecule sequencing reaction reactions using fluorescently labeled bases is generally centered around characterization of detected fluorescence pulses, a series of successive pulses ("pulse trace" or one or more portions thereof), and other downstream statistical analyses of the pulse and trace data. Fluorescence pulses are characterized not only by their spectrum, but also by other metrics including their duration, shape, intensity, and by the interval between successive pulses (see, e.g., Eid, et al., supra; and U.S. Patent Publication No. 20090024331, incorporated herein by reference in its entirety for all purposes). While not all of these metrics are generally required for sequence determination, they add valuable information about the processing of a template, e.g., the kinetics of nucleotide incorporation and DNA polymerase processivity and other aspects of the reaction. Further, the context in which a pulse is detected (i.e., the one or more pulses that precede and/or follow the pulse) can contribute to the identification of the pulse. For example, the presence of certain modifications alters not only the processing of the template at the site of the modification, but also the processing of the template upstream and/or downstream of the modification. For example, the presence of modified bases in a template nucleic acid has been shown to change the width of a pulse and/or the interpulse duration (IPD), at the modified base and/or at one or more positions proximal to it. A change in pulse width may or may not be accompanied by a change in IPD. In addition, the types of nucleotides or nucleotide analogs being incorporated into a nascent strand can also affect the sensitivity and response of a polymerase to a modification. For example, certain nucleotide analogs increase the sensitivity and/or response of the enzyme as compared to that in the presence of native nucleotides or different nucleotide analogs, thereby facilitating detection of a modification. In particular, nucleotide analogs comprising different types of linkers and/or fluorescent dyes have been shown to have different effects on polymerase activity, and can impact the incorporation of a base into a nascent strand opposite a modification, and/or can impact the incorporation kinetics for a polynucleotide region proximal to (e.g., upstream or downstream of) the modification. The region proximal to the modification can, in certain embodiments, correspond to the region of the template complementary to the portion of the nascent strand synthesized while the footprint of the polymerase overlapped the locus of the modification. These analog-based differences in polymerase sensitivity and response can be used in redundant sequencing strategies to further enhance the detection of modifications. For example, exchanging nucleotide analogs between iterations of an iterative sequencing reaction elicits changes in polymerase activity between the iterations. Statistical analysis of the differences in the sequencing reads from each iteration combined with the knowledge of how each type of nucleotide analog affects polymerase activity can facilitate identification of modifications present in the reaction. FIG. 1 provides illustrative examples of various types of reaction data in the context of a pulse trace including IPD, pulse width (PW), pulse height (PH), and context. FIG. 1A illustrates these reaction data on a pulse trace generated on an unmodified template, and FIG. 1B illustrates how the presence of a modification (5-MeC) can elicit a change in one of these reaction data (IPD) to generate a signal (increased IPD) indicative of the presence of the modification.

Similarly, reaction data in single molecule sequencing reactions using nanopore sensors is generally centered around characterization of changes in current through the nanopore itself, e.g., the rate at which current fluctuations indicate a "next" base in the template is in the detection region of the pore, as well as the magnitude of the current fluctuations themselves as well as all aspects of noise that are measured during those fluctuations. For example, metrics important for nanopore-based sequencing include absolute current flow at a given time, a duration of a given current flow measure, a duration of time the current measure indicates the detection region does not comprise a nucleobases, a duration of time between current measures that are indicative of a particular base, a magnitude of change from a base line current measure, a magnitude of change from a prior of subsequent current measure, and the like. Further, where a protein (e.g., helicase or polymerase) is used to drive the template through the nanopore, interactions of the protein with the template prior to its entry into the pore can affect the kinetics of sequence detection of the portion of the template within the detection region of the pore. In this way, an upstream modified nucleobase can affect detection of an unmodified base within the nanopore.

In yet further embodiments, reaction data is generated by analysis of the collected signals (e.g., fluorescence emissions, current fluctuations, etc.) to determine error metrics for the reaction. Such error metrics include not only raw error rate, but also more specific error metrics, e.g., identification of signals that did not correspond to a nucleobases within the template nucleic acid. For example, for sequencing reactions that involve template-directed nascent strand synthesis using fluorescently labeled nucleotides, this can include identification of pulses that did not correspond to an incorporation event (e.g., due to "sampling"), incorporations that were not accompanied by a detected pulse, incorrect incorporation events, and the like. Any of these error metrics, or combinations thereof, can serve as a signal indicative of the presence of one or more modifications in the template nucleic acid. In some embodiments, such analysis involves comparison to a reference sequence and/or comparison to replicate sequence information from the same or an identical template, e.g., using a standard or modified multiple sequence alignment. Certain types of modifications cause an increase in one or more error metrics. For example, some modifications can be "paired" with more than one type of incoming nucleotide or analog thereof, so replicate sequence reads for the region comprising the modification will show variable base incorporation opposite such a modification. Such variable incorporation is thereby indicative of the presence of the modification. Certain types of modifications cause an increase in one or more error metrics proximal to the modification, e.g., immediately upstream or downstream. The error metrics at a locus or within a region of a template are generally indicative of the type of modification(s) present at that locus or in that region of the template, and therefore serve as a signal of such modification(s). In preferred embodiments, at least some reaction data is collected in real time during the course of the reaction, e.g., pulse and/or trace characteristics. Similarly, error metrics specific for nanopore-based sequencing can be useful for identifying modifications in templates passed through a nanopore sensor.

Although described herein primarily with regards to fluorescently labeled nucleotides, other types of detectable labels and labeling systems can also be used with the methods, compositions, and systems described herein including, e.g., quantum dots, surface enhanced Raman scattering particles, scattering metallic nanoparticles, FRET systems, intrinsic fluorescence, non-fluorescent chromophores, and the like. Such labels are generally known in the art and are further described in Provisional U.S. Patent Application No. 61/186,661, filed Jun. 12, 2009; U.S. Pat. Nos. 6,399,335, 5,866,366, 7,476,503, and 4,981,977; U.S. Patent Pub. No. 2003/0124576; U.S. Ser. No. 61/164,567; WO 01/16375; Mujumdar, et al Bioconjugate Chem. 4(2): 105-111, 1993; Ernst, et al, Cytometry 10:3-10, 1989; Mujumdar, et al, Cytometry 10:1119, 1989; Southwick, et al, Cytometry 11:418-430, 1990; Hung, et al, Anal. Biochem. 243(1):15-27, 1996; Nucleic Acids Res. 20(11):2803-2812, 1992; and Mujumdar, et al, Bioconjugate Chem. 7:356-362, 1996; Intrinsic Fluorescence of Proteins, vol. 6, publisher: Springer US, ©2001; Kronman, M. J. and Holmes, L. G. (2008) Photochem and Photobio 14(2): 113-134; Yanushevich, Y. G., et al. (2003) Russian J. Bioorganic Chem 29(4) 325-329; and Ray, K., et al. (2008) J. Phys. Chem. C 112(46): 17957-17963, all of which are incorporated herein by reference in their entireties for all purposes. Many such labeling groups are commercially available, e.g., from the Amersham Biosciences division of GE Healthcare, and Molecular Probes/Invitrogen Inc. (Carlsbad, Calif.), and are described in 'The Handbook—A Guide to Fluorescent Probes and Labeling Technologies, Tenth Edition' (2005) (available from Invitrogen, Inc./Molecular Probes and incorporated herein in its entirety for all purposes). Further, a combination of the labeling strategies described herein and known in the art for labeling reaction components can be used.

International Patent Application No. PCT/US2011/060338 (filed Nov. 11, 2011, and incorporated herein by reference in its entirety for all purposes) provides various additional strategies, methods, compositions, and systems for detecting modifications in a nucleic acid, e.g., during real-time nascent strand synthesis. For example, since DNA polymerases can typically bypass 5-MeC in a template nucleic acid and properly incorporate a guanine in the complementary strand opposite the 5-MeC, additional strategies are desired to detect such altered nucleotides in the template. Various such strategies are provided herein, such as, e.g., a) modification of the polymerase to introduce an specific interaction with the modified nucleotide; b) detecting variations in enzyme kinetics, e.g., pausing, retention time, etc.; c) use of a detectable and optionally modified nucleotide analog that specifically base-pairs with the modification and is potentially incorporated into the nascent strand; d) chemical treatment of the template prior to sequencing that specifically alters 5-MeC sites in the template; e) use of a protein that specifically binds to the modification in the template nucleic acid, e.g., delaying or blocking progression of a polymerase during replication; and f) use of sequence context (e.g., the higher frequency of 5-MeC nucleotides in CpG islands) to focus modification detection efforts on regions of the template that are more likely to contain such a modification (e.g., GC-rich regions for 5-MeC detection). These strategies may be used alone or in combination to detect 5-MeC sites in a template nucleic acid during nascent strand synthesis, and are contemplated for use with the methods and compositions provided herein.

Various different polymerases may be used in template-directed sequence reactions, e.g., those described at length, e.g., in U.S. Pat. No. 7,476,503, the disclosure of which is incorporated herein by reference in its entirety for all purposes. In brief, the polymerase enzymes suitable for the present invention can be any nucleic acid polymerases that are capable of catalyzing template-directed polymerization with reasonable synthesis fidelity. The polymerases can be DNA polymerases or RNA polymerases (including, e.g., reverse transcriptases), DNA-dependent or RNA-dependent polymerases, thermostable polymerases or thermally degradable polymerases, and wildtype or modified polymerases. In some embodiments, the polymerases exhibit enhanced efficiency as compared to the wildtype enzymes for incorporating unconventional or modified nucleotides, e.g., nucleotides linked with fluorophores. In certain preferred embodiments, the methods are carried out with polymerases exhibiting a high degree of processivity, i.e., the ability to synthesize long stretches (e.g., over about 10 kilobases) of nucleic acid by maintaining a stable nucleic acid/enzyme complex. In certain preferred embodiments, sequencing is performed with polymerases capable of rolling circle replication. A preferred rolling circle polymerase exhibits strand-displacement activity, and as such, a single circular template can be sequenced repeatedly to produce a sequence read comprising multiple copies of the complement of the template strand by displacing the nascent strand ahead of the translocating polymerase. Since the methods of the invention can increase processivity of the polymerase by removing lesions that block continued polymerization, they are particularly useful for applications in which a long nascent strand is desired, e.g. as in the case of rolling-circle replication. Non-limiting examples of rolling circle polymerases suitable for the present invention include but are not limited to T5 DNA polymerase, T4 DNA polymerase holoenzyme, phage M2 DNA polymerase, phage PRD1 DNA polymerase, Klenow fragment of DNA polymerase, and certain polymerases that are modified or unmodified and chosen or derived from the phages 129 (Phi29), PRD1, Cp-1, Cp-5, Cp-7, Φ15, Φ1, Φ21, Φ25, BS 32 L17, PZE, PZA, Nf, M2Y (or M2), PR4, PR5, PR722, B103, SF5, GA-1, and related members of the Podoviridae family. In certain preferred embodiments, the polymerase is a modified Phi29 DNA polymerase, e.g., as described in U.S. Patent Publication No. 20080108082, incorporated herein by reference in its entirety for all purposes. Additional polymerases are provided, e.g., in U.S. Ser. No. 11/645,125, filed Dec. 21, 2006; Ser. No. 11/645,135, filed Dec. 21, 2006; Ser. No. 12/384,112, filed Mar. 30, 2009; and 61/094,843, filed Sep. 5, 2008; as well as in U.S. Patent Publication No. 20070196846, the disclosures of which are incorporated herein by reference in their entireties for all purposes.

In certain aspects, methods and compositions provided herein utilize modified and/or non-natural (e.g., non-standard or non-cognate) nucleotide analogs and/or base pairing. For example, certain non-natural nucleotide analogs can be incorporated by a polymerase into a nascent strand opposite a modification, e.g., missing or damaged base. In certain embodiments, such non-natural nucleotide analogs are detectably labeled such that their incorporation can be distinguished from incorporation of a natural or cognate nucleotide or nucleotide analog, e.g., during template-directed nascent strand synthesis. This strategy allows real-time sequencing that generates reads that not only provide base sequence information for native bases in the template, but also modified bases without requiring further modifications to the standard methods (Eid, et al, supra). This method facilitates modification profiling in the absence of repeated sequencing of each DNA template, and is particularly well suited to de novo applications. In certain embodiments, the modified or non-natural nucleotide analogs are not incorporatable into the nascent strand and the polymerase can bypass the modification using a native nucleotide or nucleotide analog, which may or may not be labeled. Since the modified or non-natural analog has a higher affinity for the modification than a native analog, it will bind to the polymerase complex multiple times (repeatedly being "sampled" by the polymerase) before a native analog is incorporated, resulting in multiple signals for a single incorporation event, and thereby increasing the likelihood of accurate detection of the modification. Similar methods for sequencing unmodified template nucleic acids are described in greater detail in U.S. Ser. No. 61/186,661, filed Jun. 12, 2009; Ser. No. 12/370,472, filed Feb. 12, 2009; Ser. No. 13/032,478, filed Feb. 22, 2011; and Ser. No. 12/767,673, filed Apr. 26, 2010, all of which are incorporated herein by reference in their entireties for all purposes.

Examples of the use of modified, non-natural, non-standard and/or non-cognate nucleotide analogs and/or base pairing to detect modifications of a template nucleic acid are detailed in International Patent Application No. PCT/US2011/060338, filed Nov. 11, 2011, previously incorporated herein. For example, since 5-MeC retains Watson-Crick hydrogen bonding with guanine, a modified guanine nucleotide analog can be used to detect 5-MeC in the template strand, and some guanine nucleotide analogs appropriate for this application are further described elsewhere, e.g., in International Application Pub. No. WO/2006/005064 and U.S. Pat. No. 7,399,614. Similar modifications can be made to nucleotide analogs appropriate for SMRT® sequencing applications, e.g., those with terminal-phosphate labels, e.g., as described in U.S. Pat. Nos. 7,056,661 and 7,405,281; U.S. Patent Pub. Nos. 20070196846 and 20090246791; and U.S. Ser. No. 12/403,090, all of which are incorporated herein by reference in their entireties for all purposes. In certain embodiments, 5-MeC detection may be carried out using a modified guanine nucleotide analog described above that carries a detectable label that is distinguishable from detectable labels on other reaction components, e.g., other nucleotide analogs being incorporated. Such a strategy allows 5-MeC detection by observation of a signal, rather than or in addition to altered polymerase kinetics, which facilitates methylation profiling even in the absence of redundant or replicate sequencing of the template.

Certain embodiments use other non-natural base pairs that are orthogonal to the natural nucleobases pairs. For example, isoguanine (isoG) can be incorporated by a polymerase into DNA at sites complementary to isocytosine (isoC) or 5-methylisocytosine ($^{Me}$isoC), and vice versa, as shown by the following chemical structure and described in A. T. Krueger, et al., "Redesigning the Architecture of the Base Pair: Toward Biochemical and Biological Function of New Genetic Sets." *Chemistry & Biology* 2009, 16(3), 242, incorporated herein by reference in its entirety for all purposes. Other non-natural base pairs that are orthogonal to the natural nucleobases pairs can also be used, e.g., Im-N$^O$/Im-O$^N$, dP/dZ, or A*/T* (described further in Yang, et al. (2007) Nucleic Acids Res. 35(13):4238-4249; Yang, et al. (2006) Nucleic Acids Res. 34(21):6095-6101; Geyer, et al. (2003) Structure 11: 1485-1498; J. D. Ahle, et al., *Nucleic Acids Res* 2005, 33(10), 3176; A. T. Krueger, et al., supra; and A. T. Krueger, et al., Curr Opinions in Chem Biology 2007, 11(6), 588).

III. Chemical Modification of Template

Direct detection of modifications (e.g., methylated bases as described above) without pre-treatment of the DNA sample, has many benefits. Alternatively or additionally, complementary techniques may be employed, such as the use of non-natural or modified nucleotide analogs and/or base pairing described elsewhere herein. In general, such complementary techniques serve to enhance the detection of the modification, e.g., by amplifying a signal indicative of the modification. Further, while the methods described herein focus primarily on detection of 5-MeC nucleotides, it will be clear to those of ordinary skill in the art that these methods can also be extended to detection of other types of nucleotide modifications or damage. In addition, since certain sequencing technologies (e.g., SMRT® sequencing) do not require amplification of the template, e.g., by PCR, other chemical modifications of the 5-MeC or other modifications can be employed to facilitate detection of these modified nucleotides in the template, e.g., by employing modifying agents that introduce additional modifications into the template at or proximal to the modified nucleotides. For example, the difference in redox potential between normal cytosine and 5-MeC can be used to selectively oxidize 5-MeC and further distinguish it from the nonmethylated base. Such methods are further described elsewhere, and include halogen modification (S. Bareyt, et al., Angew Chem Int Ed Engl 2008, 47(1), 181) and selective osmium oxidation (A. Okamoto, Nucleosides Nucleotides Nucleic Acids 2007, 26(10-12), 1601; and K. Tanaka, et al., J Am Chem Soc 2007, 129(17), 5612), and these references are incorporated herein by reference in their entireties for all purposes.

By way of example, DNA glycosylases are a family of repair enzymes that excise altered (e.g., methylated), damaged, or mismatched nucleotide residues in DNA while leaving the sugar-phosphate backbone intact. Additional information on glycosylase mechanisms and structures is provided in the art, e.g., in A. K. McCullough, et al., Annual Rev of Biochem 1999, 68, 255. In particular, four DNA glycosylases (ROS1, DME, DML2, and DML3) have been indentified in Arabidopsis thaliana that remove methylated cytosine from double-stranded DNA, leaving an abasic site. (See, e.g., S. K. Ooi, et al., Cell 2008, 133, 1145, incorporated herein by reference in its entirety for all purposes.) In addition, methods for the use of glycosylases for detection of various types of DNA damage are described in U.S. Ser. No. 61/186,661, filed Jun. 12, 2009 and incorporated herein by reference in its entirety for all purposes. Furthermore, it has been shown that a 5'-triphosphate derivative of the pyrene nucleoside (dPTP) is efficiently and specifically inserted by certain DNA polymerases into abasic DNA sites through steric complementarity. (See, e.g., T. J. Matray, et al., Nature 1999, 399(6737), 704, incorporated herein by reference in its entirety for all purposes.)

In certain embodiments of single-molecule, five-color DNA methylation sequencing, DNA glycosylase activity can be combined with polymerase incorporation of a non-natural nucleotide analog (e.g., a pyrene analog (dPTP)) covalently linked to a "fifth label" that is detectably distinct from labels on the other nucleotide analogs in the reaction mixture. Further, error metrics can also be used to identify the modification, e.g., an increase in binding events for the pyrene analog may occur at the abasic site, as well as at downstream positions as the incorporated pyrene analog is "buried" in the nascent strand during subsequent incorporation events. In certain embodiments, a non-hydrolyzable pyrene analog carrying a detectable label is used at a concentration sufficient to potentially bind (and be detected) several times at the abasic site before a hydrolyzable (and, preferably, distinctly labeled) analog is incorporated. Alternatively, or in addition, the non-hydrolyzable analog can display an increased residence time and, therefore, lengthen the emitted signal indicative of the presence of the particular lesion of interest. Typically, a non-hydrolyzable fifth-base is eventually displaced by a hydrolysable analog and synthesis of the nascent strand continues.

In other embodiments of single-molecule, five-color DNA methylation sequencing, DNA glycosylase activity can be combined with addition of a non-natural base (e.g., an otherwise modified cytosine) to replace the methylated base. Briefly, after glycosylase-catalyzed excision of 5-MeC (with or without cleavage of the phosphodiester backbone), a class I or class II AP endonuclease is added to remove the abasic ribose derivative by cleavage at the phosphate groups 3' and 5' to the abasic site, thereby leaving 3'-OH and 5'-phosphate termini. A polymerase capable of extending from the free 3'-OH (e.g., Pol I or human pol β) and a non-natural base (e.g., isoC, isoG, or MeisoC) are added to incorporate the non-natural base into the abasic site. A DNA ligase (e.g., LigIII) is added to close the phosphodiester backbone by forming covalent phosphodiester bonds between the free 3'-OH and 5'-phosphates via ATP hydrolysis. Finally, a processive polymerase (e.g., Φ29 DNA polymerase) is used to synthesize a nascent nucleic acid strand complementary to the template strand, where the fifth nucleotide analog is the complement of the non-natural base that replaced 5-MeC in the template. For example, if the replacement base was isoC or MeisoC, then the fifth analog would be isoG. As such, the fifth analog would only incorporate into the nascent strand at positions complementary to 5-MeC sites in the template nucleic acid. In preferred embodiments, the fifth analog has a detectable label (e.g., fluorescent dye) that is distinct from labels on other reaction components, e.g., detectable labels on other nucleotide analogs in the reaction mixture. Further, in certain embodiments, a non-natural or altered nucleotide that can base pair with one of the four nucleotide analogs, e.g., A, G, C, or T, can be used to replace the excised base in the template. In such embodiments no fifth fluorophore is required, and the non-natural or altered nucleotide in the template is detected primarily by virtue of the polymerase behavior during template-directed synthesis, as described at length elsewhere herein. This is particularly beneficial where the presence of the excised base causes a smaller response by the polymerase than the presence of the base with which it is replaced. As such, by removing the initial modified base and replacing it with a different modified base at which a polymerase has a more distinct or extreme kinetic signature, the practitioner enhances detection of the modified locus in the template.

In certain embodiments, the template may be modified by treatment with bisulfite. Bisulfite sequencing is a common method for analyzing CpG methylation patterns in DNA. Bisulfite treatment deaminates unmethylated cytosine in a single-stranded nucleic acid to form uracil (P. W. Laird, Nat Rev Cancer 2003, 3(4), 253; and H. Hayatsu, Mutation Research 2008, 659, 77, incorporated herein by reference in their entireties for all purposes). In contrast, the modified 5-MeC base is resistant to treatment with bisulfite. As such, pretreatment of template DNA with bisulfite will convert cytosines to uracils, and subsequent sequencing reads will contain guanine incorporations opposite 5-MeC nucleotides in the template and adenine incorporations opposite the uracil (previously unmethylated cytosine) nucleotides. Treatment of the single-stranded molecule with bisulfite is followed by single-molecule sequencing that provides a sequence read for both strands of the original template nucleic acid. Comparison of the resulting sequence reads for each strand of the double-stranded nucleic acid will identify positions at which an unmethylated cytosine was converted to uracil in the original templates since the reads from the two templates will be non-complementary at that position (A-C mismatch). Likewise, reads from the two templates will be complementary at a cytosine position (G-C match) where the cytosine position was methylated in the original template. In certain preferred embodiments, a circular template is used, preferably having regions of internal complementarity that can hybridize to form a double-stranded region, e.g., as described in U.S. Ser. No. 12/383,855 and U.S. Ser. No. 12/413,258, both filed on Mar. 27, 2009, and both incorporated herein by reference in their entireties for all purposes. Further, since preferred sequencing methods also provide reaction data apart from sequence data, detection of a change in kinetics of the sequencing reaction (e.g., IPD or pulse width) is also used to determine whether or not a position was always a T or is a U that was originally an unmethylated cytosine.

In yet further embodiments, a template nucleic acid is exposed to a reagent that transforms a modified nucleotide to a different nucleotide structure. For example, a bacterial cytosine methyl transferase converts 5-MeC to thymine (M. J. Yebra, et al., Biochemistry 1995, 34(45), 14752, incorporated herein by reference in its entirety for all purposes). Alternatively, the reagent may convert a methyl-cytosine to 5-hydroxy-methylcytosine, e.g., the hydroxylase enzyme TET1 (M. Tahiliani, et al., Science 2009, 324(5929), 930, incorporated herein by reference in its entirety for all purposes). In further embodiments, the reagent may include a cytidine deaminase that converts methyl-cytosine to thymine (H. D. Morgan, et al., J Biological Chem 2004, 279, 52353, incorporated herein by reference in its entirety for all purposes). In yet further embodiments, a restriction enzyme that specifically alters a modification of interest can be used to create a lesion at the modification site. For example, DPNI cleaves at a recognition site comprising methyladenosine. Optionally, the cleaved template could be repaired during an analytical reaction by inclusion of a ligase enzyme in the reaction mixture. As noted elsewhere herein, nucleotides other than 5-MeC can also be modified and detected by the methods provided herein. For example, adenine can be converted to inosine through deamination, and this conversion affected by methylation of adenine, allowing differential treatment and detection of adenine and MeA. The kinetic signatures of the resulting altered nucleotide during sequencing can be used to determine the nucleotide sequence of the original template nucleic acid.

Another modified base that can be detected using the methods provided herein is 5-hydroxymethylcytosine (5-hmC). Conventional bisulfite sequencing does not effectively distinguish 5-hmC from 5-MeC because 5-hmC tends to remain unmodified like 5-MeC. However, in certain embodiments, bisulfite conversion in combination with real-time single-molecule sequencing can be used in methods for distinguishing 5-MeC from 5-hydroxymethylcytosine (5-hmC). As noted above, bisulfite conversion changes cytosine into uracil and does not change 5-MeC. Bisulfite conversion also changes hydroxymethyl-cytosine (5-hmC) to cytosine-5-methylenesulfonate (CMS), which contains a bulky $SO_3$ adduct in place of the OH adduct of 5-hmC. Like methyl-cytosine, CMS base-pairs with guanine. A template so treated is subsequently subjected to a single-molecule template-directed sequencing reaction. The uracils present in the template (due to bisulfite conversion) can be distinguished from thymines using polymerase behavior, e.g., interpulse duration, pulse width, frequency of cognate sampling, accuracy of pairing, etc. If a complementary strand is also subjected to sequencing, then the complementary nucleotide sequence information can also be used to identify bases, as described above. Further, the SO3 adduct added during the conversion of 5-hmC to CMS will enhance the response of the polymerase to the modified base (e.g., causing increased pausing) and thereby facilitate identification of CMS versus 5-MeC in the template. As such, in certain embodiments a nucleic acid sample is treated with bisulfite and sequenced. U is discriminated from T based on polymerase kinetics and standard bisulfite sequencing algorithms, with those bases detected as U known to have originally been C. Bases detected as C based on their base-pairing with G are known to be 5-MeC or CMS (originally 5-hmC). 5-MeC and CMS are discriminated based upon their relatively different kinetics, due at least in part to the SO3 adduct present in CMS and absent in 5-MeC.

In yet further embodiments, the template can be further subjected to electrophile modification of 5-hmC, e.g., by addition of a bulky group that facilitates its detection and discrimination from 5-MeC and unmodified cytosine. Preferred methods include those described in the art, e.g., in Merino, et al. (2005) J. Am. Chem. Soc. 127: 4223-4231, Petrov, A. I. (1980) Nuc. Ac. Res. 8(23):5913-5929; Petrov, et al. (1980) Nuc. Ac. Res. 8(18):4221-4234; and Kamzolova, S. G. (1987) Biokhimiia 52(9):1577-82, the disclosures of which are incorporated herein by reference in their entireties for all purposes.) Addition of a bulky group at the OH group of 5-hmC alters the kinetics of the DNA polymerase-mediated incorporation of a nucleoside into a nascent strand opposite the modified 5-hmC, and this alteration facilitates detection and mapping of the 5-hmC within a template nucleic acid. These and other electrophilic compounds known in the art can be used similarly to those described above to add bulky adducts to nucleic acids and, thereby, provide a characteristic kinetic signature during single molecule sequencing reactions that is indicative of the presence of a given base so modified.

Glucosyltransferases can also be used to modify a template nucleic acid prior to sequencing, e.g., to enhance kinetic or other reaction data to facilitate detection of modified bases. For example, DNA glucosyltransferases can be used to transfer a glucose group to 5-hmC to enhance detection of this modified base. Exemplary enzymes for transferring glucose groups to hmC include, but are not limited to, T2-hmC-α-glucosyltransferase, T4-hmC-α-glucosyltransferase, T6-hmC-α-glucosyltransferase, and T2-hmC-β-glucosyltransferase. Other enzymes can be used to create diglucosylated hmC, such as T6-glucosyl-hmC-β-glucosyltransferase, which creates diglucosylated hmC with a β linkage between the two glucose groups. These enzymes are generally specific for hmC and do not typically alter other bases such as A, C, MeC, T, or G. As such, treating hmC-containing nucleic acids with such enzymes creates nucleic acids in which the hmC residues have been converted to monoglucosylated-hmC or multi-glucosylated-hmC. Glucosylated-hmC is much larger and bulkier than hmC, and therefore has a distinctive effect on polymerase activity when present in a template nucleic acid. Details on the glucosylation of 5-hmC by glucosyltransferases are known in the art, e.g., in Josse, et al. (1962) J. Biol. Chem. 237:1968-1976; and Lariviere, et al. (2004) J. Biol. Chem. 279:34715-34720.

The strategy for addition of glucose moieties to hmC described above can be modified in various ways. For example, (a) the glucose adducts added could comprise a detectable label to provide another mode of detection, e.g., in addition to monitoring the kinetics of the reaction, (b) an affinity tag could be linked to a glucose adduct for subsequent purification, and/or (c) further steps can be performed to add modifications in addition to the glucose adduct, e.g., that are linked to the nucleic acid through the glucose adduct. In yet further embodiments, a glucosyltransferase enzyme can be used that binds to the template but does not dissociate, and therefore results in a further modification (e.g., bound agent) that can be detected during single-molecule sequencing, e.g., by detection of a significant pause of nascent strand synthesis.

In further embodiments, both hmC and 5-MeC and be modified prior to sequencing. For example, the nucleic acid can be subjected to glucosylation to convert hmC to glucose-hmC, and subsequently the 5-MeC bases can be converted to hmC, e.g., using TET1 protein. Detection of glucose-hmC will be indicative of an hmC in the original nucleic acid, and detection of hmC will be indicative of a 5-MeC in the original nucleic acid. Alternatively, the hmC generated by conversion of 5-MeC can be further modified to produce a greater enhancement of detection while maintaining a signal distinct from that of the glucose-hmC generated by conversion of hmC in the original nucleic acid. Alternatively or additionally, different sugar groups can be added to each, e.g., selected from glucose, maltose, sucrose, lactose, galactose, or multiples (e.g., di- or tri-glucosyl (or other sugar) groups) or combinations thereof.

Although the disclosures above focused on introducing additional modifications to nucleotides that already comprised a modification, modifications can also be introduced to nucleotides that are initially unmodified, e.g., where it is desirable to enhance the detection of a given base by adding a kinetic signature. A modification can be added that results in the kinetic signature during a sequencing reaction. For example, all unmodified cytosines in a template nucleic acid can be converted to 4-MeC prior to sequencing. Any 5-MeC will not be converted. During sequencing the kinetic signatures generated at each cytosine will indicate whether the cytosine is 4-MeC (originally unmodified C) or 5-MeC (5-MeC in the original nucleic acid). Alternatively, one can employ a methyltransferase under deamination conditions as described in Sharath et al. ((2000) Biochemistry 39(47): 14611-14616) to deaminate cytosine bases while leaving 5-MeC unaltered. The deaminated cytosine bases, now uracils, would be "read" as thymine, and would be distinguishable from native thymines due to the sequence of the complementary strand, which would have a G rather than an A base in the complementary position. It will be appreciated that these examples are nonlimiting, and that other base modifications can be introduced to unmodified bases in a template to alter or enhance a kinetic signature within a sequencing reaction.

Further, while certain aspects of the methods provided herein benefit from the absence of amplification, which in many instances results in loss of base modifications in the resulting replicons, there are methods of amplification that preserve such modifications, thereby allowing faithful replication of the modified bases present in the original nucleic acid to provide replicons having the same modified bases. For example, a nucleic acid of interest can be cloned into a vector and transfected into a host (e.g., bacterial or other cell line) that will replicate the vector, and therefore the nucleic acid therein, and maintain the modifications, e.g., through the use of modification enzymes either naturally expressed by the host, or that the host has been engineered to express. After replication, the vector can be extracted from the host and the nucleic acid of interest excised and subjected to sequencing. Alternatively, the replicons can be treated in vitro to maintain modifications. Hemimethylated nucleic acids are produced from semiconservative replication of a fully methylated duplex to produce two daughter duplexes, each having one methylated strand and one unmethylated strand. Certain methyltransferase enzymes bind to hemimethylated nucleic acids and methylate the strand lacking methylation, thereby restoring the methylation status of the original nucleic acid molecule. Essentially any method for amplifying or replicating a modified nucleic acid that maintains the modification in the daughter nucleic acids can be used with the methods herein.

IV. Analysis of Genomic Samples

Epigenetic modifications on a chromosome are known to influence expression of genes that also map to that chromosome. For example, methylation or other modifications is promotor regions or repeat regions have been shown to affect gene expression and/or subsequent post-transcriptional modification, e.g., splicing of the mRNA transcripts. Alternative splicing patterns can result in the production of aberrant polypeptide products, and can thereby be the disease mechanism in certain disorders, such as repeat expansion disorders. As such, it is of interest to be able to map the chromosomal locations of epigenetic modifications, including both CpG and non-CpG methylation, hydroxymethylation, and others described herein, with detection of these modifications serving as a prognostic or diagnostic for certain disorders, e.g., to inform as to the susceptibility or resistance of an individual to such disorder, the expected severity of the disorder, the expected age-of-onset of the disorder, and/or preferred theranostic strategies that could prevent or lessen the severity of the disorder.

The pattern of modifications across a plurality of homologous chromosomes can be determined and associated with phenotypic traits, much as a sequence variant is analyzed. For simple organisms having only a single chromosome, this can be done relatively simply, e.g., using a long-read sequencing technology that can provide both sequence and modification data for the chromosome, e.g. using the methods described in International Patent Application No. PCT/US2011/060338, filed Nov. 11, 2011. With a genome having only a single chromosome, all sequence reads are reasonably mapped on the same chromosome. The mapping problem can become more difficult for organisms that have multiple different types of chromosomes, but typically polynucleotide sequence differences between the different types of chromosomes are indicative of which chromosome produced a given sequence read, as long as the sequence read is long enough to have a unique locus in the genome. Further, there are methods for selecting and isolating a single chromosome prior to sequencing, which disambiguates the chromosomal source of the resulting reads, but such isolation is not usually perfect, so there can still be reads generated from contaminating nucleic acids. Further, the sample losses that accompany such a procedure may not be tolerable, e.g., where a genomic sample is in short supply. Further complicating genomic sequence mapping are polyploid organisms, which have a plurality of a same chromosome type, termed "homologous chromosomes," in a single cell. Since the polynucleotide sequences of two homologous chromosomes are very similar (typically nearly identical), it can be difficult to map sequence reads from fragments of the homologous chromosomes to one homolog or the other using polynucleotide sequence data alone, since a given read may actually be identical to regions of both homologs.

For example, humans have chromosomes numbered from 1 to 22 (autosomes), plus X and Y "sex chromosomes," and as diploid organisms they have two of each type of autosome (1-22) and either an XX or XY pair for a total of 46 individual chromosomes per somatic cell. During gametogenesis, the diploid genome is reduced so that each haploid gamete produced (egg or sperm) contains only one of each autosome and one sex chromosome. During fertilization, the paternal set of nuclear chromosomes in a sperm cell are released into an egg cell where they pair with the maternal set of nuclear chromosomes in the egg, thereby restoring the diploid number of nuclear chromosomes. This fertilized egg can then begin cell division leading to the development of an offspring that comprises pairs of "homologous" chromosomes in each cell, each pair comprising a maternally-derived chromosome and a paternally-derived chromosome of the same chromosome type. Chromosomes that are homologous to one another typically comprise the same genes, regulatory regions, and other major chromosomal characteristics in the same locations along their lengths, but these genes and other sequences are not necessarily identical between the two chromosomes and there are often small differences between their polynucleotide sequences (different alleles, SNPs, insertions, deletions, etc.), and the presence and the locations of modifications including but not limited to modified bases (e.g., methylation, hydroxymethylation, etc.), bound agents (transcription factors, histones, etc.), and secondary structures (hairpin structures, etc.). Epigenetic modifications are known to affect chromosome function, e.g., gene expression and regulation, and since these effects typically are specific to loci on the same chromosome as the epigenetic modifications, it is of interest to determine which polynucleotide sequences (e.g., which allele of a gene of interest) share a chromosome with these and other modifications. In doing so, a haplotype for each chromosome is determined that comprises both sequence and modification information, providing a rich data set that can distinguish between sequence reads from the maternally-derived and paternally-derived homologs. Detection of modified bases, bound agents, secondary structures, and other nucleic acid modifications is further detailed in International Patent Application No. PCT/US2011/060338, filed Nov. 11, 2011, incorporated herein by reference in its entirety for all purposes.

Since human chromosomes are very large and difficult to handle in one piece, they are typically fragmented before sequencing, which can separate an epigenetic modification from a genomic region whose function is regulated by the modification. As such, sequencing reads must be assembled together in order to reconstruct the sequence of the original chromosome, i.e., to ensure that the alleles in cis with one another are all mapped to the same homolog, and those in trans with one another are mapped to different homologs. Sequencing methods that produce long sequencing reads make this assembly easier, at least in part because the fragments being sequenced are larger, but it is still a significant challenge to distinguish between polynucleotide sequences from two homologous chromosomes having very similar sequences, even where allelic differences exist. In certain aspects, the invention provides a method of sequencing homologous chromosomes in the same sequencing reaction mixture, where individual template nucleic acid molecules are subjected to single-molecule, real-time sequence analysis that provides both base sequence data and kinetic data, e.g., based on the real-time kinetics of the sequencing reaction itself. The modification data informs as to which homologous chromosome a given polynucleotide sequence read (and the alleles therein) maps, allowing construction of the homologous chromosome sequence and identification of which alleles are in cis with the modifications present. In some embodiments, a modification is known to be on only one of a pair of homologous chromosomes, and the detection of the kinetic signature of the modification within a sequence read is used to assign the sequence read to the correct homolog. In other embodiments, the detection of kinetic signatures of a modification is used to facilitate assembly of sequence reads into a contig by providing elements other than base identity to use in construction a multiple sequence alignment. The use of kinetic data is applicable to both resequencing and de novo sequencing applications, and generally provides a richer data set for a wide variety of subsequent analyses.

In a preferred embodiment, a sample comprising genomic DNA is treated to fragment the genomic DNA, and the resulting genomic fragments, which include pairs of homologous chromosomes, are included in a single reaction mixture. The genomic fragments are subjected to a single-molecule, real-time sequencing reaction that produces both polynucleotide sequence data and modification data within a single sequencing read for a single fragment molecule. A sequencing read is generated for each fragment molecule sequenced, and the polynucleotide sequence data and modification data are analyzed to assign the sequence reads to a particular homologous chromosome. As such, the assembly of the sequence reads depends not only on the polynucleotide sequence data in each read, but also on the types and patterns of modifications detected within the same read. These modifications essentially act as additional base types that increase the complexity of the sequence reads generated as compared to sequence reads employing only four base types. The increased complexity simplifies mapping of those reads to the correct homolog since the more complex sequencing reads are unlikely to map to both homologs. In preferred embodiments, the genomic DNA fragments are not chemically modified prior to sequencing, e.g., by treatment with bisulfite, and the modified and unmodified nucleotides in the genomic fragments are detected in their native form. In this way, modification detection facilitates determination of the homologous chromosome source of a genomic DNA fragment and subsequent assembly of sequencing reads to construct the homologous chromosome sequences.

In an aspect of the invention, there is an algorithm loaded into a digital computer that contains DNA sequence data and the associated chemical modification information pertaining to the DNA. When there are exploitable differences in modification with position, these can be identified by the use of a clustering algorithm. The algorithm would be applied through a sequence of the following steps. First, a provisional assembly of the data would be conducted that would identify contigs with high confidence that they are correct. In one implementation, the assembly algorithm is configured to include as much as possible of any repeat that may be present at the ends. In a clonal organism, these contigs will nearly all terminate in such repeats whose length is longer than the read length of the sequencing system. A table of repeat sequences is constructed by performing an overlap analysis of the sequences at the ends of the contigs. Selected for the table is any sequence that occurs in more than one contig end and is identical for at least n bases, where n could be half the average read length, the average read length, twice the average read length or three times the average read length. All of the reads that have any portion mapping to any entry of the table are then mapped using an alignment algorithm, e.g., BLASR (http://www[dot]pacbiodevnet[dot]com/SMRT-Analysis/Algorithms/BLASR) or the Burrows-Wheeler Aligner (BWA; bio-bwa[dot]sourceforge[dot]net/), allowing every read to map to any location that passes a significance threshold without regard for better or worse mapping to other locations. For each of the table entries, the reads are then clustered according to the kinetic information, using each of the interpulse duration (IPD) values (and if desired also the pulse duration values) as a dimension in a high-dimensional vector. For the sake of definiteness, in some embodiments a window of length W is chosen for each valid starting position within the table entries reads that span the entire window are selected and each IPD and/or pulse width value within the window is used as a dimension in the W-dimensional (or 2*W in the case of IPD and pulse width) space. These vectors are then subjected to a cluster analysis by any of a number of methods know in the art (examples include K-means clustering, expectation maximization, DBSCAN, OPTICS, and others) to determine if there are resolvable clusters within the population of reads. For a contig fragment of length N this is repeated N−W times. The clusters are in the ith window are associated with the clusters in the i+1th window by looking for common membership of reads. For example, if there are two clusters A and B in the ith window and there are two clusters C and D in the i+1th cluster, then if 95% of the members of A are found in C and 95% of the members of B are found in D then A and C are identified as coming from the same genomic location and similarly B and D. This is conducted across all of the valid windows within each contig. Next, a subset of the windows is chosen (that for example, could collectively cover all of every base of every table entry). This subset is similarly associated with each other by joint membership above a threshold value (which can be static or dynamically assigned). The resulting table of associations represents a graph which will then resolve assembly ambiguities in a otherwise unresolvable graph. This is done by identifying windows that contain at least a certain amount of unique sequence, and associating those windows with the contigs from the assembly, then a string of window associations can be followed from one to the next to lead to another contig. In cases where sufficient kinetic differences exist between different versions of sequence repeats, these strings of association will have no branches and thus there will be no remaining ambiguities.

In some embodiments, the types or patterns of modifications present on one chromosome are known to be absent from its homolog. For example, in mammalian females the process of dosage compensation causes inactivation of one X chromosome (to produce a "Barr body") while the other X chromosome remains active. X-inactivation is a process by which one X chromosome is (mostly) inactivated by packaging it into transcriptionally inactive heterochromatin, which includes hypermethylation of the DNA as well as other structural modifications. Additional information on X-inactivation is well known in the art, e.g., see the New South Wales government's Health Centre for Genetics Education website at www[dot]genetics[dot]edu[dot]au/Information/Genetics-Fact-Sheets. Although X-inactivation has been studied for over half a century, many questions remain. The mechanisms by which a cell counts and silences X chromosomes, and maintains the silenced state is not fully understood, nor is the role of noncoding RNAs, and the fact that not all genes are silenced within an "inactive" X chromosome. Therefore, the methods provided herein can be sued to analyze sequence reads displaying hypermethylation characteristic of X-inactivation and assign them to the X chromosome homolog packaged into the Barr body while those sequence reads not exhibiting such hypermethylation are mapped to the active X chromosome homolog. Since inactivation in marsupials applies exclusively to the paternally derived X chromosome, sequence reads that show X-inactivation-related hypermethylation are assigned to the paternal homologous X chromosome, while those that do not are assigned to the maternal homologous X chromosome. Since X-inactivation is random in other mammals, such as humans, detection of hypermethylation alone cannot assign a given sequence read to either the maternal or paternal chromosome. However, once an X chromosome is inactivated it will remain inactive throughout the lifetime of the cell and this inactivation is maintained in its daughter cells, so within a population of daughter cells produced from a progenitor cell after X-inactivation, detection of X-inactivation-specific hypermethylation can distinguish between the two homologous chromosomes. In addition, the study of X-inactivation may also provide insight into cancer biology, since many human breast and ovarian tumors have two active X chromosomes (Liao, et al. (2003) Cancer Investigation 21, 641-658). Yet further, at least one study has found extensive variability in the expression of X-linked genes in females (Carrel, et al. (2005) Nature 434: 400-404), and the methods herein provide a simplified strategy for the study of X-inactivation in humans and other organisms that utilize this form of dosage compensation. X-inactivation represents a great model system with which to study a broad range of developmental and epigenetic processes, in particular those involving stable gene expression regulation without changes to the underlying DNA sequence. The methods herein provide strategies for studying these epigenetic mechanisms over long stretches of genomic DNA by allowing simultaneous sequencing and modification detection that can not only provide haplotype information for a single homolog, but can also distinguish between maternally-derived and paternally-derived sequences.

Genomic imprinting is a genetic phenomenon that causes parent-of-origin-specific gene expression. An imprinted allele of a gene is silenced while the non-imprinted allele of the gene is expressed. In some cases, the non-imprinted allele is inherited from the mother and the imprinted allele is inherited from the father (e.g., H19 or CDKN1C), and in other cases the non-imprinted allele is inherited from the father and the imprinted allele is inherited from the mother (e.g., IGF-2). This monoallelic gene expression is accomplished through the use of epigenetic modifications including methylation and histone modifications. Often these modifications are established in the germline and maintained throughout all somatic cells of an organism, but some imprinted genes display monoallelic gene expression in a tissue-specific manner. In insects, imprinting has been shown to silence the paternal alleles in males, which is involved in sex determination. Many imprinted genes are found in clusters, termed "imprinted domains," suggesting a level of coordinated control. Common regulatory elements in or near imprinted domains include non-coding RNAs and differentially methylated regions. When these regulatory elements control imprinting, they are termed "imprinting control regions." Although hypermethylation is often associated with gene silencing, the effect of methylation depends upon the default state of the region.

Transcriptional profiles have typically been used to identify imprinted genes, and these require analysis of mRNA transcripts. There are at least 80 imprinted genes in humans and mice, and there may be many more. The methods herein provide a direct method of identifying and analyzing imprinted genes that does not require purification, sequencing, and/or other analysis of mRNA transcripts. Rather, DNA is analyzed directly to identify imprinted genes by virtue of simultaneous detection of both base sequence data and modification data in sequence reads for single DNA fragments. For imprinting that is maintained in all somatic tissues of an organism, this approach can use somatic tissue from anywhere in the body to detect epigenetic markers consistent with imprinting, and does not depend on the level of expression of the non-imprinted allele as does a transcriptional profiling approach. As such, the ability to generate sequence information having both base sequence information and modification information provides the opportunity to analyze genes to not only detect epigenetic signatures of imprinting, but also to determine whether the maternal chromosome, paternal chromosome, or both chromosomes is imprinted. Further, where chromatin is sequenced without removing the histones, the kinetics of sequencing is affected by the presence and modification status (e.g., methylation, acetylation, and/or phosphorylation) of histones, so even that aspect of imprinting can be interrogated using the methods described herein and in International Patent Application No. PCT/US2011/060338, filed Nov. 11, 2011. For more information on histone modifications, see, e.g., Fuks, F. (2005) Curr. Op. Genet. & Dev. 15:1-6; and Zhang, et al. (2001) Genes & Dev. 15:2343-2360, both of which are incorporated herein be reference in their entireties for all purposes. The analysis and diagnosis of diseases and disorders due to imprinting and/or other parent-of-origin-dependent expression patterns is contemplated and having been linked to a multitude of phenotypes, e.g., Beckwith-Wiedemann syndrome, Alzheimer disease, mitochondrial disorders/syndromes, metabolic disorders, autism, bipolar disorder, diabetes, male sexual orientation, aging, obesity, and schizophrenia; as well as a number of cancers: bladder, breast, cervical, colorectal, esophageal, hepatocellular, lung, mesothelioma, ovarian, prostate, testicular, and leukemia, among others (Falls et al, Genomic Imprinting: Implications for human disease. Am J Pathol 154: 635-47, 1999; Jirtle, Genomic imprinting and cancer. Exp Cell Res 248: 18-24, 1999; Simmons, et al. (2008) Nature Education 1(1); Takasugi, et al. (2010) BMC Genomics 11:481; and Barres, et al. (2011) Am J Clin Nutr 93(4):8975-9005, the disclosures of which are incorporated herein by reference in their entireties for all purposes). Additional information on imprinting is provided in Sleutels, et al. (2002) Advances in Genetics 46, 11-163.

Pseudogenes are gene-like sequences in a genome that are not expressed, e.g., are not transcribed or their transcripts are not translated. They are characterized by their similarity to known genes, and are often labeled as "junk DNA." They also frequently display methylation patterns that differ from their active gene counterpart, as shown, e.g., in Cortese, et al. (Genomics 91(6):492-502 (2008)), incorporated herein by reference in its entirety for all purposes. As such, the generation of both modification data and polynucleotide sequence data in a single sequencing read provides a means to distinguish a pseudogene sequence from an active gene sequence even where the polynucleotide sequence data is similar. For example, in many cases pseudogenes are more heavily methylated than an active gene sequence, so two sequencing reads having the same polynucleotide sequence can be mapped to the pseudogene or active gene depending on the level of methylation present in the read.

Similarly, certain organisms, and in particular plants, can have duplicated or "multi-copy" genes that have been shown to have variable methylation patterns. As such, mapping of sequencing reads from these multi-copy genes to a particular copy can be facilitated by consideration of modifications present in the sequencing reads where those modifications distinguish between different copies of the gene in the genome. Also, patterns of modifications across multi-copy genes, or even an overall amount of one or more modifications across the multiple copies can be considered a genomic trait that may be associated with a phenotype of interest. Likewise, the mapping of modifications within these multi-copy genes can allow counting of the number of copies to further characterize the structure of a genomic region.

Yet further, the ability to provide the long haplotypes comprising sequence and modification data afforded by a single-molecule sequencing technology that collects kinetic information in real time provides tremendous benefits to understanding the epigenetic interactions within the genome. For example, as noted above the ability to determine whether a first genomic region (having a first determined sequence/modification status) is in cis with a second genomic region region (having a second determined sequence/modification status) allows the genomic regions to be "phased," which allows further analysis of whether there regions are interacting in synergistic or antagonistic ways. The phasing information provided by the long sequencing reads combined with modification detection greatly facilitates such analyses, allowing not only phasing of sequence-based variants, but also of base modifications within the genome, both with other base modifications and with sequence-based variants.

V. Modification Status as a QTL

Similar to quantitative trait loci (QTL) based upon polynucleotide sequence information, QTL based upon modification data can be associated with physical phenotypes including but not limited to health status, drug response, and gene expression. The methods provided herein facilitate determination of overall modification status across a chromosome or, preferably, an entire genome. For example, where a set of loci are known to be differentially modified, depending on a given phenotype of interest, screening those loci for their modification status provides a subset of modified loci, the combination of which provides a further aspect to the genotypic contribution to the phenotype. In some instances, the manifestation of the phenotype is dependent upon an absolute amount of modification present, e.g., above a certain threshold. In other instances the specific combination of loci comprising the modification(s) is a key factor. Given the differential modification observed in different cells or tissues, the analysis may further comprise a comparison of modification status between different cells, tissues, developmental stages, etc. Yet further, a systems genetics approach can be applied that combines phenotypic measurements, genotype data, modification data, and, optionally expression data, to identify QTL associated with physical phenotypes. These QTL can then be used to identify loci that are associated with networks of genes that are functionally interrelated either because they produce proteins that are part of a common structure or because they are steps in a gene pathway. Further details and an example of this method is provided in Fang, et al. (2012) Nature Biotechnology 30(12):1232-1239, which is incorporated herein by reference in its entirety for all purposes.

In certain preferred embodiments, the ability to detect base modifications at single molecule resolution allows the quantitation of the number of molecules in a given sample that are modified at a particular locus. For a given locus, this type of mixture can be estimated for a population to generate a vector of quantitative measures over every individual in the population. This quantitative trait can then be correlated with variations in DNA (small nucleotide changes or structural variation) as a way to map genetic loci that may influence the degree to which a given site is modified (e.g., a mutation in a methylase could make it more or less effective at targeting a given site). In combination with other molecular phenotypes like gene expression or metabolite levels, the causal relationships between base modifications and their effect on traits like gene expression or higher order traits like disease can be explored and resolved.

VI. Complex Sample Analysis

Similar to homologous chromosome mapping, sequencing mixtures of related microorganisms can be difficult, but there is a growing interest in studying microbial metagenomics of populations of microorgansims that are living together in a specific environment. In order to identify the constituents of a given sample, researchers can do whole genome shotgun sequencing of all DNA isolated from the sample. Due to the possibility of large diversity of different organisms, second-generation sequencing methods are typically employed because of the large number of reads that are generated. However, because the reads are short, and gene sequences can often be conserved, it is often very difficult to determine if two separate reads come from the same or different organisms. For example, polynucleotide sequencing reads from samples comprising mixtures of strains or viral subtypes having similar sequences can be difficult to assign to a particular strain or subtype in the mixture. The goal is typically to assemble reads into large contigs and/or complete genomes, but use of short-read technologies makes this difficult or impossible.

Differences in epigenetic modifications between different bacterial, viral, or fungal strains/subtypes can aid in mapping a given sequence read to a particular organism. For example, bacteria typically make use of DNA adenine methylation, and this modification is important in bacteria virulence in organisms such as *E. coli, Salmonella, Vibrio, Yersinia, Haemophilus*, and *Brucella*. In *Alphaproteobacteria*, methylation of adenine regulates the cell cycle and couples gene transcription to DNA replication. In *Gammaproteobacteria*, adenine methylation provides signals for DNA replication, chromosome segregation, mismatch repair, packaging of bacteriophage, transposase activity, and regulation of gene expression. In the fungus *Neurospora crassa*, cytosine methylation is associated with relics of a genome defense system and silences gene expression by inhibiting transcription. Many other characteristic epigenetic modification patterns in microorganisms have been described in the literature and are known to the ordinary practitioner. The patterns of epigenetic modifications for these different purposes are distinct and characteristic of a particular organism, providing a method to distinguish one organism from another in a manner that complements polynucleotide sequence data. In this way, epigenetic modification detection during nucleic acid sequencing to produce polynucleotide sequence reads comprising both polynucleotide sequence and modification data facilitates mapping polynucleotide sequences to their source microorganism genomes. In particular, the sequence and methylation information is useful for scaffolding DNA from multiple organisms to help identify DNA fragments that come from a single organism, since DNA from a single organism will have the same methylation patterns (common methylated sequence motifs). This capability is a tremendous advantage when analyzing metagenomic samples comprising multiple different types of organisms.

In preferred embodiments, native DNA is extracted from a metagenomic (e.g., mixed) sample that contains an unknown number of different types of microorganisms. Isolated DNA is converted into sequencing libraries (e.g., shotgun sequencing libraries) and sequenced using a single-molecule, real-time sequencing technology that is capable of distinguishing modified (e.g., methylated) nucleotides from non-modified nucleotides within a template nucleic acid. In certain embodiments SMRT® sequencing is used, but other technologies can also be used, e.g., nanopore sequencing (e.g., from Oxford Nanopore Technologies, Oxford, UK). Further, although long-read technologies that provide single reads of at least 1000 kb or more are preferred, short-read sequencing technologies can also be used, e.g., alone or in combination with long-read technologies, and these include technologies from, e.g., Illumina, Life Technologies (Ion Torrent® or SOLiD® systems), and Roche (454® systems). Further, circular consensus sequencing (CCS) can also be used to repeatedly sequence a given template molecule to provide a consensus sequence for that template based only on reads from a single molecule. Although the read may be long, the template sequence itself is typically much shorter and there are multiple copies of the template sequence (and/or its complement) within the read. As such, the reads can be treated as short reads even though the actual full-length read is much longer. For very complex samples with high diversity (or to identify low copy number constituents of the population) where sequencing coverage of a given position is likely to be low, CCS may enhance identification of methylation and modified motifs.

The resulting sequencing data is analyzed for the presence of modifications including determination of sequence motifs that are modified. The reads can be grouped based on similarity of the motifs that are modified. Reads that have different methylation/modification patterns are likely to be from different organisms, or at least from different chromosomes (e.g., in the case of diploid or other multiploid organisms), and reads that have the same methylation/modification patterns are identified as possibly originating from the same organism. Where short- and long-read sequencing data is used in combination, the long reads are especially useful for determining where the short-reads map, which helps with the assembly of the metagenomic sample into larger contigs and with whole genome assembly.

Sequencing is preferably carried out on native (non-amplified) DNA to ensure that the modifications are actually present during the sequencing reaction. Some sequencing methods (e.g., ensemble methods) rely on an amplification of the template prior to sequencing, but these methods effectively remove the modification prior to the sequencing reaction. In some embodiments, a combination of amplified and non-amplified template is used. For example, the modifications can be detected during sequencing of non-amplified template, and a small portion of the original template can be amplified and sequenced to provide additional coverage for only the base sequence information. This is particularly useful in situations where the starting material is limiting for library preparation; the bulk of the native DNA is sequenced for modification detection, and amplified material is used to generate high sequence coverage (without modification information).

The method is applicable for analysis of essentially any modification that is detectable, and is particularly useful for modifications that frequently occur in microorganisms, including, but not limited to, 6-mA, 4-mC, 5-mC, phosphorothioate, glucosylated hmC, etc. Further, enrichment-based sample prep can be performed to specifically isolate an organism or class of organism of interest, e.g., bacterial cells, viral particles, phage particles, or other specific subpopulations.

This method is also applicable to other types of mixed samples. For example, in further embodiments, sequencing reads that include both polynucleotide sequence read data and modification data can be analyzed to distinguish between DNA from human and DNA from microorganism, e.g., in a sample collected from a human patient. For example, blood can be drawn from a patient showing symptoms of sepsis or other blood-borne infection and the nucleic acids in the blood can be sequenced to provide a set of sequence reads. The origin of the sequence reads, whether human or another organism in the blood, can be determined based on the epigenomic modifications present in each sequence read, e.g., in combination with the polynucleotide sequence data itself. Once assigned to the appropriate organism, the sequences can be analyzed to both identify the microorganism and, optionally, to screen the patient's DNA for genetic markers that indicate efficacy and/or likelihood of adverse events for various drugs that can be used to treat the infection. This will allow the organism to be typed and a best treatment to be identified quickly, based on sequencing reads from a single sequencing reaction mixture, thereby reducing the time between admission of the patient and initiation of a treatment regimen. Similar methods can be used to identify other microorganisms infecting a human patient, e.g., in cultures taken from the throat, ears, nose, stomach, bladder, feet, skin lesion, etc.

Prenatal screening can also benefit from the methods described herein. Cell sorting technologies are commonly used to isolate embryonic cells in maternal blood samples, and the isolated embryonic cells can then be subjected to various screening assays to determine the presence of various genetic abnormalities. The present invention obviates the need for cell sorting and instead sequences both maternal and embryonic nucleic acids together in a single sequencing reaction mixture to generate polynucleotide sequencing reads comprising both polynucleotide sequence data and modification data. Since non-CpG methylation is prevalent in embryonic stem cells but not in differentiated cells, the detection of this epigenetic modification within a sequencing read is indicative that the sequencing read corresponds to embryonic genetic material, thereby facilitating distinction between maternal and embryonic DNA. Similarly, stem cells in blood samples also have different methylation patterns than differentiated cells, so sequencing of blood samples that includes modification detection can be used to identify stem cell-derived nucleic acids from other nucleic acids in the blood of an individual.

In specific embodiments, the methods herein provide a method of diagnosing an individual (e.g., an unborn fetus) at risk of having an imprinting-dependent disease or other condition. For example, Prader-Willi syndrome (PWS) is caused by the deletion of the paternal copies of the imprinted SNRPN and NDN genes along with clusters of snoRNAs including SNORD64, SNORD107, SNORD108, SNORD109, and SNORD116 (HBII-85), which are on chromosome 15 in the region 15q11-13. Due to imprinting, the maternally inherited copies of these genes are silenced and only the paternal copies are expressed, so an individual with a paternal chromosome with this region deleted will exhibit PWS. Similarly, Angelman syndrome (AS) is caused by lack of expression of another gene in this region, UBE3A. This gene is found in the region 15q12 and while both the maternal and paternal copies are active in many of the body's tissues, UBE3A is normally expressed only from the maternal chromosome in certain areas of the brain due to imprinting of the copy in the paternal chromosome. If the maternal copy of the UBE3A gene is lost because of a chromosomal change or a gene mutation, a person will have no active copies of the gene in some parts of the brain. PWS and AS are the first reported instances of imprinting disorders in humans. Both PWS and AS can be caused by several different kinds of genetic phenomena, including deletion, uniparental disomy, or mutations that cause inactivation of the relevant gene(s). As described above, the sequencing methods herein can simultaneously produce sequence reads for a plurality of different nucleic acid molecules in a single sample. As such, a maternal blood sample can be used to sequence nucleic acids from both maternal and fetal cells in the mother's blood. The maternal sequence can be used to identify which sequences in the fetal nucleic acids are maternal in origin, and analysis of the 15q11-13 region for both homologs of the fetus will provide a diagnosis of whether the fetus is affected with either PWS or AS. For example, if the fetal nucleic acids have a deletion of the maternal copy of UBE3A, a diagnosis of AS is made; and if the fetal nucleic acids have a deletion of the paternal copies of the 15q11-13 region, a diagnosis of PWS is made. While there are various known methods for diagnosing these disorders, there is no single method that can both diagnose and distinguish between the various subtypes. The present invention provides such a method. This information can be useful for both treating the affected individual, as well as discerning a risk that a sibling will also be affected. Similarly, the prenatal diagnosis of other diseases, disorders, or other phenotypes due to imprinting and/or other parent-of-origin-dependent expression patterns is also contemplated.

In related embodiments, the methods herein provide a simplified method for detecting and sequencing cancer cells in a tissue sample from an individual. Aberrant DNA methylation patterns have been associated with a large number of human malignancies and found in two distinct forms: hypermethylation and hypomethylation compared to normal tissue. For example, hypermethylation typically occurs at CpG islands in promoter regions, is associated with gene inactivation, and is one of the major epigenetic modifications that repress transcription of tumor suppressor genes. Hypomethylation is associated with chromosomal instability. Further, previous studies have shown that tumors form distinct subtypes based on the degree of CpG-island methylation. (See, e.g., Toyota et al. (1999) Proc. Natl. Acad. Sci. USA 96:8681-8686, and Weisenberger et al. (2006) Nature Genetics 38(7):787-793, incorporated herein by reference it their entireties for all purposes.) Identification of such aberrant methylation patterns in a sequencing read from a biological sample is indicative that the source of the sequencing read is a cancerous cell. Yet further, the patterns of methylation can be used to identify a source of the cancer cell in the body of an individual due to the known methylation patterns that characterize different tissues of the body and act to maintain the differentiation of different cell types in those tissues. For example, if a blood sample is sequenced to reveal polynucleotide sequence reads having aberrant methylation patterns corresponding to cancer, DNA regions outside of the aberrant methylation patterns can be analyzed to determine where in the body the cancer cell originated based upon the differentiation-based methylation patterns found in normal differentiated cells from different tissues in the body. As such, the modifications within a polynucleotide sequence read can not only identify the read as having come from a cancer cell, but can also identify where in the body the cell originated because of the maintenance of tissue-specific epigenetic modifications. It is expected that this will allow much faster identification of a primary tumor in the body, which can lead to quicker initiation of treatment and most likely a better outcome, e.g., higher cure/survival rate.

Due to the rarity of certain cell types in some bodily fluids or tissues, in certain embodiments enrichment procedures are used prior to sequencing to increase the number of cells of interest in a given sample, some of which have been discussed supra and many of which are well known and routinely used in the art. For example, antibodies to surface proteins specific to a certain type of cell, e.g., cancer cell, can be used to enrich a mixture of the cells of interest. This enrichment need not be complete, since the polynucleotide sequence reads of the cells of interest can be distinguished from "contaminating" cells as described herein. Even where highly efficient cell sorting technology is used, the methods herein provide a further assurance that the polynucleotide sequence data being attributed to a cell of interest actually corresponds to that cell by validating the identity of the source cell through analysis of epigenetic modifications within the polynucleotide sequence reads.

In yet further aspects, methods herein facilitate determination of modifications within a forensic sample, thereby providing a further characteristic that can be used to identify the source, authenticate a sample, separate nucleic acids in a sample that potentially has multiple sources, etc. For example, detection of methylated bases in a forensic sample can confirm that the sample is biological in origin, e.g., that it has not been amplified. A sample that has been amplified did not come directly from biological material, and may be proof of contamination and/or evidence tampering. In certain embodiments, modifications caused by damage to nucleic acids, e.g., from exposure to UV, oxygen, etc., is identified and used in the analysis. For example, a dried blood sample is expected to contain damaged bases consistent with environmental exposure, so DNA-damage-related modifications within sequencing reads from the sample can provide further confirmation that the sequence reads came from the dried blood sample and not some other contaminating source. Further, the amount of damage can be indicative of how long the sample was exposed. In the field of forensic science it is desirable to be able to distinguish whether a DNA sample taken from a scene in the field derives from biological tissue or was synthetic DNA placed at the scene to confuse analysis or attempt to produce an incorrect result. The present methods can be applied to simultaneously extract sequence information as well as establish whether the DNA contains methylation patterns consistent with the supposed biological source.

VII. Expression Analysis Based on Modification Status

Cellular differentiation in eukaryotes involves epigenetic changes that alter gene expression in cells different tissue types. During morphogenesis, totipotent stem cells become the various pluripotent cell lines of the embryo, which in turn become fully differentiated cells, e.g., neuronal cells, muscle cells, epithelium, endothelium, etc. This occurs through activation of some genes and inhibition of other genes, as well as certain structural changes in the DNA, to produce all the different cell types of an organism. The most common epigenetic change is addition of methyl groups to DNA, mostly at CpG sites, to convert cytosine to 5-methylcytosine. Approximately 60-90% of CpGs are methylated in the human genome. Some areas of the genome are more heavily methylated than others, and highly methylated areas tend to be less transcriptionally active. Further, the particular areas that are heavily methylated in one tissue or cell type are different from the genomic regions that are heavily methylated on other tissue or cell types, and these differing patterns of methylation are directly related to differing patterns of expression of genes. As such, detection of methylation levels in various regions of the genome, e.g., within promotor, exonic, or intronic regions, is indicative of the activity of genes within those regions. By performing sequencing reactions that include modification data such as methylation status, secondary structure, and the presence of bound proteins or other factors, the present invention provides a method for determining expression levels that is not dependent upon isolation and sequencing of mRNA transcripts.

For example, histone modifications are known to be associated with gene expression, so determining the location of histones and how tightly they are bound to the DNA is indicative of expression of a gene in the vicinity. For example, histones are modified by methylation and/or acetylation. While methylation can either strengthen or weaken binding of histones, depending on the location of the modification, acetylation has generally been found to change the binding of histones such that transcriptional activity is increased. Likewise, deacetylation has been found to decrease transcription. Since the affinity of the histone has a direct effect on the availability of the gene for transcription, mapping histones and the strength of their binding within a DNA region is informative as to the transcriptional activity of the region. Binding of histones to DNA can be detected through the same kinetics-based detection methods as are used for other types of modifications. The sequencing process slows when a histone is encountered and resumes only when the histone has been displaced, so a histone that is bound more strongly is expected to take longer to displace. As such, the pause is characteristic of the modification status of the histones encountered, which is in turn characteristic of the transcriptional activity of the region.

The pattern and strength of histone association with a DNA region is indicative of the transcriptional activity of that DNA region. In preferred embodiments, modifying agents are used to mark the DNA and allow footprinting of the histone proteins (as well as other bound agents). In certain preferred embodiments, the DNA is marked or tagged with a modifying agent in a manner that is specific for regions in which histones are absent, e.g., since the regions wrapped around histones are unavailable for marking. For example, the genomic DNA can be subjected to modification with a methyltransferase, glucosyltransferase, or an enzyme that introduces phosphorothioate modifications. Preferably, the modifying agents introduce modifications that are absent from the native DNA so that the introduced modifications are distinguishable from any native modifications already present in the DNA sample. For example, a modification that is present in bacteria but absent from human DNA can be used to footprint histone proteins in a human DNA sample. Subsequently, the DNA is treated to remove only those histones that have a lower affinity for the DNA prior to sequencing, thereby only removing histones in regions that are transcriptionally active. The added modifications are detectable during sequencing, and three types of regions are identified in the resulting sequence reads. First, the regions that comprise the added modifications are regions that were not bound by any histones. Second, the regions that lack the added modifications are identified as regions previously associated with histones in transcriptionally active areas. Third, the regions that displayed kinetics consistent with a bound histone are identified as regions in transcriptionally inactive areas. These methods can be used in the absence of, or alternatively in combination with mRNA sequencing to analyze gene expression levels in different cells and tissues.

In certain aspects, sequencing methods that provide kinetic data indicative of modifications within a nucleic acid template are used to screen cell lines. For example, the status of a pluripotent cell line preparation can be assayed to determine what portion, if any, of its constituent cells are pluripotent cells. Using standard methods in the art, pluripotent cell lines can be created by contacting differentiated cell lines with one or more reprogramming agents that contribute to reprogramming of the differentiated cells to a pluripotent state. The cell line is grown in the presence of the reprogramming agent(s) for a period of time sufficient to begin reprogramming of said cell line. The progress of the cell line toward the pluripotent state can be monitored by taking periodic samples, extracting the nucleic acids, and sequencing them using a method that provides kinetic data indicative of the modification status of the nucleic acids. Modifications characteristic of pluripotent cells (e.g., non-CpG methylation) are identified and used to determine the prevalence of pluripotent cells in the cell culture. For example, a prevalence of non-CpG methylation in the cell line is indicative that the differentiated cell line has been reprogrammed into a pluripotent cell line.

VIII. Other Related Applications

Second generation sequencing technologies (e.g., SOLid® and Solexa® sequencing) have read lengths that are too short to effectively sequence long, highly repetitive genomic regions. Such regions include the critically important centromeric and telomeric regions, which are often characterized as heterochromatic regions, tightly packaged areas in the genome that tend to be less transcriptionally active than the less tightly packaged euchromatic regions. Other highly repetitive regions include those containing microsatellites or other regions having variable copy numbers of short-repeat sequences. Heterochromatic regions also tend to be highly modified, and second generation sequencing technologies that do not provide kinetic reaction data are not generally able to identify such modifications based upon a single sequencing read. In contrast, sequencing technologies that provide long read lengths (e.g., at least about 500, 1000, 1500, 2000, 3000, 5000, or 10,000 bases or more) are able to extend deeply into these regions, preferably spanning them completely to provide not only sequence and kinetic data, but also copy number. Further, where single-molecule kinetic reaction data is also provided, the modifications within these regions can also be fully characterized within a single sequencing read, e.g., without the need to treat the genomic DNA with harsh, DNA-damaging chemicals such as bisulfite. This ability to sequence through a highly repetitive region and, simultaneously, detect modifications therein is of particular importance in the study of diseases and disorders caused by changes in repeat regions within a genome. There are many repetitive regions within the human genome that are associated with such diseases/disorders, which include e.g. myotonic dystrophy, Huntington's disease, amyotrophic lateral sclerosis-frontal temporal dimensia (ALS-FTLD), long-QT syndrome, spinocerebellar ataxias, fragile X syndrome, and the like. Determining not only how many repeats are present, but also any modifications within those repeats can provide much-needed data for development of diagnostics, prognostics, and theranostics for patients.

In other embodiments, as noted above, heterochromatic DNA can be treated to footprint agents bound to the chromatin, e.g., histone proteins, RNA factors, regulatory proteins, etc. During a subsequent sequencing reaction, long sequencing reads are generated, and these sequencing reads comprise both polynucleotide sequence information and kinetic information, and the structure of the genomic DNA is analyzed. Although the footprinting assay described above with regards to expression analysis involves removal of only a portion of the histones, i.e., those that are less tightly bound, footprinting assays can also be performed that remove all bound agents prior to sequencing. The patterns of the introduced modifications present in the resulting sequencing reads is therefore indicative of all positions at which the modifying agent was blocked, which are indicative of an agent bound to the genomic nucleic acids sample during the modification reaction.

In related embodiments, regions of euchromatin and hetrochromatin can be distinguished based upon the density of modifications introduced. Since heterochromatin is more tightly structured, fewer bases are accessible to a modification enzyme, but euchromatin tends to be more loosely structured with a higher percentage of bases available for modification. As such, treating a chromosome with a modification enzyme, removing the nucleic acid from the chromatin, and sequencing the nucleic acid allows identification of blocks of sequence that are putative heterochromatin (low density of modifications) and putative euchromatin (high density of modifications). This same method will also identify regions in the euchromatin where agents are bound, since there will be a "footprint" that lacks modification at loci that are blocked, e.g., by a bound protein. Yet further, chromatin can be subjected to specific treatments that remove only part of the higher-order structure prior to modification, and the patterns of modification that are produced after different types of treatments is indicative of the locations of the various different constituents of the higher-order chromatin structure.

Further, analysis of methylation patterns in pathogenic organisms can provide insight into the biological basis for their pathogenicity. This insight can be used to determine appropriate treatments, or to develop new treatments for combating individual infections and widespread outbreaks. A recent study has implicated the activity of a methyltransferase in the pathogenicity of an *E. coli* strain responsible for an outbreak in Germany, and this finding is indicative that methyltransferases, and potentially other modifying agents, may be good targets for drug development efforts to combat outbreaks. More information on the role of long readlength combined with modification detection during single-molecule real-time sequencing is provided in the article entitled, "Origins of the *E. coli* Strain Causing an Outbreak of Hemolytic-Uremic Syndrome in Germany" (Rasko, et al., New Engl. J. Med. 2011; 365:709-71), which is incorporated herein by reference in its entirety for all purposes.

Yet further aspects of the invention are directed to analysis of hemimodification analysis. When modified DNA is replicated in a cell, the daughter duplexes have one strand from the original DNA and the other strand is "nascent" or newly synthesized based on the sequence of the parental strand. When the DNA to be replicated has modified bases (e.g., methylated bases), the resulting duplex is "hemimodified," meaning that only the parental strand has the modification. As such, the nascent strand must be modified after synthesis to add these modified bases, thereby providing a daughter duplex having the same modifications as the original parental duplex. In vivo, specific enzymes (e.g., maintenance methyltransferases) are responsible for identifying hemi-modified nucleic acids and restoring the original modification complement of the parental duplex molecule. Maintenance of the modification status of the genome of an organism is important for the control of transcriptional activity, as well as distinction between "self" and "non-self" nucleic acids, e.g., for pathogen identification. Given that hemi-modified nucleic acids are important in cellular mechanisms involving cell division, DNA repair, and self-recognition, the ability to identify these transient molecules in genomic DNA sample will allow identification of actively dividing cells, and provide insight in to biological outcomes when such modification status is not properly maintained, e.g., in cancer development or pathogenic infection. Single-molecule, real-time sequencing methodologies allow the data necessary to not only map a sequencing read to a particular genomic region, but also to determine the modification status of the genomic nucleic acid itself. In particularly preferred embodiments, both the modified and unmodified strand are sequenced in a single template molecule such that a single resulting sequencing reads has both base sequence data and kinetic data that is indicative of the modification status of both strands of the template. Preferred template molecules are provided, e.g., in U.S. Patent Publication No. 2009/0298075, which is incorporated herein by reference in its entirety for all purposes.

IX. Screening Methods

DNA methylation patterns are known to be established and modified in response to environmental factors by a complex interplay of multiple different DNA methyltransferases, e.g., DNMT1, DNMT3A, and DNMT3B. (See, e.g., Li, et al. (1992) Cell 69(6):915-926.) Knowledge of the patterns that are indicative of various environmental exposure in combination with sequencing methods that generate both polynucleotide sequence data and modification data provides a screening method for determining whether an individual has been exposed to an environmental trigger, e.g., toxin, teratogen, carcinogen, radiation, malnutrition, pathogen, infection, etc. In certain embodiments, the screening comprises detecting DNA damage-related modifications, e.g., 8oxoG, thymidine dimers, and crosslinking, which are indicative of an exposure to a chemical or radiation that induces such damage.

In other embodiments, the screening comprises detecting modifications related to activation of an immune response. Such an activation can be indicative of an exposure to a pathogen or other infectious agent, or can be a response to an injury. In yet further embodiments, the screening comprises detecting modifications related to changes in the endocrine system, which can be indicative of exposure to environmental toxins, such as endocrine disruptors. The effects of exposure to endocrine disruptors is of particular interest because it can cause cancerous tumors, birth defects, and other developmental disorders. Changes in the endocrine system can also be the result of natural changes that occur during aging, e.g., puberty- or menopause-related changes. Given the interest in studying and managing both early-puberty and early-menopause, these methods provide a strategy for identification of such changes even before they are outwardly visible in an individual. Further, the specific endocrine changes taking place may be indicative of the cause of the physical manifestation. For example, the particular changes in modification patterns in an individual experiencing precocious puberty could help to determine if the early onset of puberty is due to exposure to a particular environmental toxin or not.

Yet further, it is well known that underlying a phenotypic trait are both genetic and environmental factors. Detection and mapping of epigenetic modifications provides a strategy for teasing apart the contributions of each by monitoring environmentally-induced epigenetic changes and determining the effect of those epigenetic changes on the phenotype of an individual. Such changes may be found in the DNA itself, or may be found in RNAs, which can change the translation of the RNAs into proteins, thereby impacting phenotype of an organism.

Further, where a treatment regimen involves changing expression patterns in an individual's genome, modification sequencing can be used as a tool to determine whether a treatment is working. For example, where a drug is intended to increase expression of a gene or gene pathway, and that increased expression is due to a known change in methylation of the gene(s), nucleic acids from the tissue where the change is expected can be sequenced prior to treatment (control) and during treatment to determine if the treatment is having the intended effect (is efficacious). Further, the individual could be screened periodically thereafter to screen for development of drug/treatment tolerance that might indicate a need for an increased dose or an alternative treatment.

X. Genome Tagging

While many of the methods described herein involve detection of modifications already present in a nucleic acid sample from a biological source, in certain embodiments modifications can be added to a nucleic acid sample, e.g., to "tag" or "barcode" it so it can be identified in a later step of an analysis by virtue of the presence of the modifications. In some preferred embodiments, barcodes are used to tag nucleic acids from different sources so they can be pooled, sequenced in a single reaction volume, and the sequences linked back to the source by virtue of the barcode sequences within the sequence reads. In certain preferred embodiments, the modifications introduced to tag or barcode a sample are not native to the sample. While modification-based barcodes are discussed at length herein, it will be understood that other types of barcodes can also be used to tag nucleic acids in the methods described herein, e.g., barcodes lacking modifications but having unique sequence identifiers.

In certain embodiments, nucleic acids from two different sources are sequenced in a single nucleic acid sequencing reaction mixture. To facilitate distinction of the sequence reads from one source from the sequence reads from another source, one of the nucleic acid samples can be altered by adding a modification that is absent from the other nucleic acid sample. The two samples can then be combined and sequenced together. The resulting sequencing reads comprise both sequence data and modification data, the latter of which is used to assign a given sequencing read to a particular source. In one such embodiment, a modification is added to DNA from a first twin, but not to DNA from the second twin. The two DNAs are sequenced together and any differences found can be mapped to either the first or second twin based upon the presence or absence of the modification, respectively. In certain embodiments, the sequencing is performed iteratively with a first iteration having the first twin's DNA modified, and the second iteration having the second twin's DNA modified. This allows interrogation of not only sequence data, but also modification data that is present in the native from of the unmodified DNA. In certain embodiments, the modification added is not naturally present in the DNA of the twins' species.

In some embodiments DNA modification information can be used to tag different portions within a single genome or identify locations within a set of genomes. For example, in the field of genome assembly, it is often useful to have, for a particular sequence, approximate information about its location of origin within a genome. Methods such as optical mapping can provide this information but are expensive and require extra processing steps. Methods to produce systematic patterns of DNA modification can help provide this approximate location information. In this role it is analogous to the use of endogenous methylation to assist with assembly, but without the dependency on an endogenous source of diversity in modification with position. One method of producing such a position-dependent modification pattern is by cultivating synchronized cell populations in medium containing modified nucleotide substrates. These modified nucleotides can comprise chemical groups that are found in the organism naturally, such as methyl groups on adenosine, or modifications that are found in living organisms but are not native to the organism in question, or can represent entirely non-natural modifications. Means such as electroporation may be needed to ensure that cells take up the nucleotides, but once the modified nucleotides are available to the genome synthesis process, the DNA will take up modified bases in proportions that reflect the mixture that is applied. By changing the mixture over the course of genome synthesis, different "tags" can be applied to different locations within the genome. The tags can be binary (the presence or absence of a particular modified base indicating a particular range of locations, or continuum (where the proportion of modified nucleotides in the DNA encodes continuous variable such as position). In a preferred embodiment, a continuous gradient is applied beginning with the origin of replication at one level of modification and continuously changing by adjustment of the proportion of nucleotides in the growth medium to a different level at the end of genome synthesis (in the synchronized population). In this embodiment, an estimator of modification density would be computed over a window of fixed or variable size and the modification density can then provide information to confirm or refute a potential genome assembly structure. In another preferred embodiment, the level of modification would be changed periodically two or more cycles over the duration of genome synthesis and would provide finer-grained resolution on position at the expense of ambiguity as to which of the cycles is represented. This would be better suited to repeats that have a structure that is smaller compared with the genome size, while the former method would be better with repeats that have a characteristic size scale that is comparable with the genome size. When repeats have characteristic repeat sizes scales that are both large and small, both methods can be applied simultaneously using different modifications. In these methods, the type of modification would be inferred either from the base that is modified or from the kinetic signature that is observed, or a combination of these features, then after binning by modification type, the window calculation would be performed as before and then the results from the two methods would be used in tandem to provide a location that is both precise and unambiguous. This method can be extended to as many nucleotide types as needed, limited only by counting statistics of how many modified bases need to be counted to produce a reliable estimator, and how many of those bases are contained within a particular window size.

Another method of producing position-dependent modification is by restriction digestion of fragments followed by size separation on a gel. In this method, restriction endonucleases that cut infrequently (compared with the read length of the sequencing system) would be desirable in order to produce information that is useful above and beyond what normal assembly algorithms can achieve. For example, with a 30,000 base read length, it would be desirable to produce a range of fragment sizes that range from 60,000 bases up to several hundred thousand bases. These can then be size-fractionated on a gel, cut into small bins, chemically modified by any of a number of methods (for example, through the use of different doses of the nonspecific methyltransferase mentioned elsewhere in this document. These fractions can then be pooled and sequenced. During sequencing, the degree of observed modification in the DNA would then provide an upper bound on how far it is to the nearest restriction recognition sequence, and this information would be useful in resolving which of several possible assemblies is the correct assembly.

Another method of producing position-dependent modification is by using cloning methods. If a BAC library or fosmid library is constructed from the genome of interest, sampled into pools with less than 1× coverage of the genome and then methylated to different degrees, this will allow identification of the pool from which the molecule is drawn. This information can then be used to confirm or refute hypotheses derived from sequence assembly as to the correct structure of the genome.

Another method of producing position-dependent modification in the DNA would be to physically elongate molecules having a common terminus and then subject the molecules to a spatially varying dose of a modifying agent or a cofactor or substrate of the modifying agent. Methods for elongating molecules are known in the art, e.g., Turner, et al. (2002) Physical Review Letters 88: 128103-1-128103-4; Cabodi, et al. (2002) Analytical Chemistry 74: 5169-5174; Tegenfeldt, et al. (2004) Anal Bioanal Chem 378: 1678-92; Persson, et al. (2010) Chemical Society Reviews 39: 985-999; and Hastie, et al. (2013) PLoS ONE 8(2): e55864, all of which are incorporated herein by reference in their entireties for all purposes. Another method of elongating the molecules is to attached them to a solid support and apply a perpendicular force using electric fields or gradient magnetic forces on magnetic particles attached to the DNA molecules. Then the gradient of modification can be applied by using diffusion to create a gradient of agent dose or other means known in the art for creating a vertical gradient.

In some embodiments, gene expression can be determined by growing cells in a medium comprising modified rNTPs. The mRNAs from the cells are collected and sequenced to determine which comprise the modified rNTPs, and were therefore transcribed during the growth in the medium comprising the modified rNTPs. The cells can be treated by different environmental stimuli or agents to assess how these changes in growth conditions impact transcription. The method is especially helpful in distinguishing between mRNAs that have a long lifetime in a cell versus those that are being expressed at a high level because the former will only have a small number of transcripts with the modified rNTPs even if there is a large number of total transcripts present in the cell. In contrast, the latter will have all or nearly all transcripts comprising the modified rNTPs.

Similarly, a culture comprising multiple different microorganisms can be analyzed to determine which are actively growing, e.g., under differing conditions, by adding modified dNTPs to the culture. The DNA from the microorganisms is collected and sequenced, and the organisms that incorporated the modified dNTPs into their DNA are identified as those that were actively growing in the culture. As such, sequencing data that comprises both polynucleotide sequence data and modification data can not only identify the organism based on similarity to known reference sequences, it can also identify which are actively growing in a mixed culture.

In certain aspects, the invention provides methods for determining sequence and modification differences between nucleic acids from different tissues that involve incorporation of nucleic acids from both sources into a single template nucleic acid molecule. Such methods typically involve treating the nucleic acids from a first source with a modifying agent as described elsewhere herein, hybridizing nucleic acids from both sources together to produce double-stranded hybrid molecules comprising one nucleic acid strand from the first source and one nucleic acid from the second source. Hybrid molecules are selected from the mixture, which also comprises duplexes that are not hybrids, e.g., that have two strands from the same source. Such a selection is typically based upon secondary structures that form due to mismatches between the two strands of the hybrid molecules. For example, where one source is tumor tissue and the other source is normal tissue, it is expected that large-scale mutations (large insertions, deletions, translocations, inversions, etc.) in the tumor-derived nucleic acid will cause a looping out of the nucleic acid from the normal tissue due to a lack of a complementary sequence in the tumor-derived strand. As such the selection can be based upon binding of single-strand-specific agents to the hybrid molecules and the capture of these single-strand binding agents, e.g. through affinity binding methods, bead capture methods, and the like. The nucleic acids not captures are removed and the hybrid molecules are released into solution. The hybrid molecules can be further manipulated to prepare them for sequencing, e.g., by addition of adaptors, preferably stem-loop adapters, and this can be performed either before or after the selection step. The hybrid molecule is used as a template in a sequencing reaction in which both polynucleotide sequence data and modification data are collected, and this data is analyzed to both provide a sequence for both strands of the hybrid molecule and detect the modifications within these strands. The portions of the polynucleotide sequence read(s) collected during the sequencing that comprise modifications added by the modifying agent are identified as being from the first source, and the portions of the polynucleotide sequence read(s) collected during the sequencing that do not comprise modifications added by the modifying agent are identified as being from the second source. The differences between the polynucleotide sequence data from the first and second source are further analyzed based upon knowledge about the sources. For example, where the first source is tumor tissue and the second source is normal tissue, differences between the polynucleotide sequence data are likely indicative of mutations in the tumor-derived nucleic acid that are related to the tumor phenotype. In certain embodiments, the mismatches in the hybrid molecules are repaired using nucleotides having distinguishable modifications, such that they are identifiable from the modification data collected from the sequencing reaction. The loci at which they are detected are indicative of a previous mismatch between the nucleic acids from the two sources, although the nature of the mismatch may not be discernible.

XI. Method for Identification of Novel Methyltransferases in Bacterial Strains

Identifying novel methylation enzymes is challenging, but a method is provided herein for rapidly identifying such enzymes and/or bacterial strains producing such enzymes. The method uses single-molecule, real-time sequencing (e.g., SMRT® Sequencing from Pacific Biosciences, Menlo Park, Calif.) to detect methylated nucleotides within a plasmid template molecule. The sequencing data generated can also be analyzed to determine sequence specificity of the enzyme, as well as its putative restriction enzyme partner, such as in the case of prokaryotic restriction-modification (RM) systems.

The sequence of the AllMer plasmid has all possible combinations of multi-base motifs, e.g., preferably four-base, five-base, and/or six-base motifs. The region of the plasmid comprising the multi-base motifs is preferably about 1000 base pairs in length, but can be longer, and can include multiple copies of one, some, or all of the multi-base motifs. The plasmid also comprises a vector region that comprises all the necessary elements for plasmid propagation in a host organism, e.g., a bacterial strain. The vector region is typically about 2-3 kb in length. The plasmid also comprises a restriction site, preferably within the vector region. Cleavage at the restriction site provides a double-stranded linear molecule having a blunt end or a 3' or 5' overhang, depending on the type of restriction site. Stem-loop adaptors are ligated to the ends of the linear molecule to produce a sequencing template, termed a "SMRTbell™ template," that is a topologically closed molecule that forms a single-stranded circular template when the double-stranded portion is separated (since at each end the termini are connected via a stem-loop adaptor). The sequencing template is typically 3-6 kb in length, but can be longer. In some embodiments, there are two restriction sites that flank the multi-base motif region so the sequencing template need not comprise the vector region, whose sequence is already known.

The plasmid is cotransfected into a host organism with an expression vector encoding a putative methyltransferase gene or other genomic sequence that might contain such a gene. The host organism is propagated and the AllMer plasmid isolated, converted into a sequencing template, and sequenced, preferably using a sequencing technology that detects modified bases such as SMRT® Sequencing. If the sequence of the AllMer plasmid is methylated, the locations of the methylated bases and flanking sequences are used to characterize the putative methyltransferase, e.g., with regards to its sequence specificity, activity, and the like. In preferred embodiments, the host organism lacks any methyltransferases, or has only well-characterized methyltransferases with recognition sequences different from those of the putative methyltransferase in the expression vector.

In some embodiments, the adaptors linked to the ends of the linearized AllMer plasmid comprise barcodes to allow multiplexed sequencing reactions from multiple host organisms. The sequences of the barcodes identify from which host organism a particular AllMer plasmid was isolated, and therefore what putative methyltransferase is responsible for the methylation detected. Since both strands of the AllMer plasmid are sequenced, strand-specific modifications are detectable. Further, in alternative embodiments, one or more additional modification-generating enzymes could be included in the host organism, e.g., within the expression vector, in a second expression vector, or may be expressed from the host organism's own genome. such modification-generating enzymes can serve to enhance detection of modifications in the AllMer plasmid, e.g., by further modifying methylated bases. Such further modification includes, but is not limited to, glucosylation (e.g., by a glucosyltransferase) or hydroxylation (e.g., by a TET hydroxylase enzyme).

In certain embodiments, rather than cotransfecting the AllMer with an expression vector, the AllMer is transfected into a host organism and used to detect base-modification activity expressed by the host organism itself. In yet further embodiments, multiple different AllMer plasmids can be used that still contain the same sets of multi-base motifs, but in detectably different conformations or orders such that sequencing reads would identify a particular AllMer plasmid. This embodiment is contemplated as an alternative to the barcoding of the adaptors, since the identifying sequences would be within the AllMer plasmid sequence rather than the adaptors. Alternatively, multiple different allMer plasmids could be used in combination with barcoded adaptors.

XII. Methyltransferases as Analytical Tools

Methyltransferases are key to various different analytical tools provided herein, some of which have been discussed above. In all of these applications, both the presence of a particular modification, as well as the sequence context in which it occurs, can be used to identify the source of a nucleic acid of interest. In some preferred embodiments, the methyltransferases used are nonspecific, i.e., they add a methyl group regardless of the sequence flanking a base to be methylated. In other words, they have no particular sequence motif that they target, although they still methylate only those bases that are sufficiently exposed to allow access by the enzyme. Further, although they typically have no "recognition sequence" per se, they are specific for a particular base to be methylated, e.g., A or C. For example, treatment of naked DNA with a nonspecific adenine methyltransferase would catalyze addition of a methyl group to most or all of the adenines within the DNA molecule.

In certain aspects, a methyltransferase is used to mark a nucleic acid so that it can be later identified and/or distinguished from other nucleic acids. For example, a nucleic acid sample directly from a source can be methylated and then subjected to amplification. Data from subsequent sequencing of the resulting pool of original nucleic acids and amplicons thereof would be able to distinguish between sequence reads from the original sample and the amplicons because the original sample would be highly methylated and the amplicons would not. One or more methyltransferases can also be cloned into an organism of interest so nucleic acids from that organism can be distinguished from nucleic acids from organisms that do not contain the methyltransferase gene. As such, "labeling" of the nucleic acids taking place in vivo allows identification of the source of the nucleic acids during a sequencing reaction. In a similar strategy, a cloned methyltransferase can be regulated by a promoter of interest, and the methylation status of nucleic acids isolated from the organism is indicative of the activation state of the promoter. Similarly, a primary nucleic acid sample can be labeled by treatment with a methyltransferase at the source to allow later identification of contaminating nucleic acids, which would not comprise the specific methylation pattern of the treated sample. This could be particularly useful for forensic applications where contamination can result in an inability to identify the original sample, or in the study of ancient nucleic acids, where contamination can result in "ancient" contigs having modern nucleic acid sequences. In related aspects, such marking can be used as a security marker to mark DNA having a proprietary origin. DNA modified using the methyltransferase is still useful for most applications, but it would carry modifications that can be used to identify its source.

In further aspects, use of methyltransferases can be useful in designing constructs for molecular biology applications. For example, artificial sequences (such as adaptors, primer-binding sites, etc.) can be tagged with modified bases prior to linking them with a nucleic acid of interest ("target"). Subsequent sequencing that detects the modified bases uses that information, in combination with the sequence data, to identify the artificial sequences and to distinguish them from the target nucleic acid. Addition of modification to either artificial or sample nucleic acids can also serve a protective function where it makes the nucleic acid unrecognizable to an enzyme that would otherwise alter it. For example, the modifications may prevent internal cleavage by an endonuclease, degradation at a free end by an exonuclease, ligation to an exogenous sequence (e.g., used to remove "non-target" nucleic acids from a mixture), addition of further modifications (e.g., DNA damage), etc. In a specific implementation, a potentially dangerous nucleic acid sequence, such as from a pathogenic organism, is treated to prevent its expression if it were to be accidently released, inhaled, injected, or ingested. For example, a viral nucleic acid can be rendered biologically incompetent for integration into a host genome.

In yet further aspects, methyltransferases can be used to modify genomic function in various ways. For example, introducing modifications into the genomes of pathogenic organisms, e.g., bacteria, fungi, or viruses, can be a strategy for inactivating the genome of the organism or otherwise altering the life/cell cycle, where enzymes needed for such processes are sensitive to such modifications. For example, cancer cells can be targeted by an expression vector (e.g., a plasmid or virus) carrying the desired methyltransferase, and once inside the cancer cells the methyltransferase is expressed and methylates the genome of the cancer cell, inactivating it or otherwise causing programmed cell death. In another example, a pathogenic bacteria can be targeted, "infected" with a methyltransferase, and the resulting changes in expression patterns either slow or stop the growth of the bacterium and allow clearance from the infected individual. Alternatively, growth of a beneficial bacterium could be enhanced by a similar method, but where the modification served to increase efficiency of nutrient uptake, speed the cell cycle, or the like.

In a more subtle implementation, targeted modifications to genomic regions associated with transcriptional regulation, e.g., promoters, termination sequences, etc., serves to modulate transcription of a gene or genes of interest. For example, fusion of a methyltransferase or other modification-introducing gene product with a locus specific protein (or nucleic acid) can allow targeting of the resulting modifications to that locus in a genome or other nucleic acid molecule. For example, a transcription factor specific for a particular gene or gene family binds to the promoter sequence(s) and brings the attached modification enzyme into close proximity where it can introduce modifications to the promoter region and/or gene(s). Such modifications alter expression of the gene(s), and can serve to increase expression, decrease expression, or entirely silence the gene. In a specific embodiment, a methyltransferase gene can be integrated into a host organism under the control of an externally activatable promoter. This functions as an artificial apoptosis mechanism, allowing the practitioner to activate the expression and induce cell death at will.

XIII. Systems

The invention also provides systems that are used in conjunction with the compositions and methods of the invention in order to provide for real-time single-molecule detection of analytical reactions. In particular, such systems typically include the reagent systems described herein, in conjunction with an analytical system, e.g., for detecting data from those reagent systems. In certain preferred embodiments, analytical reactions are monitored using an optical system capable of detecting and/or monitoring interactions between reactants at the single-molecule level. For example, such an optical system can achieve these functions by first generating and transmitting an incident wavelength to the reactants, followed by collecting and analyzing the optical signals from the reactants. Such systems typically employ an optical train that directs signals from the reactions to a detector, and in certain embodiments in which a plurality of reactions is disposed on a solid surface, such systems typically direct signals from the solid surface (e.g., array of confinements) onto different locations of an array-based detector to simultaneously detect multiple different optical signals from each of multiple different reactions. In particular, the optical trains typically include optical gratings or wedge prisms to simultaneously direct and separate signals having differing spectral characteristics from each confinement in an array to different locations on an array based detector, e.g., a CCD, and may also comprise additional optical transmission elements and optical reflection elements.

An optical system applicable for use with the present invention preferably comprises at least an excitation source and a photon detector. The excitation source generates and transmits incident light used to optically excite the reactants in the reaction. Depending on the intended application, the source of the incident light can be a laser, laser diode, a light-emitting diode (LED), a ultra-violet light bulb, and/or a white light source. Further, the excitation light may be evanescent light, e.g., as in total internal reflection microscopy, certain types of waveguides that carry light to a reaction site (see, e.g., U.S. Application Pub. Nos. 20080128627, 20080152281, and 200801552280), or zero mode waveguides, described below. Where desired, more than one source can be employed simultaneously. The use of multiple sources is particularly desirable in applications that employ multiple different reagent compounds having differing excitation spectra, consequently allowing detection of more than one fluorescent signal to track the interactions of more than one or one type of molecules simultaneously (e.g., multiple types of differentially labeled reaction components). A wide variety of photon detectors or detector arrays are available in the art. Representative detectors include but are not limited to an optical reader, a high-efficiency photon detection system, a photodiode (e.g. avalanche photo diodes (APD)), a camera, a charge-coupled device (CCD), an electron-multiplying charge-coupled device (EMCCD), an intensified charge coupled device (ICCD), and a confocal microscope equipped with any of the foregoing detectors. For example, in some embodiments an optical train includes a fluorescence microscope capable of resolving fluorescent signals from individual sequencing complexes. Where desired, the subject arrays of optical confinements contain various alignment aides or keys to facilitate a proper spatial placement of the optical confinement and the excitation sources, the photon detectors, or the optical train as described below.

The subject optical system may also include an optical train whose function can be manifold and may comprise one or more optical transmission or reflection elements. Such optical trains preferably encompass a variety of optical devices that channel light from one location to another in either an altered or unaltered state. First, the optical train collects and/or directs the incident wavelength to the reaction site (e.g., optical confinement). Second, it transmits and/or directs the optical signals emitted from the reactants to the photon detector. Third, it may select and/or modify the optical properties of the incident wavelengths or the emitted wavelengths from the reactants. Illustrative examples of such optical transmission or reflection elements are diffraction gratings, arrayed waveguide gratings (AWG), optical fibers, optical switches, mirrors (including dichroic mirrors), lenses (including microlenses, nanolenses, objective lenses, imaging lenses, and the like), collimators, optical attenuators, filters (e.g., polarization or dichroic filters), prisms, wavelength filters (low-pass, band-pass, or high-pass), planar waveguides, wave-plates, delay lines, and any other devices that guide the transmission of light through proper refractive indices and geometries. One example of a particularly preferred optical train is described in U.S. Patent Pub. No. 20070036511, filed Aug. 11, 2005, and incorporated by reference herein in its entirety for all purposes.

In a preferred embodiment, a reaction site (e.g., optical confinement) containing a reaction of interest is operatively coupled to a photon detector. The reaction site and the respective detector can be spatially aligned (e.g., 1:1 mapping) to permit an efficient collection of optical signals from the reactants. In certain preferred embodiments, a reaction substrate is disposed upon a translation stage, which is typically coupled to appropriate robotics to provide lateral translation of the substrate in two dimensions over a fixed optical train. Alternative embodiments could couple the translation system to the optical train to move that aspect of the system relative to the substrate. For example, a translation stage provides a means of removing a reaction substrate (or a portion thereof) out of the path of illumination to create a non-illuminated period for the reaction substrate (or a portion thereof), and returning the substrate at a later time to initiate a subsequent illuminated period. An exemplary embodiment is provided in U.S. Patent Pub. No. 20070161017, filed Dec. 1, 2006.

In particularly preferred aspects, such systems include arrays of reaction regions, e.g., zero mode waveguide arrays, that are illuminated by the system, in order to detect signals (e.g., fluorescent signals) therefrom, that are in conjunction with analytical reactions being carried out within each reaction region. Each individual reaction region can be operatively coupled to a respective microlens or a nanolens, preferably spatially aligned to optimize the signal collection efficiency. Alternatively, a combination of an objective lens, a spectral filter set or prism for resolving signals of different wavelengths, and an imaging lens can be used in an optical train, to direct optical signals from each confinement to an array detector, e.g., a CCD, and concurrently separate signals from each different confinement into multiple constituent signal elements, e.g., different wavelength spectra, that correspond to different reaction events occurring within each confinement. In preferred embodiments, the setup further comprises means to control illumination of each confinement, and such means may be a feature of the optical system or may be found elsewhere is the system, e.g., as a mask positioned over an array of confinements. Detailed descriptions of such optical systems are provided, e.g., in U.S. Patent Pub. No. 20060063264, filed Sep. 16, 2005, which is incorporated herein by reference in its entirety for all purposes. While optical systems such as those described above are a preferred detection system, other detection systems known to those of skill in the art are also contemplated, in particular, systems that detect passage of molecules through pores in a membrane or other surface, e.g., nanopores; systems that detect charge-based changes; systems that detect pH-based changes; and systems that detect electrical changes, and the like.

The systems of the invention typically include information processors or computers operably coupled to the detection portions of the systems, in order to store the signal data obtained from the detector(s) on a computer readable medium, e.g., hard disk, CD, DVD or other optical medium, flash memory device, or the like. For purposes of this aspect of the invention, such operable connection provides for the electronic transfer of data from the detection system to the processor for subsequent analysis and conversion. Operable connections may be accomplished through any of a variety of well-known computer networking or connecting methods, e.g., Firewire®, USB connections, wireless connections, WAN or LAN connections, or other connections that preferably include high data transfer rates. The computers also typically include software that analyzes the raw signal data, identifies signal pulses that are likely associated with incorporation events, and identifies bases incorporated during the sequencing reaction, in order to convert or transform the raw signal data into user interpretable sequence data (see, e.g., Published U.S. Patent Application No. 2009-0024331, the full disclosure of which is incorporated herein by reference in its entirety for all purposes).

Exemplary systems are described in detail in, e.g., U.S. patent application Ser. No. 11/901,273, filed Sep. 14, 2007 and U.S. patent application Ser. No. 12/134,186, filed Jun. 5, 2008, the full disclosures of which are incorporated herein by reference in their entirety for all purposes.

Further, the invention provides data processing systems for transforming raw data generated in an analytical reaction into analytical data that provides a measure of one or more aspects of the reaction under investigation, e.g., transforming signals from a sequencing-by-synthesis reaction or pore-translation reaction into nucleic acid sequence read data, which can then be transformed into consensus sequence data. In certain embodiments, the data processing systems include machines for generating nucleic acid sequence read data by polymerase-mediated processing of a template nucleic acid molecule (e.g., DNA or RNA). The nucleic acid sequence read data generated by such a reaction is representative of the nucleic acid sequence of the nascent polynucleotide synthesized by a polymerase translocating along a nucleic acid template only to the extent that a given sequencing technology is able to generate such data, and so may not be identical to the actual sequence of the nascent polynucleotide molecule. For example, it may contain a deletion or a different nucleotide at a given position as compared to the actual sequence of the polynucleotide, e.g., when a nucleotide incorporation is missed or incorrectly determined, respectively. As such, it is beneficial to generate redundant nucleic acid sequence read data, and to transform the redundant nucleic acid sequence read data into consensus nucleic acid sequence data that is generally more representative of the actual sequence of the polynucleotide molecule than nucleic acid sequence read data from a single read of the nucleic acid molecule. Redundant nucleic acid sequence read data comprises multiple reads, each of which includes at least a portion of nucleic acid sequence read that overlaps with at least a portion of at least one other of the multiple nucleic acid sequence reads. As such, the multiple reads need not all overlap with one another, and a first subset may overlap for a different portion of the nucleic acid sequence than does a second subset. Such redundant sequence read data can be generated by various methods, including repeated synthesis of nascent polynucleotides from a single nucleic acid template, synthesis of polynucleotides from multiple identical nucleic acid templates, or a combination thereof.

In another aspect, the data processing systems can include software and algorithm implementations provided herein, e.g. those configured to transform redundant nucleic acid sequence read data into consensus nucleic acid sequence data, which, as noted above, is generally more representative of the actual sequence of the nascent polynucleotide molecule than nucleic acid sequence read data from a single read of a single nucleic acid molecule. Further, the transformation of the redundant nucleic acid sequence read data into consensus nucleic acid sequence data identifies and negates some or all of the single-read variation between the multiple reads in the redundant nucleic acid sequence read data. As such, the transformation provides a representation of the actual nucleic acid sequence of the nascent polynucleotide complementary to the nucleic acid template that is more accurate than a representation based on a single read.

Various methods and algorithms for data transformation employ data analysis techniques that are familiar in a number of technical fields, and are generally referred to herein as statistical analysis. For clarity of description, details of known techniques are not provided herein. These techniques are discussed in a number of available reference works, such as those provided in U.S. Pat. Nos. 8,182,993 and 8,370,079; U.S. Patent Publication No. 2012/0330566; U.S. Ser. No. 13/468,347, filed May 10, 2012; U.S. Ser. No. 61/784,219, filed Mar. 14, 2013; U.S. Ser. No. 61/671,554, filed Jul. 13, 2012; and U.S. Ser. No. 61/116,439, filed Nov. 20, 2008, the disclosures of which are incorporated herein by reference in their entireties for all purposes.

The software and algorithm implementations provided herein are preferably machine-implemented methods, e.g., carried out on a machine comprising computer-readable medium configured to carry out various aspects of the methods herein. For example, the computer-readable medium preferably comprises at least one or more of the following: a) a user interface; b) memory for storing raw analytical reaction data; c) memory storing software-implemented instructions for carrying out the algorithms for transforming the raw analytical reaction data into transformed data that characterizes one or more aspects of the reaction (e.g., rate, consensus sequence data, etc.); d) a processor for executing the instructions; e) software for recording the results of the transformation into memory; and f) memory for recordation and storage of the transformed data. In preferred embodiments, the user interface is used by the practitioner to manage various aspects of the machine, e.g., to direct the machine to carry out the various steps in the transformation of raw data into transformed data, recordation of the results of the transformation, and management of the transformed data stored in memory.

As such, in preferred embodiments, the methods further comprise a transformation of the computer-readable medium by recordation of the raw analytical reaction data and/or the transformed data generated by the methods. Further, the computer-readable medium may comprise software for providing a graphical representation of the raw analytical reaction data and/or the transformed data, and the graphical representation may be provided, e.g., in soft-copy (e.g., on an electronic display) and/or hard-copy (e.g., on a print-out) form.

The invention also provides a computer program product comprising a computer-readable medium having a computer-readable program code embodied therein, the computer readable program code adapted to implement one or more of the methods described herein, and optionally also providing storage for the results of the methods of the invention. In certain preferred embodiments, the computer program product comprises the computer-readable medium described above.

In another aspect, the invention provides data processing systems for transforming raw analytical reaction data from one or more analytical reactions into transformed data representative of a particular characteristic of an analytical reaction, e.g., an actual sequence of one or more template nucleic acids analyzed, a rate of an enzyme-mediated reaction, an identity of a kinase target molecule, and the like. Such data processing systems typically comprise a computer processor for processing the raw data according to the steps and methods described herein, and computer usable medium for storage of the raw data and/or the results of one or more steps of the transformation, such as the computer-readable medium described above.

Figure 3:
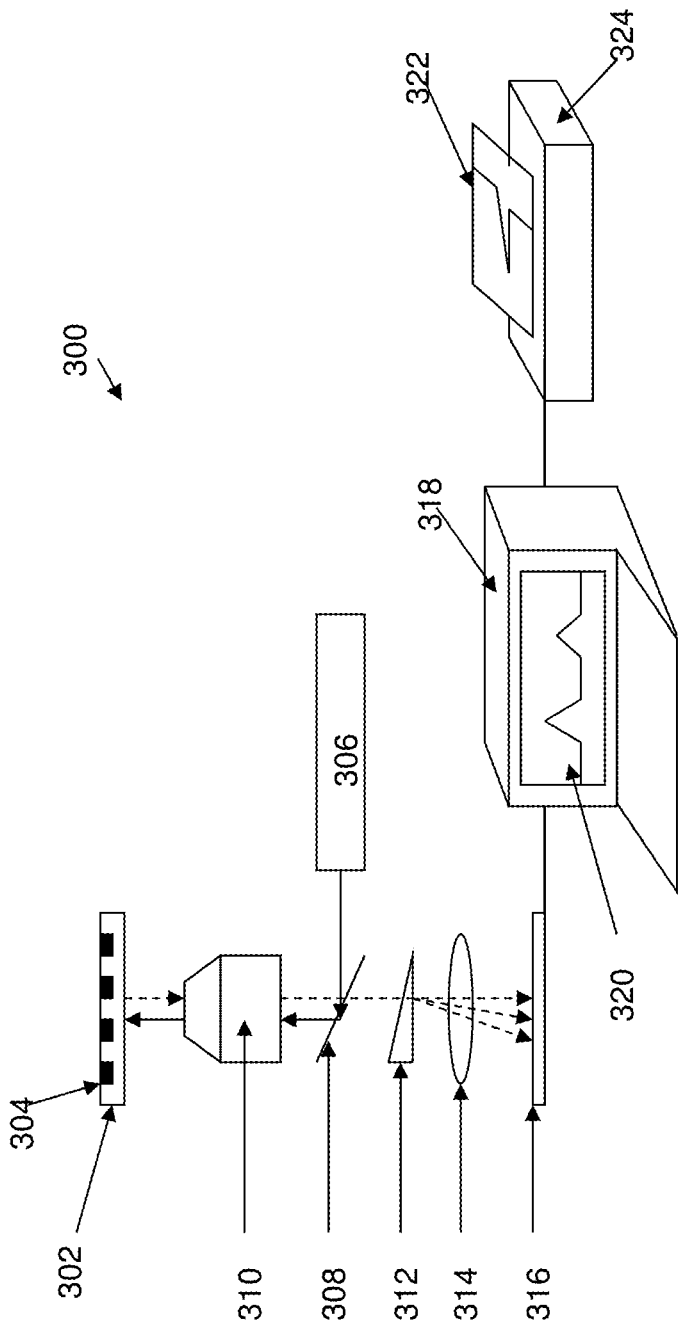
FIG. 3 provides an exemplary system of the invention.

As shown in FIG. 3, the system 300 includes a substrate 302 that includes a plurality of discrete sources of chromophore emission signals, e.g., an array of zero mode waveguides 304. An excitation illumination source, e.g., laser 306, is provided in the system and is positioned to direct excitation radiation at the various signal sources. This is typically done by directing excitation radiation at or through appropriate optical components, e.g., dichroic 308 and objective lens 310, that direct the excitation radiation at the substrate 302, and particularly the signal sources 304. Emitted signals from the sources 304 are then collected by the optical components, e.g., objective 310, and passed through additional optical elements, e.g., dichroic 308, prism 312 and lens 314, until they are directed to and impinge upon an optical detection system, e.g., detector array 316. The signals are then detected by detector array 316, and the data from that detection is transmitted to an appropriate data processing system, e.g., computer 318, where the data is subjected to interpretation, analysis, and ultimately presented in a user ready format, e.g., on display 320, or printout 322, from printer 324. As will be appreciated, a variety of modifications may be made to such systems, including, for example, the use of multiplexing components to direct multiple discrete beams at different locations on the substrate, the use of spatial filter components, such as confocal masks, to filter out-of focus components, beam shaping elements to modify the spot configuration incident upon the substrates, and the like (See, e.g., Published U.S. Patent Application Nos. 2007/0036511 and 2007/095119, and U.S. patent application Ser. No. 11/901, 273, all of which are incorporated herein by reference in their entireties for all purposes.)

XIV. Example: Analysis of Bacterial Methylomes

Sequencing template libraries were prepared as previously described (Clark, et al. (2012) *Nucleic Acids Res.,* 40, e29; and Travers, et al. (2010) *Nucleic Acids Res.* 38, e159). Briefly, genomic DNA samples were sheared to an average size of ~800 base pairs via adaptive focused acoustics (Covaris; Woburn, Mass., USA), end repaired, and ligated to stem-loop adapters to form SMRTbell™ templates. Incompletely formed SMRTbell templates were digested with a combination of Exonuclease III (New England Biolabs; Ipswich, Mass., USA) and Exonuclease VII (Affymetrix; Cleveland, Ohio, USA). SMRT® Sequencing was carried out on the PacBio® RS (Pacific Biosciences; Menlo Park, Calif., USA) using standard protocols for small insert SMRTbell libraries. All restriction endonucleases except Eco1471 (Fermentas; Glen Burnie, Md.), Phusion-HF DNA polymerase, Antarctic Phosphatase, T4-DNA ligase, and *E. coli* competent cells were from New England Biolabs Inc. (Ipswich, Mass., USA). Synthetic oligonucleotides were purchased from Integrated DNA Technologies (Coralville, Iowa, USA). *Geobacter metallireducens* GS-15 ATCC 53774 DNA, *Chromohalobacter salexigens* DSM 3043 DNA and *Bacillus cereus* ATCC 10987 DNA were obtained from the culture collections indicated. *Vibrio breoganii* 1C-10 DNA was a gift from Martin Polz, MIT. *Campylobacter jejuni* subsp. *jejuni* 81-176 and *Campylobacter jejuni* NCTC 11168 DNAs were a gift from Stuart Thompson, Medical College of Georgia.

Sequencing reads were processed and mapped to the respective reference sequences using the BLASR mapper (http://www[dot]pacbiodevnet[dot]com/SMRT-Analysis/ Algorithms/BLASR) and the Pacific Biosciences' SMRT Analysis pipeline (http://www[dot]pacbiodevnet[dot]com/

SMRT-Analysis/Software/SMRT-Pipe) using the standard mapping protocol. Interpulse durations (IPDs) were measured as previously described (Flusberg, et al. (2010) *Nat. Methods*, 7, 461-465) and processed as described (Clark, et al., supra) for all pulses aligned to each position in the reference sequence. To identify modified positions, Pacific Biosciences' SMRTPortal analysis platform, v. 1.3.1, which uses an in silico kinetic reference, and a t-test based kinetic score detection of modified base positions (details are available at http://www[dot]pacb[dot]com/pdf/TN Detecting_DNA_Base_Modifications.pdf). Methyltransferase target sequence motifs were identified by selecting the top one thousand kinetic hits and subjecting a +/−20 base window around the detected base to MEME-ChIP (Machanick, P. and Bailey, T. L. (2011) *Bioinformatics*. 27, 1696-7). To measure the extent of methylation for each motif in a genome, a kinetic score threshold was chosen such that 1% of the detected signals were not assigned to any MTase recognition motifs (5% for *B. cereus* to accommodate for the lower signal intensities for 4-methylcytosine). We subjected this 1% population of sequence context to another round of MEME-ChIP analysis to confirm the absence of any additional consensus motifs. No accumulation of motifs that harbored similarities to the identified active motifs were observed. All kinetic data files have been deposited in GEO (Accession #: GSE40133) (Sayers, et al. (2012) Database resources of the National Center for Biotechnology Information. *Nucleic Acids Res.*, 40 (Database issue), D13-25) (http://www[dot]ncbi[dot]nlm[dot]nih[dot]gov/geo/summary/).

The SEQWARE computer resource was used to identify restriction-modification system genes from the complete genome sequences of *G. metallireducens* GS-15 (GenBank # CP000148 and CP000149), *C. salexigens* (GenBank # CP000285), *B. cereus* (GenBank # AE017194 and AE017195), *C. jejuni* subsp. *jejuni* 81-176 (GenBank # CP000538, CP000549 and CP000550), *C. jejuni* NCTC 11168 (GenBank # AL111168) and *V. breoganii* 1C-10 (GenBank # AKXW00000000). Software modules combined with internal databases constitute the SEQWARE resource. New sequence data was scanned locally for homologs of already identified and annotated restriction-modification systems in REBASE (Roberts, R. J., et al. (2010) Nucleic Acids Res., 38, D234-D236). Sequence similarity from BLAST searches, the presence of predictive functional motifs (Posfai, et al. (1989) Nucleic Acids Res., 17, 2421-2435; and Klimasauskas, et al. (1989) Nucleic Acids Res., 17, 9823-9832) and genomic context are the basic indicators of potential new restriction-modification system components. Heuristic rules, derived from knowledge about the gene structure of restriction-modification systems, are also applied to refine the hits. Attempts are made to avoid false hits caused by strong sequence similarity of RNA and protein methyltransferases, or hits based solely on non-specific domains of restriction-modification enzymes, such as helicase or chromatin remodeling domains. SEQWARE then localizes motifs and domains, assigns probable recognition specificities, classifies accepted hits and marks Pfam relationships. All candidates are then inspected manually before being assigned as part of an restriction-modification system. The results are entered into REBASE.

Selected MTase genes were amplified from bacterial genomic DNA with Phusion-HF DNA polymerase and cloned into the plasmid pRRS as described previously (Clark, et al., supra). When no suitable sites were present elsewhere in the construct, restriction sites diagnostic for the predicted methylation pattern were incorporated into the 3'-end oligonucleotides. The presence or absence of specific methylation was determined by digesting the constructs with appropriate restriction enzymes. Host strains used for cloning included *E. coli* ER2796 (Kong, H., et al. (2000) Nucleic Acids Res., 28, 3216-3223) and *E. coli* ER2683 (Sibley, M. H. and Raleigh, E. A. (2004) Nucleic Acids Res., 32, 522-534).

The Csa_1401 and Gmet_0255 genes were cloned into a plasmid using the Gibson assembly technique (Gibson, et al. (2009) Nat. Methods 6, 343-345.). The plasmid vector was PCR-amplified, and the MTase genes were amplified using primers having 5' tails that overlap with the ends of the amplified vector. PCR-amplified DNAs were purified over a Qiagen spin column. 0.1 pmol vector was combined with 0.3 pmol MTase gene insert in 20 µl 1× Gibson assembly reaction (New England Biolabs) and incubated at 50° C. for 1 hour. 2 µl of this assembled construct was transformed into 50 µl chemical competent *E. coli* ER2796 cells and plated on LB-ampicillin plates at 37° C. overnight.

This study represented one of the first times that the complete methylation pattern of a bacterial genome has been examined. For the methyltransferases studied, seven are components of Type I restriction-modification systems and have six different recognition sequences, all of which were new. In addition, two Type III systems were found with one new recognition sequence, and two methyltransferases were part of traditional Type II systems, although the activity of the corresponding restriction endonuclease was not confirmed. Finally, four Type IIG restriction endonucleases, which contain both methyltransferase and restriction endonuclease activity in a single protein, were found, all with new specificities.

Despite the recognized importance of methylation for understanding fundamental microbiological processes, microbe adaptability and disease pathogenicity (Srikhanta, et al. (2010) Nat. Rev. Microbiol., 8, 196-206; and Casadesús, et al. (2006) Microbiol. Mol. Biol. Rev., 70, 830-56), there has not been a great deal of research into the methylation patterns of bacterial genomes, largely because of the difficulty of obtaining suitable data. One area where knowledge about the methylome is very important relates to studies trying to transform DNA into strains that contain one or more restriction-modification systems that vastly reduce transformation efficiencies. In some cases these barriers have been overcome by premethylating the DNA, or by removing the restriction-modification systems from strains (Donahue, et al. (2000) Mol. Microbiol. 37, 1066-1074; and Dong, et al. (2010) PLoS ONE 5, e9038). One problem with the latter approach is that removal of methylation systems may fundamentally change the biology of the organism under study. With the kind of analysis provided here, the restriction-modification systems likely to cause problems with transformation can be easily spotted and appropriate measures taken. Thus, the methyltransferases necessary for protection can be identified and if needed intermediate cloning hosts carrying suitable complements of methyltransferase genes can be prepared.

The results provided here show that SMRT® sequencing can provide functional information about active methyltransferases present in genomes and can decipher their recognition sequences, a task that used to be time-consuming to a point where it was not usually carried out. This, combined with the long reads provided by this technology can be an excellent adjunct to current high-throughput sequencing platforms, in that sequence assembly is facilitated and gene function is reliably documented. Further details of this study are provided in Murray, et al. (2012) Nucleic Acids Res. 40(22):11450-62, which is incorporated herein by reference in its entirety for all purposes.

It is to be understood that the above description is intended to be illustrative and not restrictive. It readily should be apparent to one skilled in the art that various embodiments and—modifications may be made to the invention disclosed in this application without departing from the scope and spirit of the invention. For example, all the techniques and apparatus described above can be used in various combinations. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A method of determining whether a cell sample comprises actively dividing cells, the method comprising:
    obtaining a non-amplified, double-stranded genomic DNA library from the cell sample;
    performing single-molecule sequencing to generate sequence reads for both strands of a plurality of individual double-stranded nucleic acids in the genomic DNA library, wherein the sequence reads comprise both base sequence data and base modification data; and
    analyzing the base sequence and base modification of the plurality of individual double-stranded nucleic acids, wherein identification of individual double-stranded nucleic acids in the genomic DNA library that are hemi-modified indicates that the cell sample comprises actively dividing cells.

2. The method of claim 1, wherein the cell sample comprises one or more type of microorganism.

3. The method of claim 2, wherein the cell sample is a metagenomic sample.

4. The method of claim 2, wherein the one or more type of microorganism is selected from the group consisting of: one or more type of bacteria, one or more type of archaean, one or more type of protozoan, one or more type of fungus, or any combination thereof.

5. The method of claim 2, wherein the one or more microorganism is a pathogenic microorganism.

6. The method of claim 1, wherein the single-molecule sequencing performed is a sequencing-by-incorporation method.

7. The method of claim 1, wherein the single-molecule sequencing performed is a nanopore sequencing method.

8. The method of claim 1, further comprising assembling one or more contigs from the sequence reads of the plurality of individual double-stranded nucleic acids.

9. The method of claim 8, wherein the assembling is based on both the base sequence data and the base modification data.

10. The method of claim 9, wherein the assembling generates a single contig for a chromosome of a microorganism in the cell sample.

11. The method of claim 1, wherein the base modification is selected from the group consisting of: methylation, hydroxymethylation, glucosylation, and combinations thereof.

12. The method of claim 1, wherein the base modification is methylation.

13. The method of claim 1, wherein the non-amplified, double-stranded genomic DNA library is not bisulfite-converted.

* * * * *